United States Patent
Zhao et al.

(10) Patent No.: US 11,155,819 B2
(45) Date of Patent: Oct. 26, 2021

(54) DOUBLE-STRANDED RNA MOLECULE TARGETING CKIP-1 AND USE THEREOF

(71) Applicant: BEIJING TIDE PHARMACEUTICAL CO., LTD., Beijing (CN)

(72) Inventors: Yanping Zhao, Beijing (CN); Hongjun Wang, Beijing (CN); Yuanyuan Jiang, Beijing (CN); Weiting Zhong, Beijing (CN); Jianmei Pang, Beijing (CN); Gong Li, Beijing (CN); Xiang Li, Beijing (CN); Yixin He, Beijing (CN); Liying Zhou, Beijing (CN); Yanan Liu, Beijing (CN)

(73) Assignee: BEIJING TIDE PHARMACEUTICAL CO., LTD., Beijing (CN)

( * ) Notice: Subject to any disclaimer, the term of this patent is extended or adjusted under 35 U.S.C. 154(b) by 0 days.

(21) Appl. No.: 16/644,977

(22) PCT Filed: Sep. 7, 2018

(86) PCT No.: PCT/CN2018/104552
§ 371 (c)(1),
(2) Date: Mar. 6, 2020

(87) PCT Pub. No.: WO2019/047914
PCT Pub. Date: Mar. 14, 2019

(65) Prior Publication Data
US 2020/0231967 A1    Jul. 23, 2020

(30) Foreign Application Priority Data

Sep. 7, 2017 (WO) ............... PCT/CN2017/100863
Sep. 7, 2017 (WO) ............... PCT/CN2017/100864
Sep. 7, 2017 (WO) ............... PCT/CN2017/100865
Sep. 7, 2017 (WO) ............... PCT/CN2017/100866
Sep. 7, 2017 (WO) ............... PCT/CN2017/100867

(51) Int. Cl.
| | |
|---|---|
| *C07H 21/04* | (2006.01) |
| *C12N 15/113* | (2010.01) |
| *A61P 19/02* | (2006.01) |
| *A61P 19/08* | (2006.01) |
| *A61P 29/00* | (2006.01) |
| *C12N 15/85* | (2006.01) |
| *A61K 48/00* | (2006.01) |

(52) U.S. Cl.
CPC ............ *C12N 15/113* (2013.01); *A61P 19/02* (2018.01); *A61P 19/08* (2018.01); *A61P 29/00* (2018.01); *C12N 15/85* (2013.01); *A61K 48/00* (2013.01); *C12N 2310/14* (2013.01); *C12N 2310/314* (2013.01); *C12N 2310/315* (2013.01); *C12N 2310/321* (2013.01); *C12N 2310/322* (2013.01); *C12N 2310/334* (2013.01); *C12N 2310/335* (2013.01)

(58) Field of Classification Search
None
See application file for complete search history.

(56) References Cited

U.S. PATENT DOCUMENTS

| | | | | |
|---|---|---|---|---|
| 7,691,997 | B2 * | 4/2010 | Khvorova | ............... A61P 35/02 536/24.5 |
| 7,750,144 | B2 * | 7/2010 | Zamore | ................... A61P 35/00 536/25.3 |
| 2007/0135372 | A1 * | 6/2007 | MacLachlan | ......... C12N 15/111 514/44 A |
| 2016/0272967 | A1 | 9/2016 | Zhang et al. | |

FOREIGN PATENT DOCUMENTS

| | | |
|---|---|---|
| EP | 2213738 | 8/2010 |
| EP | 3018209 | 5/2016 |
| WO | 2015027895 | 3/2015 |

OTHER PUBLICATIONS

This application is a National Stage Entry of, PCT/CN2018/104552, Sep. 7, 2018.
International Search Report of Int'l Appl. No. PCT/CN2018/104552, dated Dec. 5, 2018.
Chen et al. "MicroRNA-20a Promotes Osteogenic Differentiation of C3H/10T1/2 Cells through Regulating CKIP-1 Expression." Journal of Experimental Hematology. Feb. 2017;25(1):214-220. (abstract).
Guo et al. "Therapeutic RNA interference targeting CKIP-1 with a cross-species sequence to stimulate bone formation." Bone. Feb. 1, 2014;59:76-88.
Shaikh AB. "Role of CKIP-1 in suppression of osteoblast mediated bone repair in a collagen induced non-human primate arthritis model." Dec. 1, 2017, pp. 1-82.

* cited by examiner

*Primary Examiner* — Kimberly Chong
(74) *Attorney, Agent, or Firm* — Robin L. Teskin; Baker, Donelson, Bearman, Caldwell & Berkowitz PC

(57) ABSTRACT

The present invention relates to the field of biomedicine, particularly to double-stranded RNA molecules targeting CKIP-1 and uses thereof, particularly to use of the double-stranded RNA molecules for the treatment of inflammatory diseases such as arthritis, particularly rheumatoid arthritis.

20 Claims, 13 Drawing Sheets
Specification includes a Sequence Listing.

| siRNA | sense strand (5'-3') | antisense strand (5'-3') |
|---|---|---|
| si-TD029 | CGCCCGAGAAGGUCGGCUGTT | CAGCCGACCUUCUCGGGCGTT |
| si-TD030 | GCCCGAGAAGGUCGGCUGGTT | CCAGCCGACCUUCUCGGGCTT |
| si-TD031 | CCCGAGAAGGUCGGCUGGGTT | CCCAGCCGACCUUCUCGGGTT |
| si-TD032 | CCGAGAAGGUCGGCUGGGUTT | ACCCAGCCGACCUUCUCGGTT |
| si-TD033 | CGAGAAGGUCGGCUGGGUCTT | GACCCAGCCGACCUUCUCGTT |
| si-TD034 | GAGAAGGUCGGCUGGGUCCTT | GGACCCAGCCGACCUUCUCTT |
| si-TD035 | AGAAGGUCGGCUGGGUCCGTT | CGGACCCAGCCGACCUUCUTT |
| si-TD036 | GAAGGUCGGCUGGGUCCGGTT | CCGGACCCAGCCGACCUUCTT |
| si-TD037 | AAGGUCGGCUGGGUCCGGATT | UCCGGACCCAGCCGACCUUTT |
| si-TD038 | AGGUCGGCUGGGUCCGGAATT | UUCCGGACCCAGCCGACCUTT |
| si-TD040 | GUCGGCUGGGUCCGGAAAUTT | AUUUCCGGACCCAGCCGACTT |
| si-TD041 | UCGGCUGGGUCCGGAAAUUTT | AAUUUCCGGACCCAGCCGATT |
| si-TD042 | CGGCUGGGUCCGGAAAUUCTT | GAAUUUCCGGACCCAGCCGTT |
| si-TD043 | GGCUGGGUCCGGAAAUUCUTT | AGAAUUUCCGGACCCAGCCTT |
| si-TD044 | GCUGGGUCCGGAAAUUCUGTT | CAGAAUUUCCGGACCCAGCTT |
| si-TD045 | CUGGGUCCGGAAAUUCUGCTT | GCAGAAUUUCCGGACCCAGTT |
| si-TD046 | UGGGUCCGGAAAUUCUGCGTT | CGCAGAAUUUCCGGACCCATT |
| si-TD047 | GGGUCCGGAAAUUCUGCGGTT | CCGCAGAAUUUCCGGACCCTT |
| si-TD048 | GGUCCGGAAAUUCUGCGGGTT | CCCGCAGAAUUUCCGGACCTT |
| si-TD049 | GUCCGGAAAUUCUGCGGGATT | UCCCGCAGAAUUUCCGGACTT |
| si-TD050 | UCCGGAAAUUCUGCGGGAATT | UUCCCGCAGAAUUUCCGGATT |
| si-TD052 | CGGAAAUUCUGCGGGAAAGTT | CUUUCCCGCAGAAUUUCCGTT |
| si-TD053 | GGAAAUUCUGCGGGAAAGGTT | CCUUUCCCGCAGAAUUUCCTT |
| si-TD054 | GAAAUUCUGCGGGAAAGGGTT | CCCUUUCCCGCAGAAUUUCTT |
| si-TD055 | AAAUUCUGCGGGAAAGGGATT | UCCCUUUCCCGCAGAAUUUTT |
| si-TD056 | AAUUCUGCGGGAAAGGGAUTT | AUCCCUUUCCCGCAGAAUUTT |
| si-TD057 | AUUCUGCGGGAAAGGGAUUTT | AAUCCCUUUCCCGCAGAAUTT |
| si-TD058 | UUCUGCGGGAAAGGGAUUUTT | AAAUCCCUUUCCCGCAGAATT |
| si-TD059 | UCUGCGGGAAAGGGAUUUUTT | AAAAUCCCUUUCCCGCAGATT |
| si-TD060 | CUGCGGGAAAGGGAUUUUCTT | GAAAAUCCCUUUCCCGCAGTT |
| si-TD061 | UGCGGGAAAGGGAUUUUCATT | UGAAAAUCCCUUUCCCGCATT |
| si-TD062 | GCGGGAAAGGGAUUUUCAGTT | CUGAAAAUCCCUUUCCCGCTT |
| si-TD063 | CGGGAAAGGGAUUUUCAGGTT | CCUGAAAAUCCCUUUCCCGTT |
| si-TD064 | GGGAAAGGGAUUUUCAGGGTT | CCCUGAAAAUCCCUUUCCCTT |
| si-TD065 | GGAAAGGGAUUUUCAGGGATT | UCCCUGAAAAUCCCUUUCCTT |
| si-TD066 | GAAAGGGAUUUUCAGGGAGTT | CUCCCUGAAAAUCCCUUUCTT |
| si-TD067 | AAAGGGAUUUUCAGGGAGATT | UCUCCCUGAAAAUCCCUUUTT |
| si-TD068 | AAGGGAUUUUCAGGGAGAUTT | AUCUCCCUGAAAAUCCCUUTT |
| si-TD069 | AGGGAUUUUCAGGGAGAUUTT | AAUCUCCCUGAAAAUCCCUTT |
| si-TD070 | GGGAUUUUCAGGGAGAUUUTT | AAAUCUCCCUGAAAAUCCCTT |
| si-TD071 | GGAUUUUCAGGGAGAUUUGTT | CAAAUCUCCCUGAAAAUCCTT |
| si-TD072 | GAUUUUCAGGGAGAUUUGGTT | CCAAAUCUCCCUGAAAAUCTT |
| si-TD073 | AUUUUCAGGGAGAUUUGGATT | UCCAAAUCUCCCUGAAAAUTT |
| si-TD074 | UUUUCAGGGAGAUUUGGAATT | UUCCAAAUCUCCCUGAAAATT |

FIG. 1

| | | |
|---|---|---|
| si-TD075 | UUUCAGGGAGAUUUGGAAAUU | UUUCCAAAUCUCCCUGAAAUU |
| si-TD076 | UUCAGGGAGAUUUGGAAAAUU | UUUUCCAAAUCUCCCUGAAUU |
| si-TD077 | UCAGGGAGAUUUGGAAAAAUU | UUUUUCCAAAUCUCCCUGAUU |
| si-TD078 | CAGGGAGAUUUGGAAAAACUU | GUUUUUCCAAAUCUCCCUGUU |
| si-TD079 | AGGGAGAUUUGGAAAAACCUU | GGUUUUUCCAAAUCUCCCUUU |
| si-TD080 | GGGAGAUUUGGAAAAACCGUU | CGGUUUUUCCAAAUCUCCCUU |
| si-TD081 | GGAGAUUUGGAAAAACCGCUU | GCGGUUUUUCCAAAUCUCCUU |
| si-TD082 | GAGAUUUGGAAAAACCGCUUU | AGCGGUUUUUCCAAAUCUCUU |
| si-TD083 | AGAUUUGGAAAAACCGCUAUU | UAGCGGUUUUUCCAAAUCUUU |
| si-TD084 | GAUUUGGAAAAACCGCUAUUU | AUAGCGGUUUUUCCAAAUCUU |
| si-TD085 | AUUUGGAAAAACCGCUAUGUU | CAUAGCGGUUUUUCCAAAUUU |
| si-TD086 | UUUGGAAAAACCGCUAUGUUU | ACAUAGCGGUUUUUCCAAAUU |
| si-TD087 | UUGGAAAAACCGCUAUGUGUU | CACAUAGCGGUUUUUCCAAUU |
| si-TD088 | UGGAAAAACCGCUAUGUGGUU | CCACAUAGCGGUUUUUCCAUU |
| si-TD089 | GGAAAAACCGCUAUGUGGUUU | ACCACAUAGCGGUUUUUCCUU |
| si-TD090 | GAAAAACCGCUAUGUGGUGUU | CACCACAUAGCGGUUUUUCUU |
| si-TD091 | AAAAACCGCUAUGUGGUGCUU | GCACCACAUAGCGGUUUUUUU |
| si-TD092 | AAAACCGCUAUGUGGUGCUUU | AGCACCACAUAGCGGUUUUUU |
| si-TD093 | AAACCGCUAUGUGGUGCUGUU | CAGCACCACAUAGCGGUUUUU |
| si-TD094 | AACCGCUAUGUGGUGCUGAUU | UCAGCACCACAUAGCGGUUUU |
| si-TD096 | CCGCUAUGUGGUGCUGAAAUU | UUUCAGCACCACAUAGCGGUU |
| si-TD097 | CGCUAUGUGGUGCUGAAAGUU | CUUUCAGCACCACAUAGCGUU |
| si-TD098 | GCUAUGUGGUGCUGAAAGGUU | CCUUUCAGCACCACAUAGCUU |
| si-TD136 | GAGAAGGAGGUAAAAGAUGUU | CAUCUUUUACCUCCUUCUCUU |
| si-TD137 | AGAAGGAGGUAAAAGAUGAUU | UCAUCUUUUACCUCCUUCUUU |
| si-TD138 | GAAGGAGGUAAAAGAUGAGUU | CUCAUCUUUUACCUCCUUCUU |
| si-TD139 | AAGGAGGUAAAAGAUGAGAUU | UCUCAUCUUUUACCUCCUUUU |
| si-TD140 | AGGAGGUAAAAGAUGAGAAUU | UUCUCAUCUUUUACCUCCUUU |
| si-TD141 | GGAGGUAAAAGAUGAGAAAUU | UUUCUCAUCUUUUACCUCCUU |
| si-TD142 | GAGGUAAAAGAUGAGAAAAUU | UUUUCUCAUCUUUUACCUCUU |
| si-TD143 | AGGUAAAAGAUGAGAAAAAUU | UUUUUCUCAUCUUUUACCUUU |
| si-TD182 | UGAGUGACUAUGAGAAGUGUU | CACUUCUCAUAGUCACUCAUU |
| si-TD181 | CUGAGUGACUAUGAGAAGUUU | ACUUCUCAUAGUCACUCAGUU |
| si-TD179 | ACCUGAGUGACUAUGAGAAUU | UUCUCAUAGUCACUCAGGUUU |
| si-TD178 | GACCUGAGUGACUAUGAGAUU | UCUCAUAGUCACUCAGGUCUU |
| si-TD177 | UGACCUGAGUGACUAUGAGUU | CUCAUAGUCACUCAGGUCAUU |
| si-TD176 | UUGACCUGAGUGACUAUGAUU | UCAUAGUCACUCAGGUCAAUU |
| si-TD175 | UUUGACCUGAGUGACUAUGUU | CAUAGUCACUCAGGUCAAAUU |
| si-TD224 | GCAGGAGCAAGAAAAAUCAUU | UGAUUUUCUUGCUCCUGCUU |
| si-TD223 | AGCAGGAGCAAGAAAAAUCUU | GAUUUUCUUGCUCCUGCUUU |
| si-TD222 | GAGCAGGAGCAAGAAAAAUUU | AUUUUUCUUGCUCCUGCUCUU |
| si-TD221 | AGAGCAGGAGCAAGAAAAAUU | UUUUUCUUGCUCCUGCUCUUU |
| si-TD220 | AAGAGCAGGAGCAAGAAAAUU | UUUUCUUGCUCCUGCUCUUUU |
| si-TD219 | CAAGAGCAGGAGCAAGAAAUU | UUUCUUGCUCCUGCUCUUGUU |
| si-TD218 | CCAAGAGCAGGAGCAAGAAUU | UUCUUGCUCCUGCUCUUGGUU |

FIG. 1 (continued)

| | | |
|---|---|---|
| si-TD217 | UCCAAGAGCAGGAGCAAGATT | UCUUGCUCCUGCUCUUGGATT |
| si-TD385 | AGGACAGCUAUCUUGCCCATT | UGGGCAAGAUAGCUGUCCUTT |
| si-TD384 | GAGGACAGCUAUCUUGCCCTT | GGGCAAGAUAGCUGUCCUCTT |
| si-TD383 | GGAGGACAGCUAUCUUGCCTT | GGCAAGAUAGCUGUCCUCCTT |
| si-TD382 | AGGAGGACAGCUAUCUUGCTT | GCAAGAUAGCUGUCCUCCUTT |
| si-TD381 | GAGGAGGACAGCUAUCUUGTT | CAAGAUAGCUGUCCUCCUCTT |
| si-TD380 | UGAGGAGGACAGCUAUCUUTT | AAGAUAGCUGUCCUCCUCATT |
| si-TD379 | UUGAGGAGGACAGCUAUCUTT | AGAUAGCUGUCCUCCUCAATT |
| si-TD378 | GUUGAGGAGGACAGCUAUCTT | GAUAGCUGUCCUCCUCAACTT |
| si-TD377 | CGUUGAGGAGGACAGCUAUTT | AUAGCUGUCCUCCUCAACGTT |
| si-TD376 | CCGUUGAGGAGGACAGCUATT | UAGCUGUCCUCCUCAACGGTT |
| si-TD375 | ACCGUUGAGGAGGACAGCUTT | AGCUGUCCUCCUCAACGGUTT |
| si-TD374 | CACCGUUGAGGAGGACAGCTT | GCUGUCCUCCUCAACGGUGTT |
| si-TD373 | UCACCGUUGAGGAGGACAGTT | CUGUCCUCCUCAACGGUGATT |
| si-TD372 | GUCACCGUUGAGGAGGACATT | UGUCCUCCUCAACGGUGACTT |
| si-TD371 | GGUCACCGUUGAGGAGGACTT | GUCCUCCUCAACGGUGACCTT |
| si-TD370 | AGGUCACCGUUGAGGAGGATT | UCCUCCUCAACGGUGACCUTT |
| si-TD369 | GAGGUCACCGUUGAGGAGGTT | CCUCCUCAACGGUGACCUCTT |
| si-TD368 | UGAGGUCACCGUUGAGGAGTT | CUCCUCAACGGUGACCUCATT |
| si-TD367 | AUGAGGUCACCGUUGAGGATT | UCCUCAACGGUGACCUCAUTT |
| si-TD366 | GAUGAGGUCACCGUUGAGGTT | CCUCAACGGUGACCUCAUCTT |
| si-TD364 | UGGAUGAGGUCACCGUUGATT | UCAACGGUGACCUCAUCCATT |
| si-TD363 | UUGGAUGAGGUCACCGUUGTT | CAACGGUGACCUCAUCCAATT |
| si-TD362 | CUUGGAUGAGGUCACCGUUTT | AACGGUGACCUCAUCCAAGTT |
| si-TD361 | UCUUGGAUGAGGUCACCGUTT | ACGGUGACCUCAUCCAAGATT |
| si-TD360 | AUCUUGGAUGAGGUCACCGTT | CGGUGACCUCAUCCAAGAUTT |
| si-TD359 | UAUCUUGGAUGAGGUCACCTT | GGUGACCUCAUCCAAGAUATT |
| si-TD358 | GUAUCUUGGAUGAGGUCACTT | GUGACCUCAUCCAAGAUACTT |
| si-TD357 | CGUAUCUUGGAUGAGGUCATT | UGACCUCAUCCAAGAUACGTT |
| si-TD356 | CCGUAUCUUGGAUGAGGUCTT | GACCUCAUCCAAGAUACGGTT |
| si-TD355 | ACCGUAUCUUGGAUGAGGUTT | ACCUCAUCCAAGAUACGGUTT |
| si-TD354 | AACCGUAUCUUGGAUGAGGTT | CCUCAUCCAAGAUACGGUUTT |
| si-TD454 | AAGACCCUUCCCCUGAGGATT | UCCUCAGGGGAAGGGUCUUTT |
| si-TD453 | GAAGACCCUUCCCCUGAGGTT | CCUCAGGGGAAGGGUCUUCTT |
| si-TD452 | GGAAGACCCUUCCCCUGAGTT | CUCAGGGGAAGGGUCUUCCTT |
| si-TD451 | AGGAAGACCCUUCCCCUGATT | UCAGGGGAAGGGUCUUCCUTT |
| si-TD450 | GAGGAAGACCCUUCCCCUGTT | CAGGGGAAGGGUCUUCCUCTT |
| si-TD449 | AGAGGAAGACCCUUCCCCUTT | AGGGGAAGGGUCUUCCUCUTT |
| si-TD448 | AAGAGGAAGACCCUUCCCCTT | GGGGAAGGGUCUUCCUCUUTT |
| si-TD447 | CAAGAGGAAGACCCUUCCCTT | GGGAAGGGUCUUCCUCUUGTT |
| si-TD446 | CCAAGAGGAAGACCCUUCCTT | GGAAGGGUCUUCCUCUUGGTT |
| si-TD445 | UCCAAGAGGAAGACCCUUCTT | GAAGGGUCUUCCUCUUGGATT |
| si-TD444 | AUCCAAGAGGAAGACCCUUTT | AAGGGUCUUCCUCUUGGAUTT |
| si-TD443 | GAUCCAAGAGGAAGACCCUTT | AGGGUCUUCCUCUUGGAUCTT |
| si-TD442 | UGAUCCAAGAGGAAGACCCTT | GGGUCUUCCUCUUGGAUCATT |

FIG. 1 (continued)

| | | |
|---|---|---|
| si-TD509 | GGACAAGUCUGUGGCCCAGTT | CUGGGCCACAGACUUGUCCTT |
| si-TD508 | UGGACAAGUCUGUGGCCCATT | UGGGCCACAGACUUGUCCATT |
| si-TD507 | CUGGACAAGUCUGUGGCCCTT | GGGCCACAGACUUGUCCAGTT |
| si-TD577 | GCCUCCCUGGAGGAGAUCCTT | GGAUCUCCUCCAGGGAGGCTT |
| si-TD578 | CCUCCCUGGAGGAGAUCCUTT | AGGAUCUCCUCCAGGGAGGTT |
| si-TD611 | GGUAGCAAGGAAACUGGAGTT | CUCCAGUUUCCUUGCUACCTT |
| si-TD610 | UGGUAGCAAGGAAACUGGATT | UCCAGUUUCCUUGCUACCATT |
| si-TD609 | CUGGUAGCAAGGAAACUGGTT | CCAGUUUCCUUGCUACCAGTT |
| si-TD608 | CCUGGUAGCAAGGAAACUGTT | CAGUUUCCUUGCUACCAGGTT |
| si-TD607 | ACCUGGUAGCAAGGAAACUTT | AGUUUCCUUGCUACCAGGUTT |
| si-TD606 | GACCUGGUAGCAAGGAAACTT | GUUUCCUUGCUACCAGGUCTT |
| si-TD604 | AGGACCUGGUAGCAAGGAATT | UUCCUUGCUACCAGGUCCUTT |
| si-TD603 | CAGGACCUGGUAGCAAGGATT | UCCUUGCUACCAGGUCCUGTT |
| si-TD602 | CCAGGACCUGGUAGCAAGGTT | CCUUGCUACCAGGUCCUGGTT |
| si-TD601 | UCCAGGACCUGGUAGCAAGTT | CUUGCUACCAGGUCCUGGATT |
| si-TD600 | AUCCAGGACCUGGUAGCAATT | UUGCUACCAGGUCCUGGAUTT |
| si-TD599 | GAUCCAGGACCUGGUAGCATT | UGCUACCAGGUCCUGGAUCTT |
| si-TD598 | GGAUCCAGGACCUGGUAGCTT | GCUACCAGGUCCUGGAUCCTT |
| si-TD597 | CGGAUCCAGGACCUGGUAGTT | CUACCAGGUCCUGGAUCCGTT |
| si-TD596 | CCGGAUCCAGGACCUGGUATT | UACCAGGUCCUGGAUCCGGTT |
| si-TD595 | CCCGGAUCCAGGACCUGGUTT | ACCAGGUCCUGGAUCCGGGTT |
| si-TD594 | UCCCGGAUCCAGGACCUGGTT | CCAGGUCCUGGAUCCGGGATT |
| si-TD593 | GUCCCGGAUCCAGGACCUGTT | CAGGUCCUGGAUCCGGGACTT |
| si-TD592 | UGUCCCGGAUCCAGGACCUTT | AGGUCCUGGAUCCGGGACATT |
| si-TD591 | CUGUCCCGGAUCCAGGACCTT | GGUCCUGGAUCCGGGACAGTT |
| si-TD590 | GCUGUCCCGGAUCCAGGACTT | GUCCUGGAUCCGGGACAGCTT |
| si-TD589 | AGCUGUCCCGGAUCCAGGATT | UCCUGGAUCCGGGACAGCUTT |
| si-TD588 | CAGCUGUCCCGGAUCCAGGTT | CCUGGAUCCGGGACAGCUGTT |
| si-TD587 | GCAGCUGUCCCGGAUCCAGTT | CUGGAUCCGGGACAGCUGCTT |
| si-TD586 | GGCAGCUGUCCCGGAUCCATT | UGGAUCCGGGACAGCUGCCTT |
| si-TD585 | GGGCAGCUGUCCCGGAUCCTT | GGAUCCGGGACAGCUGCCCTT |
| si-TD721 | AGCUGAGAGACCUGUACAGTT | CUGUACAGGUCUCUCAGCUTT |
| si-TD720 | GAGCUGAGAGACCUGUACATT | UGUACAGGUCUCUCAGCUCTT |
| si-TD719 | GGAGCUGAGAGACCUGUACTT | GUACAGGUCUCUCAGCUCCTT |
| si-TD718 | GGGAGCUGAGAGACCUGUATT | UACAGGUCUCUCAGCUCCCTT |
| si-TD742 | AGAUGGACCUGCAGACCCCTT | GGGGUCUGCAGGUCCAUCUTT |
| si-TD741 | CAGAUGGACCUGCAGACCCTT | GGGUCUGCAGGUCCAUCGTT |
| si-TD744 | ACUCCACCUCAGACAGACTT | GUCUGUCGAGGUGGGAGUTT |
| si-TD743 | GACUCCCACCUCAGACAGATT | UCUGUCUGAGGUGGGAGUCTT |
| si-TD144 | GGUAAAGAUGAGAAAAAUTT | AUUUUUCUCAUCUUUUACCTT |
| si-TD145 | GUAAAAGAUGAGAAAAAUATT | UAUUUUUCUCAUCUUUUACTT |
| si-TD479 | CUCUUGUGCUGAGAGCUUUTT | AAAGCUCUCAGCACAAGAGTT |
| si-TD480 | UCUUGUGCUGAGAGCUUUCTT | GAAAGCUCUCAGCACAAGATT |
| si-TD481 | CUUGUGCUGAGAGCUUUCGTT | CGAAAGCUCUCAGCACAAGTT |
| si-TD482 | UUGUGCUGAGAGCUUUCGGTT | CCGAAAGCUCUCAGCACAATT |

FIG. 1 (continued)

| | | |
|---|---|---|
| si-TD483 | UGUGCUGAGAGCUUUCGGGTT | CCCGAAAGCUCUCAGCACATT |
| si-TD584 | GGGGCAGCUGUCCGGAUCTT | GAUCCGGGACAGCUGCCCCTT |
| si-TD583 | CGGGGCAGCUGUCCCGGAUTT | AUCCGGGACAGCUGCCCCGTT |
| si-TD582 | CCGGGGCAGCUGUCCCGGATT | UCCGGGACAGCUGCCCCGGTT |
| si-TD740 | ACAGAUGGACCUGCAGACCTT | GGUCUGCAGGUCCAUCUGUTT |
| si-TD739 | GACAGAUGGACCUGCAGACTT | GUCUGCAGGUCCAUCUGUCTT |
| si-TD738 | AGACAGAUGGACCUGCAGATT | UCUGCAGGUCCAUCUGUCUTT |
| si-TD737 | CAGACAGAUGGACCUGCAGTT | CUGCAGGUCCAUCUGUCUGTT |
| si-TD736 | ACAGACAGAUGGACCUGCATT | UGCAGGUCCAUCUGUCUGUTT |
| si-TD735 | UACAGACAGAUGGACCUGCTT | GCAGGUCCAUCUGUCUGUATT |
| si-TD734 | GUACAGACAGAUGGACCUGTT | CAGGUCCAUCUGUCUGUACTT |
| si-TD733 | UGUACAGACAGAUGGACCUTT | AGGUCCAUCUGUCUGUACATT |
| si-TD732 | CUGUACAGACAGAUGGACCTT | GGUCCAUCUGUCUGUACAGTT |
| si-TD731 | CCUGUACAGACAGAUGGACTT | GUCCAUCUGUCUGUACAGGTT |
| si-TD730 | ACCUGUACAGACAGAUGGATT | UCCAUCUGUCUGUACAGGUTT |
| si-TD729 | GACCUGUACAGACAGAUGGTT | CCAUCUGUCUGUACAGGUCTT |
| si-TD728 | AGACCUGUACAGACAGAUGTT | CAUCUGUCUGUACAGGUCUTT |
| si-TD727 | GAGACCUGUACAGACAGAUTT | AUCUGUCUGUACAGGUCUCTT |
| si-TD726 | AGAGACCUGUACAGACAGATT | UCUGUCUGUACAGGUCUCUTT |
| si-TD725 | GAGAGACCUGUACAGACAGTT | CUGUCUGUACAGGUCUCUCTT |
| si-TD723 | CUGAGAGACCUGUACAGACTT | GUCUGUACAGGUCUCUCAGTT |
| si-TD722 | GCUGAGAGACCUGUACAGATT | UCUGUACAGGUCUCUCAGCTT |
| si-TD717 | AGGGAGCUGAGAGACCUGUTT | ACAGGUCUCUCAGCUCCCUTT |
| si-TD716 | CAGGGAGCUGAGAGACCUGTT | CAGGUCUCUCAGCUCCCUGTT |
| si-TD715 | UCAGGGAGCUGAGAGACCUTT | AGGUCUCUCAGCUCCCUGATT |
| si-TD714 | GUCAGGGAGCUGAGAGACCTT | GGUCUCUCAGCUCCCUGACTT |
| si-7 | UGGGAGAUGGGAAGCGAAATT | UUUCGCUUCCCAUCUCCCATT |
| si-10 | CAGACAAAGGGGCCACCUATT | UAGGUGGCCCCUUUGUCUGTT |
| si-1 | GGACCUGGUAGCAAGGAAATT | UUUCCUUGCUACCAGGUCCTT |
| NC-1 | GAAAGAUAGAGAAGGUAGATT | UCUACCUUCUCUAUCUUUCTT |
| NC-2 | GCAACAGCCGAUGAAGUUATT | UAACUUCAUCGGCUGUUGCTT |
| NC-3 | GGCCGAGCAACGAAUGUCATT | UGACAUUCGUUGCUCGGCCTT |
| NC-4 | GGACAUCGAACGAAGUGCUTT | AGCACUUCGUUCGAUGUCCTT |
| NC-5 | GCGGUCCCUGCGACGUACATT | UGUACGUCGCAGGGACCGCTT |
| NC-6 | GCUGCGCGAACCCAUCAAATT | UUUGAUGGGUUCGCGCAGCTT |
| NC-7 | UUCUCCGAACGUGUCACGUTT | ACGUGACACGUUCGGAGAATT |
| NC-8 | GCGACGAUCUGCCUAAGAUTT | AUCUUAGGCAGAUCGUCGCTT |

FIG. 1 (continued)

SEQUENCE LISTING

```
<160> NUMBER OF SEQ ID NOS: 192

<210> SEQ ID NO 1
<211> LENGTH: 19
<212> TYPE: RNA
<213> ORGANISM: Artificial Sequence
<220> FEATURE:
<223> OTHER INFORMATION: si-TD037 sense

<400> SEQUENCE: 1
aaggucggcu ggguccgga                                              19

<210> SEQ ID NO 2
<211> LENGTH: 19
```

```
<212> TYPE: RNA
<213> ORGANISM: Artificial Sequence
<220> FEATURE:
<223> OTHER INFORMATION: si-TD037 antisense

<400> SEQUENCE: 2
uccggaccca gccgaccuu                                                  19

<210> SEQ ID NO 3
<211> LENGTH: 19
<212> TYPE: RNA
<213> ORGANISM: Artificial Sequence
<220> FEATURE:
<223> OTHER INFORMATION: si-TD040 sense

<400> SEQUENCE: 3
gucggcuggg uccggaaau                                                  19

<210> SEQ ID NO 4
<211> LENGTH: 19
<212> TYPE: RNA
<213> ORGANISM: Artificial Sequence
<220> FEATURE:
<223> OTHER INFORMATION: si-TD040 antisense

<400> SEQUENCE: 4
auuuccggac ccagccgac                                                  19

<210> SEQ ID NO 5
<211> LENGTH: 19
<212> TYPE: RNA
<213> ORGANISM: Artificial Sequence
<220> FEATURE:
<223> OTHER INFORMATION: si-TD042 sense

<400> SEQUENCE: 5
cggcuggguc cggaaauuc                                                  19

<210> SEQ ID NO 6
<211> LENGTH: 19
<212> TYPE: RNA
<213> ORGANISM: Artificial Sequence
<220> FEATURE:
<223> OTHER INFORMATION: si-TD042 antisense

<400> SEQUENCE: 6
gaauuuccgg acccagccg                                                  19

<210> SEQ ID NO 7
<211> LENGTH: 19
<212> TYPE: RNA
<213> ORGANISM: Artificial Sequence
<220> FEATURE:
<223> OTHER INFORMATION: si-TD044 sense

<400> SEQUENCE: 7
gcuggguccg gaaauucug                                                  19

<210> SEQ ID NO 8
<211> LENGTH: 19
<212> TYPE: RNA
<213> ORGANISM: Artificial Sequence
<220> FEATURE:
<223> OTHER INFORMATION: si-TD044 antisense

<400> SEQUENCE: 8
```
cagaauuucc ggacccagc                                            19

<210> SEQ ID NO 9
<211> LENGTH: 19
<212> TYPE: RNA
<213> ORGANISM: Artificial Sequence
<220> FEATURE:
<223> OTHER INFORMATION: si-TD050 sense

<400> SEQUENCE: 9
uccggaaauu cugcgggaa                                            19

<210> SEQ ID NO 10
<211> LENGTH: 19
<212> TYPE: RNA
<213> ORGANISM: Artificial Sequence
<220> FEATURE:
<223> OTHER INFORMATION: si-TD050 antisense

<400> SEQUENCE: 10
uucccgcaga auuccgga                                             19

<210> SEQ ID NO 11
<211> LENGTH: 19
<212> TYPE: RNA
<213> ORGANISM: Artificial Sequence
<220> FEATURE:
<223> OTHER INFORMATION: si-TD057 sense

<400> SEQUENCE: 11
auucugcggg aaagggauu                                            19

<210> SEQ ID NO 12
<211> LENGTH: 19
<212> TYPE: RNA
<213> ORGANISM: Artificial Sequence
<220> FEATURE:
<223> OTHER INFORMATION: si-TD057 antisense

<400> SEQUENCE: 12
aaucccuuuc ccgcagaau                                            19

<210> SEQ ID NO 13
<211> LENGTH: 19
<212> TYPE: RNA
<213> ORGANISM: Artificial Sequence
<220> FEATURE:
<223> OTHER INFORMATION: si-TD058 sense

<400> SEQUENCE: 13
uucugcggga aagggauuu                                            19

<210> SEQ ID NO 14
<211> LENGTH: 19
<212> TYPE: RNA
<213> ORGANISM: Artificial Sequence
<220> FEATURE:
<223> OTHER INFORMATION: si-TD058 antisense

<400> SEQUENCE: 14
aaaucccuuu cccgcagaa                                            19

<210> SEQ ID NO 15
<211> LENGTH: 19
<212> TYPE: RNA
<213> ORGANISM: Artificial Sequence

```
<220> FEATURE:
<223> OTHER INFORMATION: si-TD060 sense

<400> SEQUENCE: 15
cugcgggaaa gggauuuuc                                             19

<210> SEQ ID NO 16
<211> LENGTH: 19
<212> TYPE: RNA
<213> ORGANISM: Artificial Sequence
<220> FEATURE:
<223> OTHER INFORMATION: si-TD060 antisense

<400> SEQUENCE: 16
gaaaaucccu uucccgcag                                             19

<210> SEQ ID NO 17
<211> LENGTH: 19
<212> TYPE: RNA
<213> ORGANISM: Artificial Sequence
<220> FEATURE:
<223> OTHER INFORMATION: si-TD061 sense

<400> SEQUENCE: 17
ugcgggaaag ggauuuuca                                             19

<210> SEQ ID NO 18
<211> LENGTH: 19
<212> TYPE: RNA
<213> ORGANISM: Artificial Sequence
<220> FEATURE:
<223> OTHER INFORMATION: si-TD061 antisense

<400> SEQUENCE: 18 ugaaaaucccc uuucccgca                                            19

<210> SEQ ID NO 19
<211> LENGTH: 19
<212> TYPE: RNA
<213> ORGANISM: Artificial Sequence
<220> FEATURE:
<223> OTHER INFORMATION: si-TD062 sense

<400> SEQUENCE: 19
gcgggaaagg gauuuucag                                             19

<210> SEQ ID NO 20
<211> LENGTH: 19
<212> TYPE: RNA
<213> ORGANISM: Artificial Sequence
<220> FEATURE:
<223> OTHER INFORMATION: si-TD062 antisense

<400> SEQUENCE: 20
cugaaaaucc cuuucccgc                                             19

<210> SEQ ID NO 21
<211> LENGTH: 19
<212> TYPE: RNA
<213> ORGANISM: Artificial Sequence
<220> FEATURE:
<223> OTHER INFORMATION: si-TD064 sense

<400> SEQUENCE: 21
gggaaaggga uuuucaggg                                             19
```

```
<210> SEQ ID NO 22
<211> LENGTH: 19
<212> TYPE: RNA
<213> ORGANISM: Artificial Sequence
<220> FEATURE:
<223> OTHER INFORMATION: si-TD064 antisense

<400> SEQUENCE: 22
cccugaaaau cccuuccc                                                    19

<210> SEQ ID NO 23
<211> LENGTH: 19
<212> TYPE: RNA
<213> ORGANISM: Artificial Sequence
<220> FEATURE:
<223> OTHER INFORMATION: si-TD065 sense

<400> SEQUENCE: 23
ggaaagggau uuucaggga                                                   19

<210> SEQ ID NO 24
<211> LENGTH: 19
<212> TYPE: RNA
<213> ORGANISM: Artificial Sequence
<220> FEATURE:
<223> OTHER INFORMATION: si-TD065 antisense

<400> SEQUENCE: 24
ucccugaaaa ucccuucc                                                    19

<210> SEQ ID NO 25
<211> LENGTH: 19
<212> TYPE: RNA
<213> ORGANISM: Artificial Sequence
<220> FEATURE:
<223> OTHER INFORMATION: si-TD066 sense

<400> SEQUENCE: 25
gaaagggauu uucaggag                                                    19

<210> SEQ ID NO 26
<211> LENGTH: 19
<212> TYPE: RNA
<213> ORGANISM: Artificial Sequence
<220> FEATURE:
<223> OTHER INFORMATION: si-TD066 antisense

<400> SEQUENCE: 26
cucccugaaa aucccuuuc                                                   19

<210> SEQ ID NO 27
<211> LENGTH: 19
<212> TYPE: RNA
<213> ORGANISM: Artificial Sequence
<220> FEATURE:
<223> OTHER INFORMATION: si-TD067 sense

<400> SEQUENCE: 27
aaagggauuu ucaggaga                                                    19

<210> SEQ ID NO 28
<211> LENGTH: 19
<212> TYPE: RNA
<213> ORGANISM: Artificial Sequence
<220> FEATURE:
<223> OTHER INFORMATION: si-TD067 antisense
```

```
<400> SEQUENCE: 28
ucucccugaa aaucccuuu                                                    19

<210> SEQ ID NO 29
<211> LENGTH: 19
<212> TYPE: RNA
<213> ORGANISM: Artificial Sequence
<220> FEATURE:
<223> OTHER INFORMATION: si-TD068 sense

<400> SEQUENCE: 29
aagggauuuu cagggagau                                                    19

<210> SEQ ID NO 30
<211> LENGTH: 19
<212> TYPE: RNA
<213> ORGANISM: Artificial Sequence
<220> FEATURE:
<223> OTHER INFORMATION: si-TD068 antisense

<400> SEQUENCE: 30
aucucccuga aaaucccuu                                                    19

<210> SEQ ID NO 31
<211> LENGTH: 19
<212> TYPE: RNA
<213> ORGANISM: Artificial Sequence
<220> FEATURE:
<223> OTHER INFORMATION: si-TD070 sense

<400> SEQUENCE: 31
gggauuuuca gggagauuu                                                    19

<210> SEQ ID NO 32
<211> LENGTH: 19
<212> TYPE: RNA
<213> ORGANISM: Artificial Sequence
<220> FEATURE:
<223> OTHER INFORMATION: si-TD070 antisense

<400> SEQUENCE: 32
aaaucucccu gaaaauccc                                                    19

<210> SEQ ID NO 33
<211> LENGTH: 19
<212> TYPE: RNA
<213> ORGANISM: Artificial Sequence
<220> FEATURE:
<223> OTHER INFORMATION: si-TD072 sense

<400> SEQUENCE: 33 gauuucagg gagauuugg                                                     19

<210> SEQ ID NO 34
<211> LENGTH: 19
<212> TYPE: RNA
<213> ORGANISM: Artificial Sequence
<220> FEATURE:
<223> OTHER INFORMATION: si-TD072 antisense

<400> SEQUENCE: 34
ccaaaucucc cugaaaauc                                                    19

<210> SEQ ID NO 35
```

```
<211> LENGTH: 19
<212> TYPE: RNA
<213> ORGANISM: Artificial Sequence
<220> FEATURE:
<223> OTHER INFORMATION: si-TD074 sense

<400> SEQUENCE: 35
uuuucaggga gauuuggaa                                            19

<210> SEQ ID NO 36
<211> LENGTH: 19
<212> TYPE: RNA
<213> ORGANISM: Artificial Sequence
<220> FEATURE:
<223> OTHER INFORMATION: si-TD074 antisense

<400> SEQUENCE: 36
uuccaaaucu cccugaaaa                                            19

<210> SEQ ID NO 37
<211> LENGTH: 19
<212> TYPE: RNA
<213> ORGANISM: Artificial Sequence
<220> FEATURE:
<223> OTHER INFORMATION: si-TD076 sense

<400> SEQUENCE: 37
uucagggaga uuuggaaaa                                            19

<210> SEQ ID NO 38
<211> LENGTH: 19
<212> TYPE: RNA
<213> ORGANISM: Artificial Sequence
<220> FEATURE:
<223> OTHER INFORMATION: si-TD076 antisense

<400> SEQUENCE: 38
uuuuccaaau cucccugaa                                            19

<210> SEQ ID NO 39
<211> LENGTH: 19
<212> TYPE: RNA
<213> ORGANISM: Artificial Sequence
<220> FEATURE:
<223> OTHER INFORMATION: si-TD078 sense

<400> SEQUENCE: 39
cagggagauu uggaaaaac                                            19

<210> SEQ ID NO 40
<211> LENGTH: 19
<212> TYPE: RNA
<213> ORGANISM: Artificial Sequence
<220> FEATURE:
<223> OTHER INFORMATION: si-TD078 antisense

<400> SEQUENCE: 40
guuuuuccaa aucucccug                                            19

<210> SEQ ID NO 41
<211> LENGTH: 19
<212> TYPE: RNA
<213> ORGANISM: Artificial Sequence
<220> FEATURE:
<223> OTHER INFORMATION: si-TD080 sense

<400> SEQUENCE: 41
```

```
gggagauuug gaaaaaccg                                                 19

<210> SEQ ID NO 42
<211> LENGTH: 19
<212> TYPE: RNA
<213> ORGANISM: Artificial Sequence
<220> FEATURE:
<223> OTHER INFORMATION: si-TD080 antisense

<400> SEQUENCE: 42
cgguuuuucc aaaucuccc                                                 19

<210> SEQ ID NO 43
<211> LENGTH: 19
<212> TYPE: RNA
<213> ORGANISM: Artificial Sequence
<220> FEATURE:
<223> OTHER INFORMATION: si-TD082 sense

<400> SEQUENCE: 43
gagauuugga aaaccgcu                                                  19

<210> SEQ ID NO 44
<211> LENGTH: 19
<212> TYPE: RNA
<213> ORGANISM: Artificial Sequence
<220> FEATURE:
<223> OTHER INFORMATION: si-TD082 antisense

<400> SEQUENCE: 44
agcgguuuuu ccaaaucuc                                                 19

<210> SEQ ID NO 45
<211> LENGTH: 19
<212> TYPE: RNA
<213> ORGANISM: Artificial Sequence
<220> FEATURE:
<223> OTHER INFORMATION: si-TD084 sense

<400> SEQUENCE: 45
gauuuggaaa aaccgcuau                                                 19

<210> SEQ ID NO 46
<211> LENGTH: 19
<212> TYPE: RNA
<213> ORGANISM: Artificial Sequence
<220> FEATURE:
<223> OTHER INFORMATION: si-TD084 antisense

<400> SEQUENCE: 46
auagcgguuu uuccaaauc                                                 19

<210> SEQ ID NO 47
<211> LENGTH: 19
<212> TYPE: RNA
<213> ORGANISM: Artificial Sequence
<220> FEATURE:
<223> OTHER INFORMATION: si-TD087 sense

<400> SEQUENCE: 47
uuggaaaaac cgcuaugug                                                 19

<210> SEQ ID NO 48
<211> LENGTH: 19
<212> TYPE: RNA
```

```
<213> ORGANISM: Artificial Sequence
<220> FEATURE:
<223> OTHER INFORMATION: si-TD087 antisense

<400> SEQUENCE: 48
cacauagcgg uuuuuccaa                                                    19

<210> SEQ ID NO 49
<211> LENGTH: 19
<212> TYPE: RNA
<213> ORGANISM: Artificial Sequence
<220> FEATURE:
<223> OTHER INFORMATION: si-TD089 sense

<400> SEQUENCE: 49
ggaaaaaccg cuauguggu                                                    19

<210> SEQ ID NO 50
<211> LENGTH: 19
<212> TYPE: RNA
<213> ORGANISM: Artificial Sequence
<220> FEATURE:
<223> OTHER INFORMATION: si-TD089 antisense

<400> SEQUENCE: 50
accacauagc gguuuuucc                                                    19

<210> SEQ ID NO 51
<211> LENGTH: 19
<212> TYPE: RNA
<213> ORGANISM: Artificial Sequence
<220> FEATURE:
<223> OTHER INFORMATION: si-TD093 sense

<400> SEQUENCE: 51
aaaccgcuau guggugcug                                                    19

<210> SEQ ID NO 52
<211> LENGTH: 19
<212> TYPE: RNA
<213> ORGANISM: Artificial Sequence
<220> FEATURE:
<223> OTHER INFORMATION: si-TD093 antisense

<400> SEQUENCE: 52
cagcaccaca uagcgguuu                                                    19

<210> SEQ ID NO 53
<211> LENGTH: 19
<212> TYPE: RNA
<213> ORGANISM: Artificial Sequence
<220> FEATURE:
<223> OTHER INFORMATION: si-TD094 sense

<400> SEQUENCE: 53
aaccgcuaug uggugcuga                                                    19

<210> SEQ ID NO 54
<211> LENGTH: 19
<212> TYPE: RNA
<213> ORGANISM: Artificial Sequence
<220> FEATURE:
<223> OTHER INFORMATION: si-TD094 antisense

<400> SEQUENCE: 54
ucagcaccac auagcgguu                                                    19
```

```
<210> SEQ ID NO 55
<211> LENGTH: 19
<212> TYPE: RNA
<213> ORGANISM: Artificial Sequence
<220> FEATURE:
<223> OTHER INFORMATION: si-TD096 sense

<400> SEQUENCE: 55
ccgcuaugug gugcugaaa                                                       19

<210> SEQ ID NO 56
<211> LENGTH: 19
<212> TYPE: RNA
<213> ORGANISM: Artificial Sequence
<220> FEATURE:
<223> OTHER INFORMATION: si-TD096 antisense

<400> SEQUENCE: 56
uuucagcacc acauagcgg                                                       19

<210> SEQ ID NO 57
<211> LENGTH: 19
<212> TYPE: RNA
<213> ORGANISM: Artificial Sequence
<220> FEATURE:
<223> OTHER INFORMATION: si-TD097 sense

<400> SEQUENCE: 57
cgcuaugugg ugcugaaag                                                       19

<210> SEQ ID NO 58
<211> LENGTH: 19
<212> TYPE: RNA
<213> ORGANISM: Artificial Sequence
<220> FEATURE:
<223> OTHER INFORMATION: si-TD097 antisense

<400> SEQUENCE: 58
cuuucagcac cacauagcg                                                       19

<210> SEQ ID NO 59
<211> LENGTH: 19
<212> TYPE: RNA
<213> ORGANISM: Artificial Sequence
<220> FEATURE:
<223> OTHER INFORMATION: si-TD098 sense

<400> SEQUENCE: 59
gcuauguggu gcugaaagg                                                       19

<210> SEQ ID NO 60
<211> LENGTH: 19
<212> TYPE: RNA
<213> ORGANISM: Artificial Sequence
<220> FEATURE:
<223> OTHER INFORMATION: si-TD098 antisense

<400> SEQUENCE: 60
ccuuucagca ccacauagc                                                       19

<210> SEQ ID NO 61
<211> LENGTH: 19
<212> TYPE: RNA
<213> ORGANISM: Artificial Sequence
<220> FEATURE:
```

<223> OTHER INFORMATION: si-TD136 sense

<400> SEQUENCE: 61
gagaaggagg uaaaagaug								19

<210> SEQ ID NO 62
<211> LENGTH: 19
<212> TYPE: RNA
<213> ORGANISM: Artificial Sequence
<220> FEATURE:
<223> OTHER INFORMATION: si-TD136 antisense

<400> SEQUENCE: 62
caucuuuuac cuccuucuc								19

<210> SEQ ID NO 63
<211> LENGTH: 19
<212> TYPE: RNA
<213> ORGANISM: Artificial Sequence
<220> FEATURE:
<223> OTHER INFORMATION: si-TD137 sense

<400> SEQUENCE: 63
agaaggaggu aaaagauga								19

<210> SEQ ID NO 64
<211> LENGTH: 19
<212> TYPE: RNA
<213> ORGANISM: Artificial Sequence
<220> FEATURE:
<223> OTHER INFORMATION: si-TD137 antisense

<400> SEQUENCE: 64
ucaucuuuua ccuccuucu								19

<210> SEQ ID NO 65
<211> LENGTH: 19
<212> TYPE: RNA
<213> ORGANISM: Artificial Sequence
<220> FEATURE:
<223> OTHER INFORMATION: si-TD138 sense

<400> SEQUENCE: 65
gaaggaggua aaagaugag								19

<210> SEQ ID NO 66
<211> LENGTH: 19
<212> TYPE: RNA
<213> ORGANISM: Artificial Sequence
<220> FEATURE:
<223> OTHER INFORMATION: si-TD138 antisense

<400> SEQUENCE: 66
cucaucuuuu accuccuuc								19

<210> SEQ ID NO 67
<211> LENGTH: 19
<212> TYPE: RNA
<213> ORGANISM: Artificial Sequence
<220> FEATURE:
<223> OTHER INFORMATION: si-TD139 sense

<400> SEQUENCE: 67
aaggagguaa aagaugaga								19

<210> SEQ ID NO 68
<211> LENGTH: 19
<212> TYPE: RNA
<213> ORGANISM: Artificial Sequence
<220> FEATURE:
<223> OTHER INFORMATION: si-TD139 antisense

<400> SEQUENCE: 68
ucucaucuuu uaccuccuu                                                19

<210> SEQ ID NO 69
<211> LENGTH: 19
<212> TYPE: RNA
<213> ORGANISM: Artificial Sequence
<220> FEATURE:
<223> OTHER INFORMATION: si-TD140 sense

<400> SEQUENCE: 69
aggagguaaa agaugagaa                                                19

<210> SEQ ID NO 70
<211> LENGTH: 19
<212> TYPE: RNA
<213> ORGANISM: Artificial Sequence
<220> FEATURE:
<223> OTHER INFORMATION: si-TD140 antisense

<400> SEQUENCE: 70
uucucaucuu uuaccuccu                                                19

<210> SEQ ID NO 71
<211> LENGTH: 19
<212> TYPE: RNA
<213> ORGANISM: Artificial Sequence
<220> FEATURE:
<223> OTHER INFORMATION: si-TD141 sense

<400> SEQUENCE: 71
ggagguaaaa gaugagaaa                                                19

<210> SEQ ID NO 72
<211> LENGTH: 19
<212> TYPE: RNA
<213> ORGANISM: Artificial Sequence
<220> FEATURE:
<223> OTHER INFORMATION: si-TD141 antisense

<400> SEQUENCE: 72
uuucucaucu uuuaccucc                                                19

<210> SEQ ID NO 73
<211> LENGTH: 19
<212> TYPE: RNA
<213> ORGANISM: Artificial Sequence
<220> FEATURE:
<223> OTHER INFORMATION: si-TD143 sense

<400> SEQUENCE: 73
agguaaaaga ugagaaaaa                                                19

<210> SEQ ID NO 74
<211> LENGTH: 19
<212> TYPE: RNA
<213> ORGANISM: Artificial Sequence
<220> FEATURE:
<223> OTHER INFORMATION: si-TD143 antisense

```
<400> SEQUENCE: 74
uuuuucucau cuuuuaccu                                            19

<210> SEQ ID NO 75
<211> LENGTH: 19
<212> TYPE: RNA
<213> ORGANISM: Artificial Sequence
<220> FEATURE:
<223> OTHER INFORMATION: si-TD181 sense

<400> SEQUENCE: 75
cugagugacu augagaagu                                            19

<210> SEQ ID NO 76
<211> LENGTH: 19
<212> TYPE: RNA
<213> ORGANISM: Artificial Sequence
<220> FEATURE:
<223> OTHER INFORMATION: si-TD181 antisense

<400> SEQUENCE: 76
acuucucaua gucacucag                                            19

<210> SEQ ID NO 77
<211> LENGTH: 19
<212> TYPE: RNA
<213> ORGANISM: Artificial Sequence
<220> FEATURE:
<223> OTHER INFORMATION: si-TD179 sense

<400> SEQUENCE: 77
accugaguga cuaugagaa                                            19

<210> SEQ ID NO 78
<211> LENGTH: 19
<212> TYPE: RNA
<213> ORGANISM: Artificial Sequence
<220> FEATURE:
<223> OTHER INFORMATION: si-TD179 antisense

<400> SEQUENCE: 78
uucucauagu cacucaggu                                            19

<210> SEQ ID NO 79
<211> LENGTH: 19
<212> TYPE: RNA
<213> ORGANISM: Artificial Sequence
<220> FEATURE:
<223> OTHER INFORMATION: si-TD178 sense

<400> SEQUENCE: 79
gaccugagug acuaugaga                                            19

<210> SEQ ID NO 80
<211> LENGTH: 19
<212> TYPE: RNA
<213> ORGANISM: Artificial Sequence
<220> FEATURE:
<223> OTHER INFORMATION: si-TD178 antisense

<400> SEQUENCE: 80
ucucauaguc acucagguc                                            19

<210> SEQ ID NO 81
<211> LENGTH: 19
```

```
<212> TYPE: RNA
<213> ORGANISM: Artificial Sequence
<220> FEATURE:
<223> OTHER INFORMATION: si-TD177 sense

<400> SEQUENCE: 81
ugaccugagu gacuaugag                                                   19

<210> SEQ ID NO 82
<211> LENGTH: 19
<212> TYPE: RNA
<213> ORGANISM: Artificial Sequence
<220> FEATURE:
<223> OTHER INFORMATION: si-TD177 antisense

<400> SEQUENCE: 82
cucauaguca cucagguca                                                   19

<210> SEQ ID NO 83
<211> LENGTH: 19
<212> TYPE: RNA
<213> ORGANISM: Artificial Sequence
<220> FEATURE:
<223> OTHER INFORMATION: si-TD176 sense

<400> SEQUENCE: 83
uugaccugag ugacuauga                                                   19

<210> SEQ ID NO 84
<211> LENGTH: 19
<212> TYPE: RNA
<213> ORGANISM: Artificial Sequence
<220> FEATURE:
<223> OTHER INFORMATION: si-TD176 antisense

<400> SEQUENCE: 84
ucauagucac ucaggucaa                                                   19

<210> SEQ ID NO 85
<211> LENGTH: 19
<212> TYPE: RNA
<213> ORGANISM: Artificial Sequence
<220> FEATURE:
<223> OTHER INFORMATION: si-TD224 sense

<400> SEQUENCE: 85
gcaggagcaa gaaaaauca                                                   19

<210> SEQ ID NO 86
<211> LENGTH: 19
<212> TYPE: RNA
<213> ORGANISM: Artificial Sequence
<220> FEATURE:
<223> OTHER INFORMATION: si-TD224 antisense

<400> SEQUENCE: 86
ugauuuuucu ugcuccugc                                                   19

<210> SEQ ID NO 87
<211> LENGTH: 19
<212> TYPE: RNA
<213> ORGANISM: Artificial Sequence
<220> FEATURE:
<223> OTHER INFORMATION: si-TD221 sense

<400> SEQUENCE: 87
```
agagcaggag caagaaaaa					19

<210> SEQ ID NO 88
<211> LENGTH: 19
<212> TYPE: RNA
<213> ORGANISM: Artificial Sequence
<220> FEATURE:
<223> OTHER INFORMATION: si-TD221 antisense

<400> SEQUENCE: 88
uuuuucuugc uccugcucu					19

<210> SEQ ID NO 89
<211> LENGTH: 19
<212> TYPE: RNA
<213> ORGANISM: Artificial Sequence
<220> FEATURE:
<223> OTHER INFORMATION: si-TD217 sense

<400> SEQUENCE: 89
uccaagagca ggagcaaga					19

<210> SEQ ID NO 90
<211> LENGTH: 19
<212> TYPE: RNA
<213> ORGANISM: Artificial Sequence
<220> FEATURE:
<223> OTHER INFORMATION: si-TD217 antisense

<400> SEQUENCE: 90
ucuugcuccu gcucuugga					19

<210> SEQ ID NO 91
<211> LENGTH: 19
<212> TYPE: RNA
<213> ORGANISM: Artificial Sequence
<220> FEATURE:
<223> OTHER INFORMATION: si-TD380 sense

<400> SEQUENCE: 91
ugaggaggac agcuaucuu					19

<210> SEQ ID NO 92
<211> LENGTH: 19
<212> TYPE: RNA
<213> ORGANISM: Artificial Sequence
<220> FEATURE:
<223> OTHER INFORMATION: si-TD380 antisense

<400> SEQUENCE: 92
aagauagcug uccuccuca					19

<210> SEQ ID NO 93
<211> LENGTH: 19
<212> TYPE: RNA
<213> ORGANISM: Artificial Sequence
<220> FEATURE:
<223> OTHER INFORMATION: si-TD378 sense

<400> SEQUENCE: 93
guugaggagg acagcuauc					19

<210> SEQ ID NO 94
<211> LENGTH: 19
<212> TYPE: RNA
<213> ORGANISM: Artificial Sequence

```
<220> FEATURE:
<223> OTHER INFORMATION: si-TD378 antisense

<400> SEQUENCE: 94
gauagcuguc cuccucaac                                                  19

<210> SEQ ID NO 95
<211> LENGTH: 19
<212> TYPE: RNA
<213> ORGANISM: Artificial Sequence
<220> FEATURE:
<223> OTHER INFORMATION: si-TD376 sense

<400> SEQUENCE: 95
ccguugagga ggacagcua                                                  19

<210> SEQ ID NO 96
<211> LENGTH: 19
<212> TYPE: RNA
<213> ORGANISM: Artificial Sequence
<220> FEATURE:
<223> OTHER INFORMATION: si-TD376 antisense

<400> SEQUENCE: 96
uagcuguccu ccucaacgg                                                  19

<210> SEQ ID NO 97
<211> LENGTH: 19
<212> TYPE: RNA
<213> ORGANISM: Artificial Sequence
<220> FEATURE:
<223> OTHER INFORMATION: si-TD372 sense

<400> SEQUENCE: 97
gucaccguug aggaggaca                                                  19

<210> SEQ ID NO 98
<211> LENGTH: 19
<212> TYPE: RNA
<213> ORGANISM: Artificial Sequence
<220> FEATURE:
<223> OTHER INFORMATION: si-TD372 antisense

<400> SEQUENCE: 98
uguccuccuc aacggugac                                                  19

<210> SEQ ID NO 99
<211> LENGTH: 19
<212> TYPE: RNA
<213> ORGANISM: Artificial Sequence
<220> FEATURE:
<223> OTHER INFORMATION: si-TD370 sense

<400> SEQUENCE: 99
aggucaccgu ugaggagga                                                  19

<210> SEQ ID NO 100
<211> LENGTH: 19
<212> TYPE: RNA
<213> ORGANISM: Artificial Sequence
<220> FEATURE:
<223> OTHER INFORMATION: si-TD370 antisense

<400> SEQUENCE: 100
uccuccucaa cggugaccu                                                  19
```

```
<210> SEQ ID NO 101
<211> LENGTH: 19
<212> TYPE: RNA
<213> ORGANISM: Artificial Sequence
<220> FEATURE:
<223> OTHER INFORMATION: si-TD364 sense

<400> SEQUENCE: 101
uggaugaggu caccguuga                                                 19

<210> SEQ ID NO 102
<211> LENGTH: 19
<212> TYPE: RNA
<213> ORGANISM: Artificial Sequence
<220> FEATURE:
<223> OTHER INFORMATION: si-TD364 antisense

<400> SEQUENCE: 102
ucaacgguga ccucaucca                                                 19

<210> SEQ ID NO 103
<211> LENGTH: 19
<212> TYPE: RNA
<213> ORGANISM: Artificial Sequence
<220> FEATURE:
<223> OTHER INFORMATION: si-TD362 sense

<400> SEQUENCE: 103
cuuggaugag gucaccguu                                                 19

<210> SEQ ID NO 104
<211> LENGTH: 19
<212> TYPE: RNA
<213> ORGANISM: Artificial Sequence
<220> FEATURE:
<223> OTHER INFORMATION: si-TD362 antisense

<400> SEQUENCE: 104
aacggugacc ucauccaag                                                 19

<210> SEQ ID NO 105
<211> LENGTH: 19
<212> TYPE: RNA
<213> ORGANISM: Artificial Sequence
<220> FEATURE:
<223> OTHER INFORMATION: si-TD358 sense

<400> SEQUENCE: 105
guaucuugga ugaggucac                                                 19

<210> SEQ ID NO 106
<211> LENGTH: 19
<212> TYPE: RNA
<213> ORGANISM: Artificial Sequence
<220> FEATURE:
<223> OTHER INFORMATION: si-TD358 antisense

<400> SEQUENCE: 106
gugaccucau ccaagauac                                                 19

<210> SEQ ID NO 107
<211> LENGTH: 19
<212> TYPE: RNA
<213> ORGANISM: Artificial Sequence
<220> FEATURE:
<223> OTHER INFORMATION: si-TD451 sense
```

<400> SEQUENCE: 107
aggaagaccc uuccccuga                                                    19

<210> SEQ ID NO 108
<211> LENGTH: 19
<212> TYPE: RNA
<213> ORGANISM: Artificial Sequence
<220> FEATURE:
<223> OTHER INFORMATION: si-TD451 antisense

<400> SEQUENCE: 108
ucaggggaag ggucuuccu                                                    19

<210> SEQ ID NO 109
<211> LENGTH: 19
<212> TYPE: RNA
<213> ORGANISM: Artificial Sequence
<220> FEATURE:
<223> OTHER INFORMATION: si-TD443 sense

<400> SEQUENCE: 109
gauccaagag gaagacccu                                                    19

<210> SEQ ID NO 110
<211> LENGTH: 19
<212> TYPE: RNA
<213> ORGANISM: Artificial Sequence
<220> FEATURE:
<223> OTHER INFORMATION: si-TD443 antisense

<400> SEQUENCE: 110
agggucuucc ucuuggauc                                                    19

<210> SEQ ID NO 111
<211> LENGTH: 19
<212> TYPE: RNA
<213> ORGANISM: Artificial Sequence
<220> FEATURE:
<223> OTHER INFORMATION: si-TD509 sense

<400> SEQUENCE: 111
ggacaagucu guggcccag                                                    19

<210> SEQ ID NO 112
<211> LENGTH: 19
<212> TYPE: RNA
<213> ORGANISM: Artificial Sequence
<220> FEATURE:
<223> OTHER INFORMATION: si-TD509 antisense

<400> SEQUENCE: 112
cugggccaca gacuugucc                                                    19

<210> SEQ ID NO 113
<211> LENGTH: 19
<212> TYPE: RNA
<213> ORGANISM: Artificial Sequence
<220> FEATURE:
<223> OTHER INFORMATION: si-TD508 sense

<400> SEQUENCE: 113
uggacaaguc uguggccca                                                    19

<210> SEQ ID NO 114

```
<211> LENGTH: 19
<212> TYPE: RNA
<213> ORGANISM: Artificial Sequence
<220> FEATURE:
<223> OTHER INFORMATION: si-TD508 antisense

<400> SEQUENCE: 114
ugggccacag acugucca                                                  19

<210> SEQ ID NO 115
<211> LENGTH: 19
<212> TYPE: RNA
<213> ORGANISM: Artificial Sequence
<220> FEATURE:
<223> OTHER INFORMATION: si-TD577 sense

<400> SEQUENCE: 115
gccucccugg aggagaucc                                                 19

<210> SEQ ID NO 116
<211> LENGTH: 19
<212> TYPE: RNA
<213> ORGANISM: Artificial Sequence
<220> FEATURE:
<223> OTHER INFORMATION: si-TD577 antisense

<400> SEQUENCE: 116
ggaucuccuc cagggaggc                                                 19

<210> SEQ ID NO 117
<211> LENGTH: 19
<212> TYPE: RNA
<213> ORGANISM: Artificial Sequence
<220> FEATURE:
<223> OTHER INFORMATION: si-TD611 sense

<400> SEQUENCE: 117
gguagcaagg aaacuggag                                                 19

<210> SEQ ID NO 118
<211> LENGTH: 19
<212> TYPE: RNA
<213> ORGANISM: Artificial Sequence
<220> FEATURE:
<223> OTHER INFORMATION: si-TD611 antisense

<400> SEQUENCE: 118
cuccaguuuc cuugcuacc                                                 19

<210> SEQ ID NO 119
<211> LENGTH: 19
<212> TYPE: RNA
<213> ORGANISM: Artificial Sequence
<220> FEATURE:
<223> OTHER INFORMATION: si-TD609 sense

<400> SEQUENCE: 119
cugguagcaa ggaaacugg                                                 19

<210> SEQ ID NO 120
<211> LENGTH: 19
<212> TYPE: RNA
<213> ORGANISM: Artificial Sequence
<220> FEATURE:
<223> OTHER INFORMATION: si-TD609 antisense

<400> SEQUENCE: 120
```

```
ccaguuuccu ugcuaccag                                              19

<210> SEQ ID NO 121
<211> LENGTH: 19
<212> TYPE: RNA
<213> ORGANISM: Artificial Sequence
<220> FEATURE:
<223> OTHER INFORMATION: si-TD607 sense

<400> SEQUENCE: 121
accugguagc aaggaaacu                                              19

<210> SEQ ID NO 122
<211> LENGTH: 19
<212> TYPE: RNA
<213> ORGANISM: Artificial Sequence
<220> FEATURE:
<223> OTHER INFORMATION: si-TD607 antisense

<400> SEQUENCE: 122 aguuccuug cuaccaggu                                               19

<210> SEQ ID NO 123
<211> LENGTH: 19
<212> TYPE: RNA
<213> ORGANISM: Artificial Sequence
<220> FEATURE:
<223> OTHER INFORMATION: si-TD604 sense

<400> SEQUENCE: 123
aggaccuggu agcaaggaa                                              19

<210> SEQ ID NO 124
<211> LENGTH: 19
<212> TYPE: RNA
<213> ORGANISM: Artificial Sequence
<220> FEATURE:
<223> OTHER INFORMATION: si-TD604 antisense

<400> SEQUENCE: 124
uuccuugcua ccagguccu                                              19

<210> SEQ ID NO 125
<211> LENGTH: 19
<212> TYPE: RNA
<213> ORGANISM: Artificial Sequence
<220> FEATURE:
<223> OTHER INFORMATION: si-TD600 sense

<400> SEQUENCE: 125
auccaggacc ugguagcaa                                              19

<210> SEQ ID NO 126
<211> LENGTH: 19
<212> TYPE: RNA
<213> ORGANISM: Artificial Sequence
<220> FEATURE:
<223> OTHER INFORMATION: si-TD600 antisense

<400> SEQUENCE: 126
uugcuaccag guccuggau                                              19

<210> SEQ ID NO 127
<211> LENGTH: 19
<212> TYPE: RNA
```

<213> ORGANISM: Artificial Sequence
<220> FEATURE:
<223> OTHER INFORMATION: si-TD598 sense

<400> SEQUENCE: 127
ggauccagga ccugguagc							19

<210> SEQ ID NO 128
<211> LENGTH: 19
<212> TYPE: RNA
<213> ORGANISM: Artificial Sequence
<220> FEATURE:
<223> OTHER INFORMATION: si-TD598 antisense

<400> SEQUENCE: 128
gcuaccaggu ccuggaucc							19

<210> SEQ ID NO 129
<211> LENGTH: 19
<212> TYPE: RNA
<213> ORGANISM: Artificial Sequence
<220> FEATURE:
<223> OTHER INFORMATION: si-TD596 sense

<400> SEQUENCE: 129
ccggauccag gaccuggua							19

<210> SEQ ID NO 130
<211> LENGTH: 19
<212> TYPE: RNA
<213> ORGANISM: Artificial Sequence
<220> FEATURE:
<223> OTHER INFORMATION: si-TD596 antisense

<400> SEQUENCE: 130
uaccaggucc uggauccgg							19

<210> SEQ ID NO 131
<211> LENGTH: 19
<212> TYPE: RNA
<213> ORGANISM: Artificial Sequence
<220> FEATURE:
<223> OTHER INFORMATION: si-TD588 sense

<400> SEQUENCE: 131
cagcuguccc ggauccagg							19

<210> SEQ ID NO 132
<211> LENGTH: 19
<212> TYPE: RNA
<213> ORGANISM: Artificial Sequence
<220> FEATURE:
<223> OTHER INFORMATION: si-TD588 antisense

<400> SEQUENCE: 132
ccuggauccg ggacagcug							19

<210> SEQ ID NO 133
<211> LENGTH: 19
<212> TYPE: RNA
<213> ORGANISM: Artificial Sequence
<220> FEATURE:
<223> OTHER INFORMATION: si-TD587 sense

<400> SEQUENCE: 133
gcagcugucc cggauccag							19

```
<210> SEQ ID NO 134
<211> LENGTH: 19
<212> TYPE: RNA
<213> ORGANISM: Artificial Sequence
<220> FEATURE:
<223> OTHER INFORMATION: si-TD587 antisense

<400> SEQUENCE: 134
cuggauccgg gacagcugc                                              19

<210> SEQ ID NO 135
<211> LENGTH: 19
<212> TYPE: RNA
<213> ORGANISM: Artificial Sequence
<220> FEATURE:
<223> OTHER INFORMATION: si-TD585 sense

<400> SEQUENCE: 135
gggcagcugu cccggaucc                                              19

<210> SEQ ID NO 136
<211> LENGTH: 19
<212> TYPE: RNA
<213> ORGANISM: Artificial Sequence
<220> FEATURE:
<223> OTHER INFORMATION: si-TD585 antisense

<400> SEQUENCE: 136
ggauccggga cagcugccc                                              19

<210> SEQ ID NO 137
<211> LENGTH: 19
<212> TYPE: RNA
<213> ORGANISM: Artificial Sequence
<220> FEATURE:
<223> OTHER INFORMATION: si-TD720 sense

<400> SEQUENCE: 137
gagcugagag accuguaca                                              19

<210> SEQ ID NO 138
<211> LENGTH: 19
<212> TYPE: RNA
<213> ORGANISM: Artificial Sequence
<220> FEATURE:
<223> OTHER INFORMATION: si-TD720 antisense

<400> SEQUENCE: 138
uguacagguc ucucagcuc                                              19

<210> SEQ ID NO 139
<211> LENGTH: 19
<212> TYPE: RNA
<213> ORGANISM: Artificial Sequence
<220> FEATURE:
<223> OTHER INFORMATION: si-TD718 sense

<400> SEQUENCE: 139
gggagcugag agaccugua                                              19

<210> SEQ ID NO 140
<211> LENGTH: 19
<212> TYPE: RNA
<213> ORGANISM: Artificial Sequence
<220> FEATURE:
```

<223> OTHER INFORMATION: si-TD718 antisense

<400> SEQUENCE: 140
uacaggucuc ucagcuccc                                          19

<210> SEQ ID NO 141
<211> LENGTH: 19
<212> TYPE: RNA
<213> ORGANISM: Artificial Sequence
<220> FEATURE:
<223> OTHER INFORMATION: si-TD743 sense

<400> SEQUENCE: 141
gacucccacc ucagacaga                                          19

<210> SEQ ID NO 142
<211> LENGTH: 19
<212> TYPE: RNA
<213> ORGANISM: Artificial Sequence
<220> FEATURE:
<223> OTHER INFORMATION: si-TD743 antisense

<400> SEQUENCE: 142
ucugucugag gugggaguc                                          19

<210> SEQ ID NO 143
<211> LENGTH: 19
<212> TYPE: RNA
<213> ORGANISM: Artificial Sequence
<220> FEATURE:
<223> OTHER INFORMATION: si-TD145 sense

<400> SEQUENCE: 143
guaaaagaug agaaaaaua                                          19

<210> SEQ ID NO 144
<211> LENGTH: 19
<212> TYPE: RNA
<213> ORGANISM: Artificial Sequence
<220> FEATURE:
<223> OTHER INFORMATION: si-TD145 antisense

<400> SEQUENCE: 144
uauuuuucuc aucuuuuac                                          19

<210> SEQ ID NO 145
<211> LENGTH: 19
<212> TYPE: RNA
<213> ORGANISM: Artificial Sequence
<220> FEATURE:
<223> OTHER INFORMATION: si-TD480 sense

<400> SEQUENCE: 145
ucuugugcug agagcuuuc                                          19

<210> SEQ ID NO 146
<211> LENGTH: 19
<212> TYPE: RNA
<213> ORGANISM: Artificial Sequence
<220> FEATURE:
<223> OTHER INFORMATION: si-TD480 antisense

<400> SEQUENCE: 146
gaaagcucuc agcacaaga                                          19

```
<210> SEQ ID NO 147
<211> LENGTH: 19
<212> TYPE: RNA
<213> ORGANISM: Artificial Sequence
<220> FEATURE:
<223> OTHER INFORMATION: si-TD483 sense

<400> SEQUENCE: 147
ugugcugaga gcuuucggg                                              19

<210> SEQ ID NO 148
<211> LENGTH: 19
<212> TYPE: RNA
<213> ORGANISM: Artificial Sequence
<220> FEATURE:
<223> OTHER INFORMATION: si-TD483 antisense

<400> SEQUENCE: 148
cccgaaagcu cucagcaca                                              19

<210> SEQ ID NO 149
<211> LENGTH: 19
<212> TYPE: RNA
<213> ORGANISM: Artificial Sequence
<220> FEATURE:
<223> OTHER INFORMATION: si-TD736 sense

<400> SEQUENCE: 149
acagacagau ggaccugca                                              19

<210> SEQ ID NO 150
<211> LENGTH: 19
<212> TYPE: RNA
<213> ORGANISM: Artificial Sequence
<220> FEATURE:
<223> OTHER INFORMATION: si-TD736 antisense

<400> SEQUENCE: 150
ugcaggucca ucugucugu                                              19

<210> SEQ ID NO 151
<211> LENGTH: 19
<212> TYPE: RNA
<213> ORGANISM: Artificial Sequence
<220> FEATURE:
<223> OTHER INFORMATION: si-TD734 sense

<400> SEQUENCE: 151
guacagacag auggaccug                                              19

<210> SEQ ID NO 152
<211> LENGTH: 19
<212> TYPE: RNA
<213> ORGANISM: Artificial Sequence
<220> FEATURE:
<223> OTHER INFORMATION: si-TD734 antisense

<400> SEQUENCE: 152
cagguccauc ugucuguac                                              19

<210> SEQ ID NO 153
<211> LENGTH: 19
<212> TYPE: RNA
<213> ORGANISM: Artificial Sequence
<220> FEATURE:
<223> OTHER INFORMATION: si-TD730 sense
```

```
<400> SEQUENCE: 153
accuguacag acagaugga                                              19

<210> SEQ ID NO 154
<211> LENGTH: 19
<212> TYPE: RNA
<213> ORGANISM: Artificial Sequence
<220> FEATURE:
<223> OTHER INFORMATION: si-TD730 antisense

<400> SEQUENCE: 154
uccaucuguc uguacaggu                                              19

<210> SEQ ID NO 155
<211> LENGTH: 19
<212> TYPE: RNA
<213> ORGANISM: Artificial Sequence
<220> FEATURE:
<223> OTHER INFORMATION: si-TD726 sense

<400> SEQUENCE: 155
agagaccugu acagacaga                                              19

<210> SEQ ID NO 156
<211> LENGTH: 19
<212> TYPE: RNA
<213> ORGANISM: Artificial Sequence
<220> FEATURE:
<223> OTHER INFORMATION: si-TD726 antisense

<400> SEQUENCE: 156
ucugucugua caggucucu                                              19

<210> SEQ ID NO 157
<211> LENGTH: 19
<212> TYPE: RNA
<213> ORGANISM: Artificial Sequence
<220> FEATURE:
<223> OTHER INFORMATION: si-TD723 sense

<400> SEQUENCE: 157
cugagagacc uguacagac                                              19

<210> SEQ ID NO 158
<211> LENGTH: 19
<212> TYPE: RNA
<213> ORGANISM: Artificial Sequence
<220> FEATURE:
<223> OTHER INFORMATION: si-TD723 antisense

<400> SEQUENCE: 158
gucuguacag gucucucag                                              19

<210> SEQ ID NO 159
<211> LENGTH: 19
<212> TYPE: RNA
<213> ORGANISM: Artificial Sequence
<220> FEATURE:
<223> OTHER INFORMATION: si-TD717 sense

<400> SEQUENCE: 159
agggagcuga gagaccugu                                              19

<210> SEQ ID NO 160
<211> LENGTH: 19
```

```
<212> TYPE: RNA
<213> ORGANISM: Artificial Sequence
<220> FEATURE:
<223> OTHER INFORMATION: si-TD717 antisense

<400> SEQUENCE: 160
acaggucucu cagcuccccu                                                 19

<210> SEQ ID NO 161
<211> LENGTH: 19
<212> TYPE: RNA
<213> ORGANISM: Artificial Sequence
<220> FEATURE:
<223> OTHER INFORMATION: si-7 sense

<400> SEQUENCE: 161
ugggagaugg gaagcgaaa                                                  19

<210> SEQ ID NO 162
<211> LENGTH: 19
<212> TYPE: RNA
<213> ORGANISM: Artificial Sequence
<220> FEATURE:
<223> OTHER INFORMATION: si-7 antisense

<400> SEQUENCE: 162
uuucgcuucc caucuccca                                                  19

<210> SEQ ID NO 163
<211> LENGTH: 19
<212> TYPE: RNA
<213> ORGANISM: Artificial Sequence
<220> FEATURE:
<223> OTHER INFORMATION: si-10 sense

<400> SEQUENCE: 163
cagacaaagg ggccaccua                                                  19

<210> SEQ ID NO 164
<211> LENGTH: 19
<212> TYPE: RNA
<213> ORGANISM: Artificial Sequence
<220> FEATURE:
<223> OTHER INFORMATION: si-10 antisense

<400> SEQUENCE: 164
uagguggccc cuuugucug                                                  19

<210> SEQ ID NO 165
<211> LENGTH: 19
<212> TYPE: RNA
<213> ORGANISM: Artificial Sequence
<220> FEATURE:
<223> OTHER INFORMATION: si-1 sense

<400> SEQUENCE: 165
ggaccuggua gcaaggaaa                                                  19

<210> SEQ ID NO 166
<211> LENGTH: 19
<212> TYPE: RNA
<213> ORGANISM: Artificial Sequence
<220> FEATURE:
<223> OTHER INFORMATION: si-1 antisense

<400> SEQUENCE: 166
```
uuuccuugcu accaggucc                                                     19

<210> SEQ ID NO 167
<211> LENGTH: 20
<212> TYPE: DNA
<213> ORGANISM: Artificial Sequence
<220> FEATURE:
<223> OTHER INFORMATION: hCIKP1-F

<400> SEQUENCE: 167
ggaaccaacc tcttgtgctg                                                    20

<210> SEQ ID NO 168
<211> LENGTH: 20
<212> TYPE: DNA
<213> ORGANISM: Artificial Sequence
<220> FEATURE:
<223> OTHER INFORMATION: hCIKP1-R

<400> SEQUENCE: 168
gtcaacttct tgggtgcctg                                                    20

<210> SEQ ID NO 169
<211> LENGTH: 23
<212> TYPE: DNA
<213> ORGANISM: Artificial Sequence
<220> FEATURE:
<223> OTHER INFORMATION: hGADPH-F

<400> SEQUENCE: 169
catgagaagt atgacaacag cct                                                23

<210> SEQ ID NO 170
<211> LENGTH: 22
<212> TYPE: DNA
<213> ORGANISM: Artificial Sequence
<220> FEATURE:
<223> OTHER INFORMATION: hGADPH-R

<400> SEQUENCE: 170
agtccttcca cgataccaaa gt                                                 22

<210> SEQ ID NO 171
<211> LENGTH: 18
<212> TYPE: DNA
<213> ORGANISM: Artificial Sequence
<220> FEATURE:
<223> OTHER INFORMATION: mouse TNF-a-F

<400> SEQUENCE: 171
tcagcgagga cagcaagg                                                      18

<210> SEQ ID NO 172
<211> LENGTH: 22
<212> TYPE: DNA
<213> ORGANISM: Artificial Sequence
<220> FEATURE:
<223> OTHER INFORMATION: mouse TNFa-R

<400> SEQUENCE: 172
agtgagtgaa agggacagaa cc                                                 22

<210> SEQ ID NO 173
<211> LENGTH: 20
<212> TYPE: DNA
<213> ORGANISM: Artificial Sequence

```
<220> FEATURE:
<223> OTHER INFORMATION: mouse IL6-F

<400> SEQUENCE: 173
ccttcttggg actgatgctg                                                20

<210> SEQ ID NO 174
<211> LENGTH: 22
<212> TYPE: DNA
<213> ORGANISM: Artificial Sequence
<220> FEATURE:
<223> OTHER INFORMATION: mouse IL6-R

<400> SEQUENCE: 174
ttgggagtgg tatcctctgt ga                                             22

<210> SEQ ID NO 175
<211> LENGTH: 24
<212> TYPE: DNA
<213> ORGANISM: Artificial Sequence
<220> FEATURE:
<223> OTHER INFORMATION: mouse GAPDH-F

<400> SEQUENCE: 175
ccttcattga cctcaactac atgg                                           24

<210> SEQ ID NO 176
<211> LENGTH: 20
<212> TYPE: DNA
<213> ORGANISM: Artificial Sequence
<220> FEATURE:
<223> OTHER INFORMATION: mouse GAPDH-R

<400> SEQUENCE: 176
ctcgctcctg gaagatggtg                                                20

<210> SEQ ID NO 177
<211> LENGTH: 20
<212> TYPE: DNA
<213> ORGANISM: Artificial Sequence
<220> FEATURE:
<223> OTHER INFORMATION: ALP-F

<400> SEQUENCE: 177
gtcagctcca ccacaaccct                                                20

<210> SEQ ID NO 178
<211> LENGTH: 20
<212> TYPE: DNA
<213> ORGANISM: Artificial Sequence
<220> FEATURE:
<223> OTHER INFORMATION: ALP-R

<400> SEQUENCE: 178
gccctcattg gccttcaccc                                                20

<210> SEQ ID NO 179
<211> LENGTH: 20
<212> TYPE: DNA
<213> ORGANISM: Artificial Sequence
<220> FEATURE:
<223> OTHER INFORMATION: COL1-F

<400> SEQUENCE: 179
cactggtgat gctggtcctg                                                20
```

<210> SEQ ID NO 180
<211> LENGTH: 19
<212> TYPE: DNA
<213> ORGANISM: Artificial Sequence
<220> FEATURE:
<223> OTHER INFORMATION: COL1-R

<400> SEQUENCE: 180
cgaggtcacg gtcacgaac                                            19

<210> SEQ ID NO 181
<211> LENGTH: 20
<212> TYPE: DNA
<213> ORGANISM: Artificial Sequence
<220> FEATURE:
<223> OTHER INFORMATION: OPN-F

<400> SEQUENCE: 181
gtaccctgat gctacagacg                                           20

<210> SEQ ID NO 182
<211> LENGTH: 20
<212> TYPE: DNA
<213> ORGANISM: Artificial Sequence
<220> FEATURE:
<223> OTHER INFORMATION: OPN-R

<400> SEQUENCE: 182
ttcataactg tccttcccac                                           20

<210> SEQ ID NO 183
<211> LENGTH: 20
<212> TYPE: DNA
<213> ORGANISM: Artificial Sequence
<220> FEATURE:
<223> OTHER INFORMATION: BSP-F

<400> SEQUENCE: 183
ggcacctcga agacaacaac                                           20

<210> SEQ ID NO 184
<211> LENGTH: 20
<212> TYPE: DNA
<213> ORGANISM: Artificial Sequence
<220> FEATURE:
<223> OTHER INFORMATION: BSP-R

<400> SEQUENCE: 184
gcccgtgtat tcgtactccc                                           20

<210> SEQ ID NO 185
<211> LENGTH: 20
<212> TYPE: DNA
<213> ORGANISM: Artificial Sequence
<220> FEATURE:
<223> OTHER INFORMATION: OC-F

<400> SEQUENCE: 185
agggcagcga ggtagtgaag                                           20

<210> SEQ ID NO 186
<211> LENGTH: 20
<212> TYPE: DNA
<213> ORGANISM: Artificial Sequence
<220> FEATURE:
<223> OTHER INFORMATION: OC-R

```
<400> SEQUENCE: 186
tgtggtcagc caactcgtca                                               20

<210> SEQ ID NO 187
<211> LENGTH: 21
<212> TYPE: DNA
<213> ORGANISM: Artificial Sequence
<220> FEATURE:
<223> OTHER INFORMATION: GAPDH-F

<400> SEQUENCE: 187
ggcatggact gtggtcatga g                                             21

<210> SEQ ID NO 188
<211> LENGTH: 20
<212> TYPE: DNA
<213> ORGANISM: Artificial Sequence
<220> FEATURE:
<223> OTHER INFORMATION: GAPDH-R

<400> SEQUENCE: 188
tgcaccacca actgcttagc                                               20

<210> SEQ ID NO 189
<211> LENGTH: 19
<212> TYPE: DNA
<213> ORGANISM: Artificial Sequence
<220> FEATURE:
<223> OTHER INFORMATION: mouse IL-17A-F

<400> SEQUENCE: 189
ctccaccgca atgaagacc                                                19

<210> SEQ ID NO 190
<211> LENGTH: 20
<212> TYPE: DNA
<213> ORGANISM: Artificial Sequence
<220> FEATURE:
<223> OTHER INFORMATION: mouse IL-17A-R

<400> SEQUENCE: 190
ccctcttcag gaccaggatc                                               20

<210> SEQ ID NO 191
<211> LENGTH: 21
<212> TYPE: DNA
<213> ORGANISM: Artificial Sequence
<220> FEATURE:
<223> OTHER INFORMATION: mouse CKIP-1-F

<400> SEQUENCE: 191
tttctcggcc ttgggaaaaa c                                             21

<210> SEQ ID NO 192
<211> LENGTH: 19
<212> TYPE: DNA
<213> ORGANISM: Artificial Sequence
<220> FEATURE:
<223> OTHER INFORMATION: mouse CKIP-1-R

<400> SEQUENCE: 192
gaggcacatc ggctcttct                                                19
```

DOUBLE-STRANDED RNA MOLECULE TARGETING CKIP-1 AND USE THEREOF

FIELD OF THE INVENTION

The present invention relates to the field of biomedicine, particularly to double-stranded RNA molecules targeting CKIP-1 and uses thereof, particularly to use of the double-stranded RNA molecules for the treatment of inflammatory diseases such as arthritis, particularly rheumatoid arthritis.

CROSS-REFERENCE TO RELATED APPLICATIONS

This application is a U.S. 371 Nat'l Stage Appl. of Int'l Appl. No. PCT/CN2018/104552, filed Sep. 7, 2018, which claims priority to Intl Appl. No. PCT/CN2017/100863, filed Sep. 7, 2017; Intl Appl. No. PCT/CN2017/100864, filed Sep. 7, 2017; Int'l Appl. No. PCT/CN2017/100865, filed Sep. 7, 2017; Int'l Appl. No. PCT/CN2017/100866, filed Sep. 7, 2017; and Int'l Appl. No. PCT/CN2017/100867, filed Sep. 7, 2017, all of which are incorporated herein by reference.

REFERENCE TO THE SEQUENCE LISTING

This application includes as part of its disclosure a biological sequence listing which is being concurrently submitted through EFS-Web. Said biological sequence listing is contained in a file named "115849800001801.txt" which was created on Mar. 3, 2020, and has a size of 36,806 bytes, and is hereby incorporated by reference in its entirety.

BACKGROUND OF THE INVENTION

Casein Kinase Interacting Protein 1 (CKIP-1) is a bone formation inhibiting gene that specifically regulates bone formation rather than bone resorption. CKIP-1 is highly expressed in bone tissue of patients with osteoporosis. Targeted inhibition of CKIP-1 expression has been proven to be useful in the treatment of osteoporosis or other pathological bone destruction. However, CKIP-1 has not been associated with inflammation in the art.

TNF-α and IL-6 are two important pro-inflammatory cytokines and play an important role in the inflammatory response of the body. The levels of TNF-α and IL-6 are low in human bodies under physiological conditions. However, under pathological conditions, increased secretion of TNF-α and IL-6, and the resulting cascade of various pro-inflammatory factors, can lead to an inflammatory response, and thus tissue damage. Inflammatory diseases have been treated in the art by targeted inhibition of TNF-α and IL-6. For example, a number of inhibitors targeting TNF-α have been marketed, including Infliximab, Etanercept, Adalimumab, Golimumab, and Certolizumab. In addition, IL-6 blockers have been marketed for clinical use, such as tolizumab. In a large randomized, double-blind clinical trial, tolizumab has a good therapeutic effect in patients who do not respond to TNF-α mAb.

Rheumatoid arthritis (RA) is a chronic systemic autoimmune disease characterized by multi-joint synovitis. Prolonged recurrent episodes of synovitis can lead to destruction of intra-articular cartilage and bone, joint dysfunction, and even disability. Rheumatoid arthritis has a high incidence in adults, about 20-40% per 100,000 adults. Studies have shown that 70-75% of rheumatoid arthritis patients have bone destruction within 3 years of onset, 10% of them have severe dysfunction within 2 years of onset, and about 50% of them lose their ability to work after 10 years of onset, resulting in serious economic burden to both patients and society. At present, the drugs for treating RA mainly comprise non-steroidal anti-inflammatory drugs, hormones, anti-rheumatic drugs and the like, and are mainly used for relieving pain, relieving inflammation but are not effective in preventing joint and bone destruction. In recent years, some new biological agents can alleviate and inhibit the occurrence of bone destruction, but cannot repair the existing bone injury. There is currently a clinical lack of RA therapeutics that both reduce inflammation and promote bone repair.

SUMMARY OF THE INVENTION

In a first aspect, the present invention provides a double-stranded RNA (dsRNA) molecule comprising a sense strand and an antisense strand which are selected from the group consisting of:

1) a sense strand shown in SEQ ID NO: 63 and an antisense strand shown in SEQ ID NO: 64;
2) a sense strand shown in SEQ ID NO: 71 and an antisense strand shown in SEQ ID NO: 72;
3) a sense strand shown in SEQ ID NO: 83 and an antisense strand shown in SEQ ID NO: 84; and
4) a sense strand shown in SEQ ID NO: 161 and an antisense strand shown in SEQ ID NO: 162.

In some embodiments, the sense and/or antisense strand additionally has an overhang of at least one nucleotide at the 3' end. In some embodiments, the sense and/or antisense strand additionally has an overhang of 2 nucleotides at the 3' end, preferably the overhang is Ti'.

In some embodiments, the sense and antisense strands comprise 1 or 2 nucleotide substitutions located within the 6, 5, 4, 3, or 2 nucleotides from the 5' and/or 3' end. In some embodiments, the sense and antisense strands comprise 1 nucleotide substitution located at the last nucleotide of the 3' end of the sense strand and correspondingly at the first nucleotide of the 5' end of the antisense strand.

In some embodiments, the dsRNA comprises at least one modified nucleotide. In some embodiments, the modified nucleotide is selected from the group consisting of: 2'-O-methyl modified nucleotides, 2'-F modified nucleotides, nucleotides containing 5'-phosphorothioate groups and end nucleotides linked to cholesteryl derivatives or dodecanoic acid bisdecylamide groups, 2'-deoxy-2'-fluoro modified nucleotides, 2'-deoxy-modified nucleotides, locked nucleotides, abasic nucleotides, 2'-amino-modified nucleotides, 2'-alkyl-modified nucleotides, morpholino nucleotides, phosphoramidates and nucleotides containing non-natural bases. In some embodiments, the 2' hydroxyl groups of all nucleotides with uracil or cytosine bases in the sense and/or antisense strands of the dsRNA are modified with methoxy groups.

In some embodiments, the dsRNA molecule is an siRNA or shRNA. In some embodiments, the dsRNA molecule inhibits CKIP-1 expression by at least 50%, preferably by at least 70%. In some embodiments, the dsRNA molecule inhibits expression of a pro-inflammatory cytokine such as IL-6, TNF-α, and/or IL-17A.

In a second aspect, the invention also provides an expression vector comprising a nucleotide sequence encoding the dsRNA molecule of the invention, and the nucleotide sequence is operably linked to a transcription regulation element.

In a third aspect, the invention also provides a pharmaceutical composition comprising the dsRNA molecule of the invention or the expression vector of the invention, and a pharmaceutically acceptable carrier.

In a fourth aspect, the invention provides a method of treating arthritis, particularly rheumatoid arthritis, in a subject in need thereof, comprising administering to the subject a therapeutically effective amount of the dsRNA molecule of the invention or the expression vector of the invention or the pharmaceutical composition of the invention. In some embodiments, the method further comprises administering to the subject an additional therapeutic agent for treating arthritis, particularly rheumatoid arthritis.

In a fifth aspect, the invention provides the use of the dsRNA molecule of the invention or the expression vector of the invention or the pharmaceutical composition of the invention for the manufacture of a medicament for the treatment of arthritis, in particular rheumatoid arthritis, in a subject in need thereof.

In a sixth aspect, the invention provides a method of treating an inflammatory disease in a subject in need thereof, comprising administering to the subject a therapeutically effective amount of the dsRNA molecule of the invention or the expression vector of the invention or the pharmaceutical composition of the invention. In some embodiments, the method further comprises administering to the subject an additional therapeutic agent for treating an inflammatory disease.

In a seventh aspect, the invention provides the use of the dsRNA molecule of the invention or the expression vector of the invention or the pharmaceutical composition of the invention in the preparation of a medicament for treating an inflammatory disease in a subject in need thereof.

In an eighth aspect, the present invention provides a method of treating a bone metabolism-related disorder in a subject in need thereof, comprising administering to the subject a therapeutically effective amount of the dsRNA molecule of the present invention or the expression vector of the present invention or the pharmaceutical composition of the present invention. In some embodiments, the method further comprises administering to the subject an additional therapeutic agent for treating a bone metabolism-related disorder.

In a ninth aspect, the invention provides the use of the dsRNA molecule of the invention or the expression vector of the invention or the pharmaceutical composition of the invention in the preparation of a medicament for treating a bone metabolism-related disorder in a subject in need thereof.

In various aspects of the invention, the subject is a human.

BRIEF DESCRIPTION OF THE DRAWINGS

FIG. 1 shows a pool of candidate siRNA sequences, and the TT at the 3' end of each sequence is the overhang which is not complementary to the target sequence.

DETAILED DESCRIPTION OF THE INVENTION

I. Definition

Figure 2:
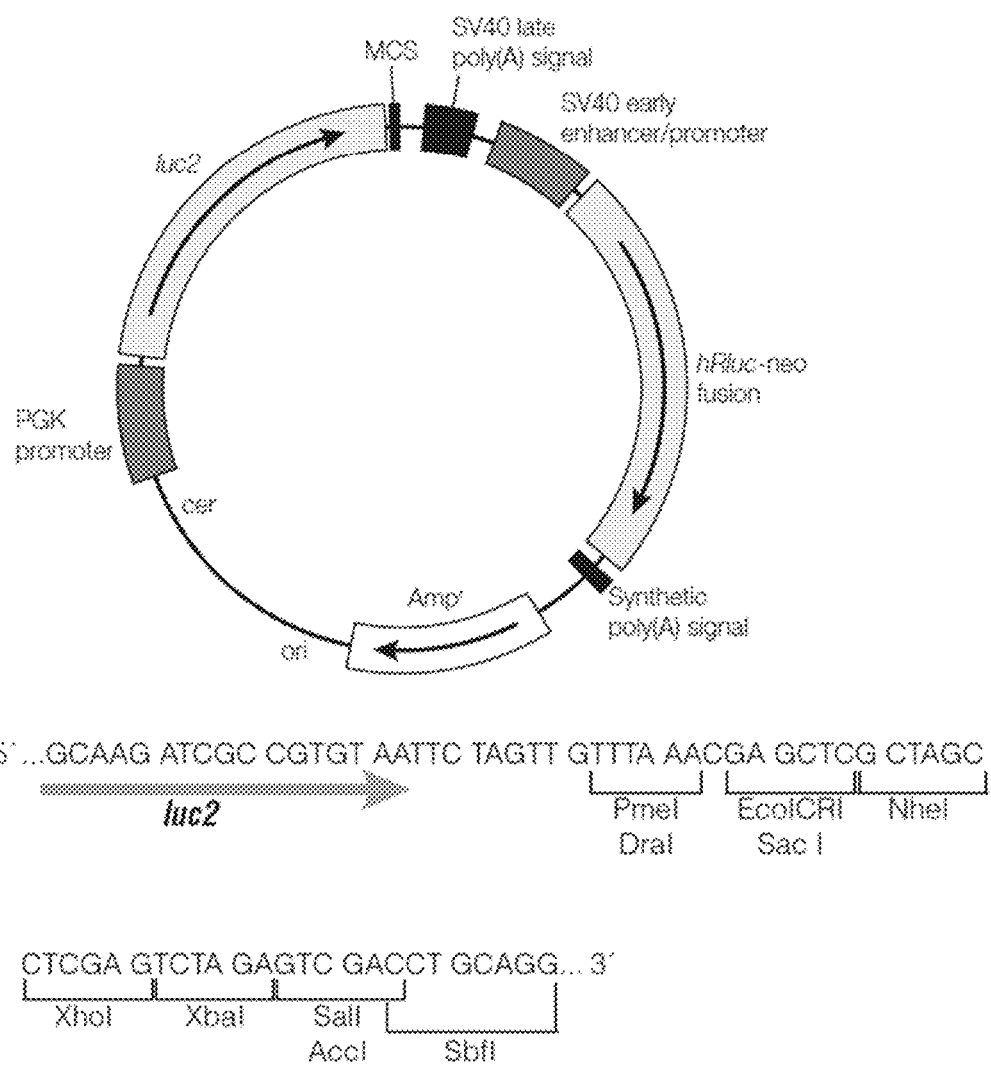
FIG. 2 shows the map of an overexpression vector for dual luciferase assay.
Figure 3:
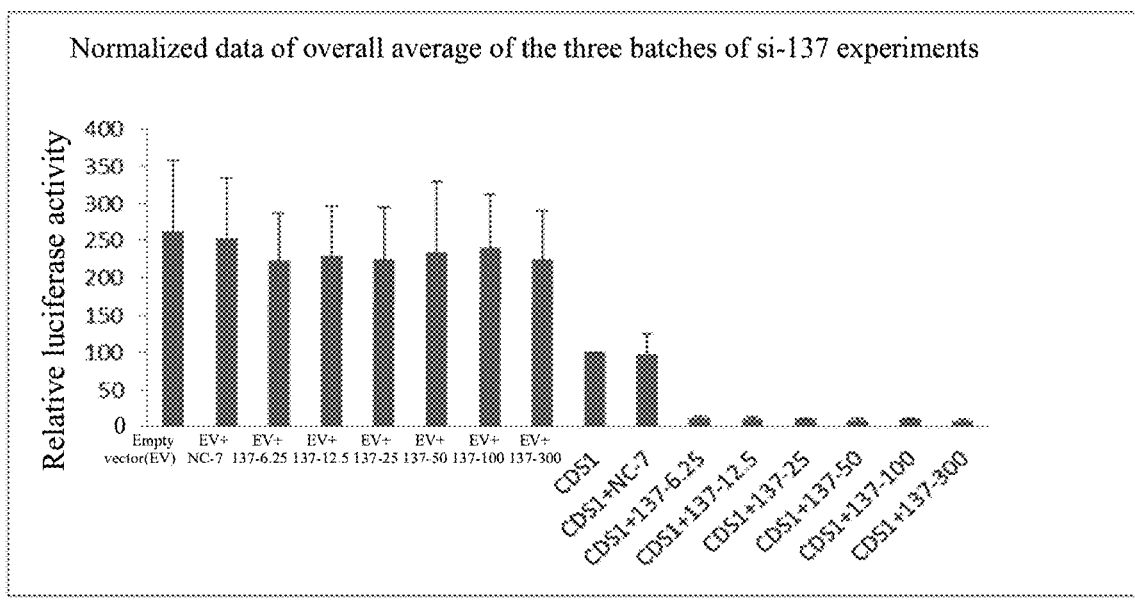
FIG. 3 shows the inhibitory effect of si-TD137 on CKIP-1 expression in a dual luciferase assay.
Figure 4:
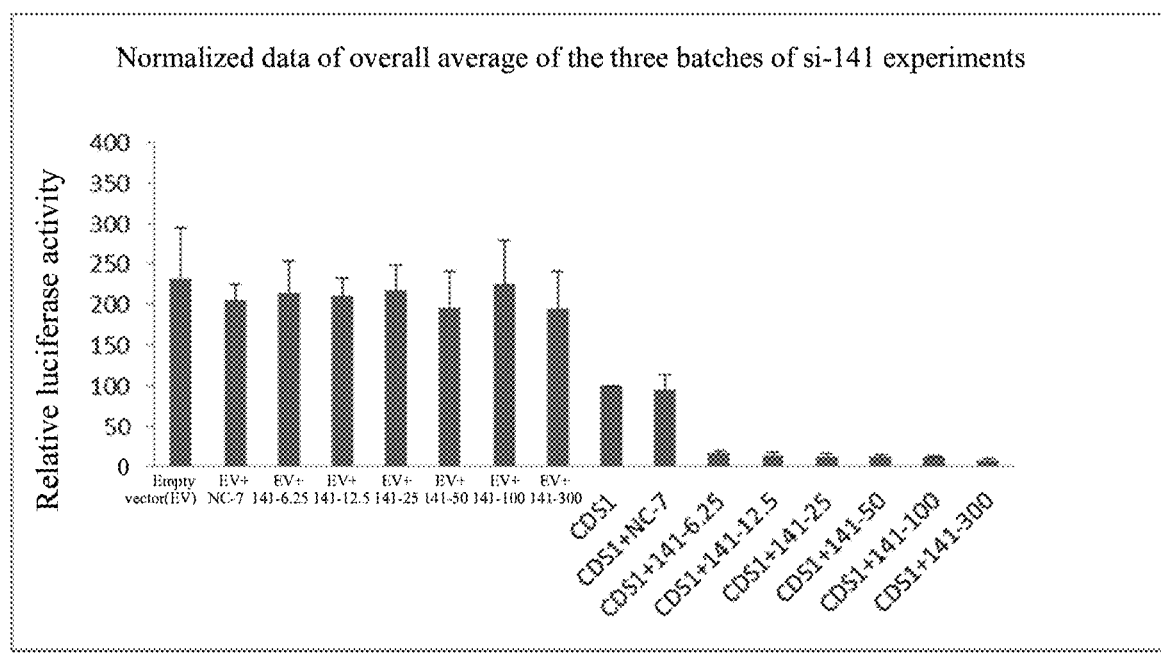
FIG. 4 shows the inhibitory effect of si-TD141 on CKIP-1 expression in a dual luciferase assay.
Figure 5:
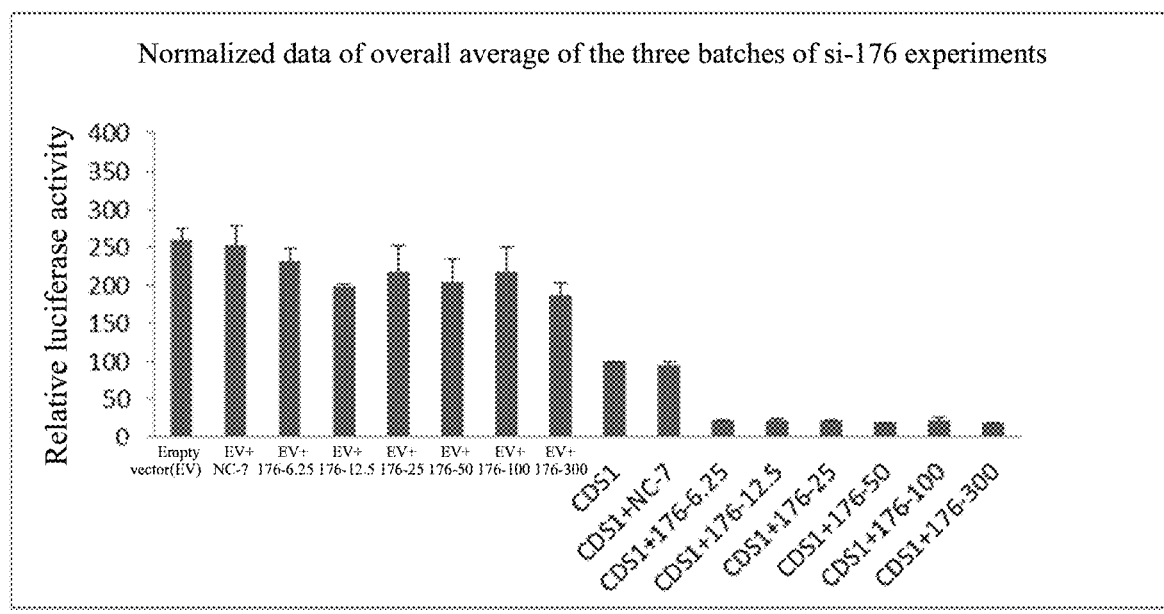
FIG. 5 shows the inhibitory effect of si-TD176 on CKIP-1 expression in a dual luciferase assay.
Figure 6:
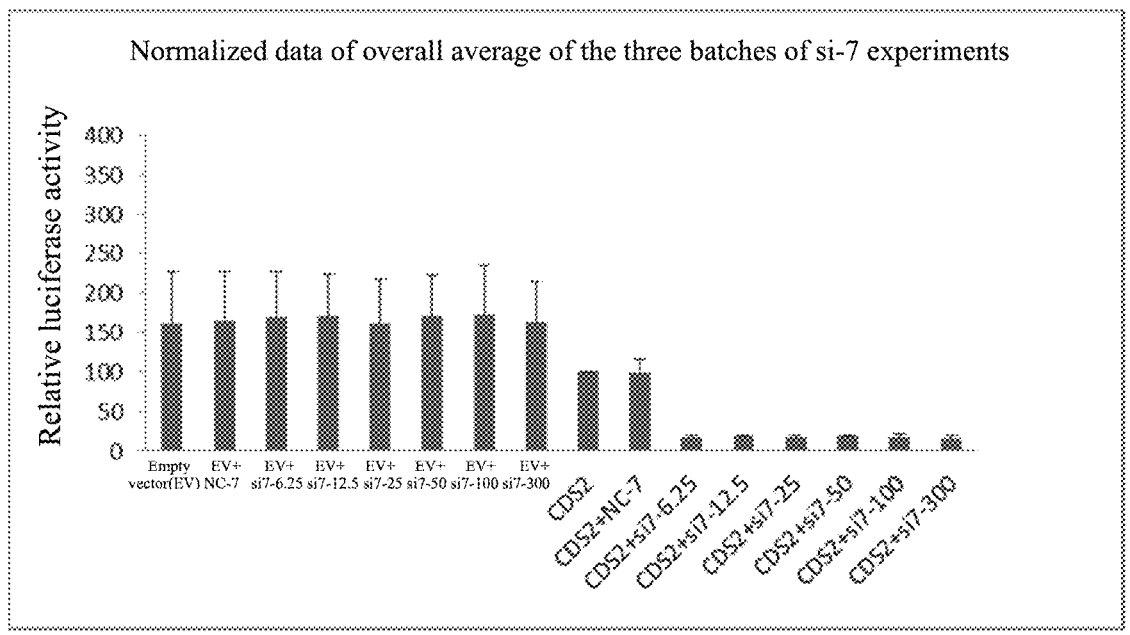
FIG. 6 shows the inhibitory effect of si-7 on CKIP-1 expression in a dual luciferase assay.

In the present invention, unless otherwise indicated, scientific and technical terms used herein have the meaning commonly understood by those skilled in the art. Moreover, the terms related to protein and nucleic acid chemistry, molecular biology, cell and tissue culture, microbiology, immunology, and laboratory procedures and routine procedures used herein are terms and procedures widely used in the relevant fields. Meanwhile, in order to better understand the present invention, definitions and explanations of related terms are provided below.

Unless otherwise indicated, the nucleic acid sequences recited herein are written in a direction from 5' to 3'. The term "nucleic acid" refers to DNA or RNA or modified forms thereof comprising purine or pyrimidine bases present in DNA (adenine "A", cytosine "C", guanine "G", thymine "T") or purine or pyrimidine bases present in RNA (adenine "A", cytosine "C", guanine "G", uracil "U"). The double-stranded RNA nucleic acid molecules provided herein may also comprise a "T" base at the 3' end, even if the "T" base is not naturally present in an RNA. In some cases, these bases may be denoted as "dT" to distinguish deoxyribonucleotides present in the ribonucleotide chain.

When a nucleic acid molecule selectively reduces or inhibits the expression of a gene, the gene is "targeted" by the nucleic acid molecule described herein. Alternatively, when a nucleic acid molecule hybridizes under stringent conditions to a transcript of a gene (i.e., mRNA thereof), the nucleic acid molecule targets the gene. Being capable of hybridizing "under stringent conditions" means annealing to the target mRNA region under standard conditions that tend to be detrimental to hybridization, e.g., high temperature and/or low salt content. Suitable processes, including 0.1× SSC, 68° C., 2 hours, are described in Molecular Cloning: A Laboratory Manual, Cold Spring Harbor Laboratory, 1982.

As used herein, "CKIP-1" refers to the CKIP-1 gene or protein (also known as PLEKHO1). Examples of the sequences of CKIP-1 include, but are not limited to: human: Genbank number NM_016274.4; mouse: Genbank number NM_023320.2; rat: Genbank number NM_001025119.1 and cynomolgus monkey: Genbank numbers XM001098879 and XM001098774.

As used herein, "target sequence" refers to a contiguous portion of the nucleotide sequence of an mRNA molecule formed during transcription of a CKIP-1 gene, including mRNA as an RNA processing product of a primary transcript.

As used herein and unless otherwise indicated, the term "complementary", when used to describe a relationship between a first nucleotide sequence and a second nucleotide sequence, refers to the ability of an oligonucleotide or polynucleotide comprising the first nucleotide sequence to hybridize under specific conditions to an oligonucleotide or polynucleotide comprising the second nucleotide sequence and form a duplex structure, as will be understood by those skilled in the art. For example, such conditions can be stringent conditions, wherein the stringent conditions can include: 400 mM NaCl, 40 mM PIPES pH 6.4, 1 mM EDTA at 50° C. or 70° C. for 12-16 hours followed by washing. Other conditions may also be used, such as physiologically relevant conditions that may be encountered in an organism. Those skilled in the art will be able to determine the set of conditions most appropriate for a test of complementarity of two sequences in accordance with the ultimate application of the hybridized nucleotides.

This includes base pairing of an oligonucleotide or polynucleotide comprising the first nucleotide sequence with an oligonucleotide or polynucleotide comprising the second nucleotide sequence over the full length of the first and second nucleotide sequences. These sequences may be referred to herein as being "completely complementary" to each other. However, when reference is made herein to the first sequence being "substantially complementary" to the second sequence, the two sequences may be completely complementary or form one or more, but typically no more than 4, 3 or 2, mismatched base pairs upon hybridization, while retaining the ability to hybridize under the conditions most relevant to their ultimate application. However, when two oligonucleotides are designed to form one or more single stranded overhangs upon hybridization, such overhangs should not be considered mismatches when referring to the definition of complementarity. For example, in a dsRNA comprising one oligonucleotide of 19 nucleotides in length and another oligonucleotide of 21 nucleotides in length, the longer oligonucleotide comprises a sequence of 19 nucleotides that is fully complementary to the shorter oligonucleotide, which may also be referred to as being "completely complementary".

"Complementary" sequences, as used herein, may also comprise or be entirely formed from non-Watson-Crick base pairs and/or base pairs formed from non-natural and modified nucleotides, as long as the above requirements regarding their ability to hybridize are met. These non-Watson-Crick base pairs include, but are not limited to, G:U Wobble or Hoogstein base pairing.

As used herein for base matching between the sense strand and the antisense strand of a dsRNA, or base matching between the antisense strand of a dsRNA and the target sequence, the terms "complementary", "fully complementary" and "substantially complementary" may be used, which are to be understood in accordance with the context.

As used herein, a polynucleotide that is "substantially complementary to at least a portion of" a messenger RNA (mRNA) refers to a polynucleotide that is substantially complementary to a contiguous portion of a target mRNA (e.g., an mRNA encoding CKIP-1) that includes a 5' UTR, an open reading frame (ORF), or a 3' UTR. For example, a polynucleotide is complementary to at least a portion of CKIP-1 if its sequence is substantially complementary to a non-interrupted portion of an mRNA encoding CKIP-1.

Recently, it has been found that double-stranded RNA molecules (dsRNA) block gene expression through a highly conserved regulatory mechanism known as RNA interference (RNAi). WO 99/32619 (Fire et al.) discloses the use of dsRNA of at least 25 nucleotides in length to inhibit *C. elegans* gene expression. dsRNA has also been found to degrade target RNA in other organisms including plants (see, e.g., WO 99/53050, Waterhouse et al., and WO 99/61631, Heifetz et al.), *Drosophila* (see, e.g., Yang, D., et al., Curr. Biol. (2000) 10: 1191-1200), and mammals (see WO 00/44895, Limmer and DE 10100586.5, Kreutzer et al.). This natural mechanism has become a hot spot in the development of new drugs for the treatment of diseases caused by abnormal or harmful regulation of genes.

As used herein, the term "double-stranded RNA" or "dsRNA" refers to a duplex structure comprising two antiparallel and substantially complementary nucleic acid strands as described above. Typically, the majority of the nucleotides of each strand are ribonucleotides, but as detailed herein, each strand or both strands may also comprise at least one non-ribonucleotide, such as a deoxyribonucleotide and/or a modified nucleotide. In addition, "dsRNA" as used in this specification may include chemical modifications to ribonucleotides, including modifications at multiple nucleotides, and includes all types of modifications disclosed herein or known in the art.

The two strands forming the duplex structure may be different portions of the same larger RNA molecule, or they may be separate RNA molecules. If the two strands are separate RNA molecules, such dsRNA is often referred to in the literature as siRNA ("short interfering RNA"). If the two strands are parts of a larger molecule and are joined by a non-interrupted nucleotide strand between the 3'-end of one strand and the 5'-end of the other strand forming the duplex structure, the joined RNA strand is referred to as a "hairpin loop", a "short hairpin RNA", or a "shRNA". If the two strands are covalently linked by means other than a non-interrupted strand between the 3'-end of one strand and the 5'-end of the other strand forming a duplex structure, the linkage structure is referred to as a "linker". The RNA strands may have the same or different number of nucleotides. In addition to the duplex structure, the dsRNA may comprise overhangs of one or more nucleotides. Typically, most of the nucleotides of each strand are ribonucleotides, but as described in detail herein, each strand or both strands may also comprise at least one non-ribonucleotide, for example, a deoxyribonucleotide and/or a modified nucleotide.

As used herein, "overhang" refers to one or more unpaired nucleotides that protrude from the duplex structure of a dsRNA when the 3' end of one strand of the dsRNA extends beyond the 5' end of the other strand or vice versa. "Blunt end" or "blunt-ended" means that there are no unpaired nucleotides at the end of the dsRNA, i.e., there are no nucleotide overhangs. A "blunt-ended" dsRNA refers to a dsRNA that is double-stranded over its entire length, i.e., without nucleotide overhang at either end of the molecule. For clarity, chemical caps or non-nucleotide chemical moieties coupled to the 3'- or 5'-ends of the dsRNA are not considered in determining whether the dsRNA has overhangs or blunt ends.

The term "antisense strand" refers to a strand of dsRNA comprising a region substantially complementary to a target sequence. As used herein, the term "complementary region" refers to a region of the antisense strand that is substantially complementary to a sequence as defined herein (e.g., a target sequence). If the complementary region is not fully complementary to the target sequence, the mismatch may be located in an internal or end region of the molecule. Typically, the most tolerable mismatch is located within the terminal regions (excluding overhangs described herein), e.g., within 6, 5, 4, 3 or 2 nucleotides from the 5' and/or 3' ends, or the last 1 nucleotide at the 5' and/or 3' ends.

As used herein, the term "sense strand" refers to a strand of dsRNA comprising a region substantially complementary to the region of the antisense strand.

The term "subject" or "individual" as used herein means a mammal, particularly a primate, particularly a human.

As used herein, "treating" an individual suffering from a disease or disease condition means that the individual's symptoms are partially or completely alleviated, or remain unchanged after treatment. Thus, treatment includes prevention, treatment and/or cure. Prevention refers to prevention of a potential disease and/or prevention of worsening of symptoms or disease progression. Treatment also includes any pharmaceutical uses of any dsRNA, expression vector, and composition provided herein.

As used herein, "therapeutic effect" means an effect resulting from treatment of an individual that alters, generally ameliorates or alleviates the symptoms of the disease or disease condition, or cures the disease or disease condition.

As used herein, "therapeutically effective amount" or "therapeutically effective dose" refers to an amount of a substance, compound, material, or composition comprising a compound that is at least sufficient to produce a therapeutic effect after administration to a subject. Thus, it is the amount necessary to prevent, cure, ameliorate, arrest or partially arrest the symptoms of the disease or condition. For example, if a given clinical treatment that decreases a measurable parameter associated with a disease or condition by at least 25% is considered to be an effective treatment, a therapeutically effective amount of the drug used to treat the disease or condition is the amount necessary to decrease the parameter by at least 25%.

The term "pharmaceutically acceptable carrier" refers to a carrier used to administer a therapeutic agent (e.g., dsRNA). Such carriers include, but are not limited to, saline, buffered saline solution, glucose, water, glycerol, ethanol, and combinations thereof.

As used herein, an "expression vector" includes a vector capable of expressing a nucleotide sequence of interest operably linked to regulatory sequences, such as promoter regions, capable of affecting expression of such nucleotide sequence. Such additional fragments may include promoter and terminator sequences, and optionally may include one or more origins of replication, one or more selectable markers, enhancers, polyadenylation signals, and the like.

As used herein, "operably linked" with respect to a nucleic acid sequence, region, element, or domain means that the nucleic acid regions are functionally related to each other. For example, a promoter may be operably linked to a nucleotide sequence encoding a dsRNA such that the promoter regulates or mediates transcription of the nucleotide sequence.

II. Nucleic Acid Molecules Targeting CKIP-1

The present inventors designed, synthesized and screened out dsRNA molecules capable of significantly inhibiting CKIP-1 expression. Surprisingly, the dsRNA molecules as obtained can both reduce inflammation and promote bone repair, and thus can be effectively used for treating arthritis, such as rheumatoid arthritis (RA).

In one aspect, the invention provides a nucleic acid molecule targeting CKIP-1, such as a dsRNA molecule, which comprises a sense strand and a corresponding complementary antisense strand selected from Table 1.

In some preferred embodiments, the CKIP-1-targeting nucleic acid molecule comprises a sense and an antisense strand corresponding to si-TD060, si-TD062, si-TD066, si-TD068, si-TD070, si-TD074, si-TD080, si-TD082, si-TD089, si-TD096, si-TD137, si-TD140, si-TD141, si-TD143, si-TD176, si-TD178, si-TD181, si-TD362, si-TD364, si-TD378, si-TD726, si-TD730, si-7, si-10 in Table 1.

In some more preferred embodiments, the nucleic acid molecule targeting CKIP-1 comprises a sense strand and an antisense strand corresponding to si-TD137, si-TD141, si-TD176, si-7 in Table 1

In some embodiments, the sense strand and/or the antisense strand of the nucleic acid molecule additionally has an overhang of at least one nucleotide at the 3' end. For example, the sense and/or antisense strand additionally has an overhang of 1, 2 or 3 nucleotides at the 3' end. For example, in some embodiments, the overhang is TT (i.e., dTdT). In some embodiments, the sense and antisense strands of the nucleic acid molecule comprise an additional overhang Ti' at the 3' end.

In some embodiments, the sense strand and/or the antisense strand in the nucleic acid molecule comprises at least 1, e.g., 1 or 2 nucleotide substitutions. For example, the substitution is located within 6, 5, 4, 3 or 2 nucleotides from the 5' and/or 3' ends. In some embodiments, the sense and antisense strands of the nucleic acid molecule comprise 1 nucleotide substitution at the 3' last nucleotide position of the sense strand and correspondingly at the 5' first nucleotide position of the antisense strand. Such substitutions may result in mismatches with the target sequence, however mismatches as defined herein are tolerated, without significantly affecting or without affecting the activity of the dsRNA.

In some embodiments, the dsRNA of the present invention comprises at least one modified nucleotide. The modified nucleotide may comprise modification of the phosphate group, the ribose group and/or the base group.

For example, modification of the phosphate group in a nucleotide includes modification of the oxygen in the phosphate group, such as phosphorothioate modification and boranophosphate modification. The oxygen in the phosphate group is substituted with sulfur and borane, respectively, as shown in the following formula. Both modifications stabilize the nucleic acid structure and maintain high specificity and affinity for base pairing.

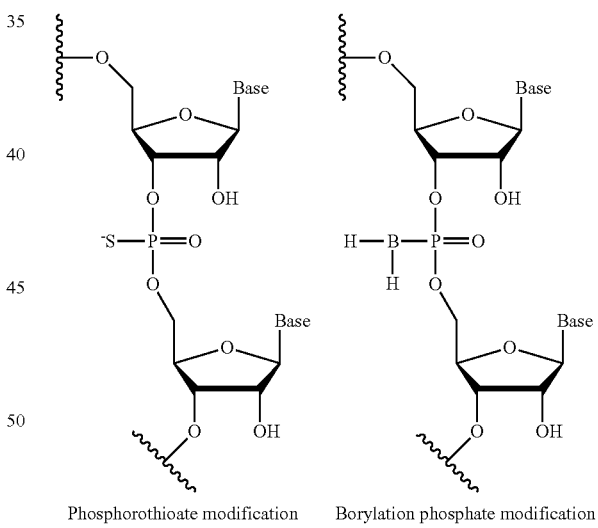

Phosphorothioate modification     Borylation phosphate modification

Modification of the ribose group in a nucleotide includes modification of the 2'-hydroxyl group (2'-OH) in the ribose group. During RNA hydrolysis, under the catalysis of RNase, 2'-OH first attacks the phosphate group, forms a cyclic phosphodiester while breaking a phosphate ester bond, and then forms the hydrolysates under the action of alkali. If certain substituents such as methoxy group or fluorine group are introduced into the 2'-hydroxyl position of the ribose group, the nucleic acid such as siRNA may have stronger nuclease hydrolysis resistance, and the stability of the nucleic acid is improved. Modifications to the 2'-hydroxyl group of the nucleotide pentose include, but are not limited to, 2'-fluoro modification, 2'-methoxy modification (2'-OME), 2'-methoxy ethyl modification (2'-MOE), 2'-2,4-dinitrophenol modification (2'-DNP modification), Locked nucleic acid modification (LNA modification), 2'-Amino modification, 2'-Deoxy modification, 3'-Cholesterol modification, 4'-thiothymidine modification, and the like. Examples of structures for such modifications are as follows:

from the group consisting of: 2'-O-methyl modified nucleotides, 2'-F modified nucleotides, nucleotides comprising a 5'-phosphorothioate group, and end nucleotides linked to a cholesteryl derivative or dodecanoic acid bisdecylamide group, and/or, for example, the modified nucleotides are selected from the group consisting of: 2'-deoxy-2'-fluoro modified nucleotides, 2'-deoxy-modified nucleotides, locked nucleotides, abasic nucleotides, 2'-amino-modified nucleo-

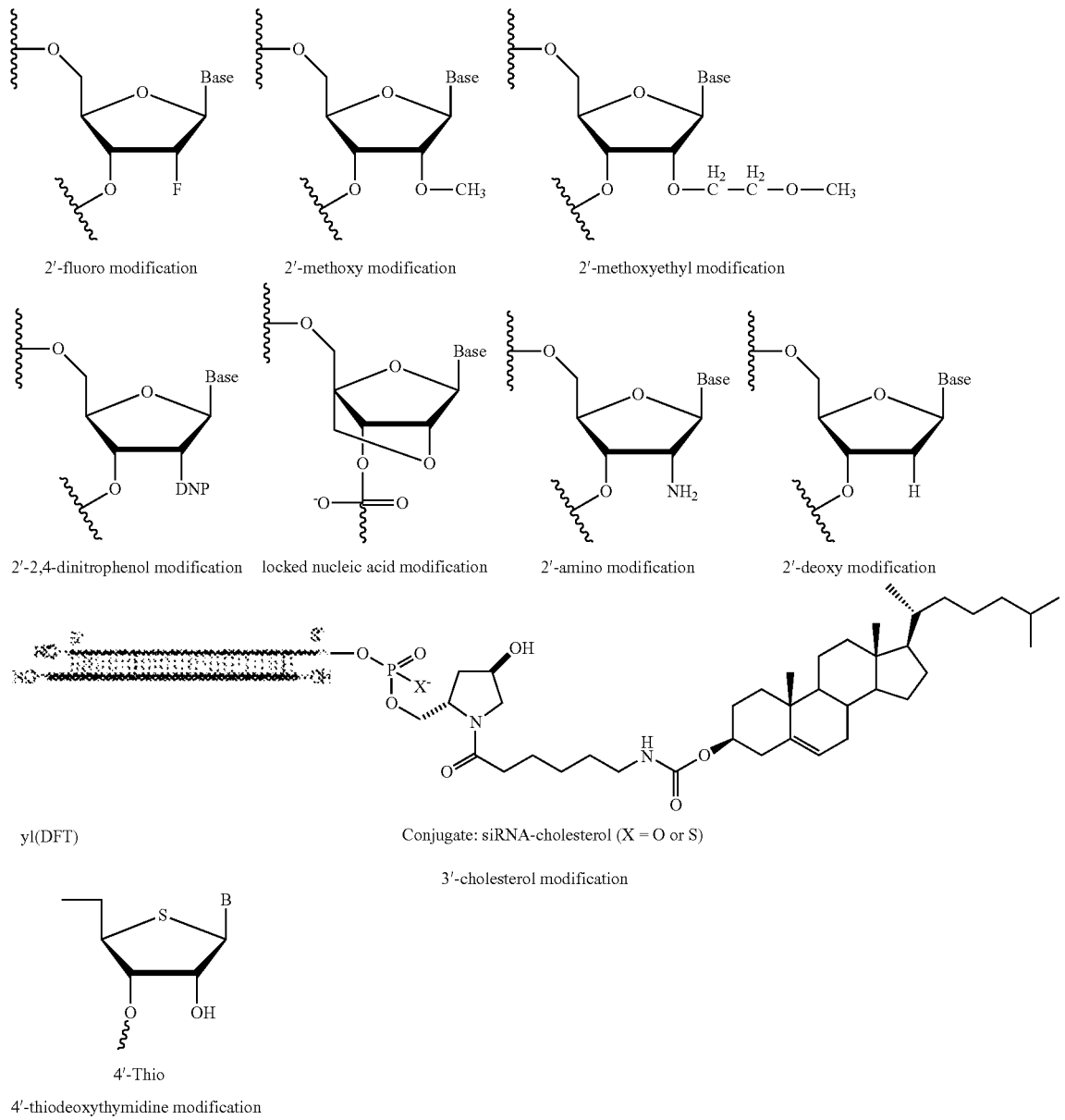

4'-thiodeoxythymidine modification

The modification of the base group in the nucleotide refers to modifying the base in the nucleotide group to enhance the interaction between bases, so as to improve the effect on the target mRNA. For example, 5'-bromouracil and 5'-iodouracil modifications, which introduce bromine or iodine at the 5' position of uracil, are commonly used base modifications. Other modifications include N3-methyl-uracil modification, 2,6-diaminopurine modification, etc.

In some embodiments, the dsRNA of the present invention comprises at least one modified nucleotide selected tides, 2'-alkyl-modified nucleotides, morpholino nucleotides, phosphoramidates, and nucleotides containing unnatural bases. The at least one modified nucleotide may, for example, enhance the stability of the dsRNA and/or reduce the immunogenic effect of the dsRNA. The modified nucleotides may be on the sense strand and/or on the antisense strand.

In some embodiments, the dsRNA comprises at least one 2'-O-methyl modified ribonucleotide and/or at least one nucleotide comprising a 5'-phosphorothioate group.

In some specific embodiments, the 2' hydroxyl groups of all nucleotides with uracil or cytosine bases in the sense and/or antisense strands of the dsRNA of the present invention are modified with methoxy groups.

In some embodiments, the 2' hydroxyl groups of all nucleotides with uracil or cytosine bases in the sense strand of the dsRNA of the present invention are modified with methoxy groups.

In some embodiments, the 2' hydroxyl groups of all nucleotides in the sense and/or antisense strands of the dsRNA of the present invention are modified with methoxy groups.

In some embodiments, the 2' hydroxyl groups of all nucleotides in the sense strand of the dsRNA of the invention are modified with methoxy groups.

In some embodiments, the 5' end of the sense strand and/or the antisense strand of the dsRNA of the invention is phosphorylated.

In some embodiments, the sense strand and/or the antisense strand of the dsRNA of the present invention comprises a 3' cholesterol modification.

In some embodiments, the 2' hydroxyl groups of all the nucleotides with uracil bases or cytosine bases in the sense strand of the dsRNA of the present invention are modified with fluorine (F).

In some embodiments, the dsRNA of the invention comprises a locked nucleic acid modification in the sense strand.

In some embodiments, all nucleotides in the sense strand and/or antisense strand of the dsRNA of the invention comprise phosphorothioate modifications.

In some embodiments, the dsRNA molecule is an siRNA.

In still other embodiments, the dsRNA molecule is shRNA (short hairpin RNA). It is within the ability of those skilled in the art to design suitable shRNAs based on siRNA sequences.

The dsRNA of the present invention may be obtained by conventional techniques in the art such as solid phase synthesis or liquid phase synthesis. Modified nucleotides can be introduced by using modified nucleotide monomers during the synthesis.

In yet another aspect, the invention provides an expression vector comprising a nucleotide sequence encoding a nucleic acid molecule of the invention, such as dsRNA, wherein the nucleotide sequence is operably linked to a transcription regulatory element, such as a promoter or the like. Recombinant vector capable of expressing a dsRNA molecule can be delivered to and permanently present in the target cells. Alternatively, a vector providing transient expression of the nucleic acid molecule may be used. If desired, the vector may be administered repeatedly. Once expressed, the dsRNA molecule interacts with the target mRNA and generates an RNA interference response. In general, shRNAs are particularly suitable for being produced in this manner.

The expression vector may be a linear construct, a circular plasmid vector, or a viral vector (including but not limited to adenovirus, adeno-associated virus, lentiviral vector, etc.). In the case of siRNA, individual strands of siRNA can be transcribed from promoters on two separate expression vectors; alternatively, individual strands of siRNA may be transcribed from promoters both located on the same expression plasmid. In the case of shRNA, the shRNA strand is transcribed from a single expression vector.

The promoter driving dsRNA expression in the expression vector of the present invention may be eukaryotic RNA polymerase I promoter (e.g., ribosomal RNA promoter), RNA polymerase II promoter (e.g., CMV early promoter or actin promoter or U1snRNA promoter) or generally RNA polymerase III promoter (e.g., U6snRNA or 7SKRNA promoter) or prokaryotic promoter (e.g., T7 promoter, provided that the expression vector also encodes the T7 RNA polymerase required for transcription from the T7 promoter).

The dsRNA of the present invention can significantly inhibit the expression of CKIP-1 in cells. In some embodiments, expression of CKIP-1 is inhibited by at least 50%, at least 55%, at least 60%, at least 65%, at least 70%, at least 75%, at least 80%, at least 85%, at least 90%, at least 95%, or even 100%. Preferably, the dsRNA of the present invention is capable of inhibiting CKIP-1 expression by at least 50%. More preferably, the dsRNA of the present invention is capable of inhibiting CKIP-1 expression by at least 70%.

When the terms "inhibit the expression of", "downregulate the expression of", "suppress the expression of", and the like are used in reference to a CKIP-1 gene, they refer herein to the at least partial inhibition of the expression of the CKIP-1 gene, as manifested by a decrease in the level of CKIP-1 expression in a first cell or group of cells in which the CKIP-1 gene is transcribed and which has or have been treated such that the expression of the CKIP-1 gene is inhibited, as compared to a second cell or group of cells substantially identical to the first cell or group of cells but which has or have not been so treated (control cells). The degree of inhibition is usually expressed in the following way:

(CKIP-1 expression level in control cells−CKIP-1 expression level in treated cells)/CKIP-1 expression level in control cells×100%.

The expression level may be an mRNA level or a protein level. It is clear to those skilled in the art how to determine the mRNA level or the corresponding protein level of a particular gene.

Surprisingly, the dsRNA of the present invention may also inhibit the expression of the pro-inflammatory cytokines IL-6, TNF-α and/or IL-17A. In particular, the dsRNA of the present invention can significantly inhibit the expression of the pro-inflammatory cytokine IL-6.

In some embodiments, expression of the pro-inflammatory cytokines IL-6, TNF-α, and/or IL-17A is inhibited by at least 10%, at least 20%, at least 30%, at least 40%, at least 50%, at least 60%, at least 70%, at least 80%, at least 90%, or even 100%. In some preferred embodiments, the expression of IL-6 is inhibited by at least 50%, more preferably by at least 80%.

TABLE 1 dsRNA inhibiting CKIP-1 expression

| siRNA | Sequence (5'-3') | | SEQ ID NO |
|---|---|---|---|
| si-TD037 | Sense strand | AAGGUCGGCUGGGUCCGGA | 1 |
| | Antisense strand | UCCGGACCCAGCCGACCUU | 2 |
| si-TD040 | Sense strand | GUCGGCUGGGUCCGGAAAU | 3 |
| | Antisense strand | AUUUCCGGACCCAGCCGAC | 4 |
| si-TD042 | Sense strand | CGGCUGGGUCCGGAAAUUC | 5 |
| | Antisense strand | GAAUUUCCGGACCCAGCCG | 6 |
| si-TD044 | Sense strand | GCUGGGUCCGGAAAUUCUG | 7 |
| | Antisense strand | CAGAAUUUCCGGACCCAGC | 8 |
| si-TD050 | Sense strand | UCCGGAAAUUCUGCGGGAA | 9 |
| | Antisense strand | UUCCCGCAGAAUUUCCGGA | 10 |

TABLE 1-continued dsRNA inhibiting CKIP-1 expression

| siRNA | | Sequence (5'-3') | SEQ ID NO |
|---|---|---|---|
| si-TD057 | Sense strand | AUUCUGCGGGAAAGGGAUU | 11 |
| | Antisense strand | AAUCCCUUUCCCGCAGAAU | 12 |
| si-TD058 | Sense strand | UUCUGCGGGAAAGGGAUUU | 13 |
| | Antisense strand | AAAUCCCUUUCCCGCAGAA | 14 |
| si-TD060 | Sense strand | CUGCGGGAAAGGGAUUUUC | 15 |
| | Antisense strand | GAAAAUCCCUUUCCCGCAG | 16 |
| si-TD061 | Sense strand | UGCGGGAAAGGGAUUUUCA | 17 |
| | Antisense strand | UGAAAAUCCCUUUCCCGCA | 18 |
| si-TD062 | Sense strand | GCGGGAAAGGGAUUUUCAG | 19 |
| | Antisense strand | CUGAAAAUCCCUUUCCCGC | 20 |
| si-TD064 | Sense strand | GGGAAAGGGAUUUUCAGGG | 21 |
| | Antisense strand | CCCUGAAAAUCCCUUUCCC | 22 |
| si-TD065 | Sense strand | GGAAAGGGAUUUUCAGGGA | 23 |
| | Antisense strand | UCCCUGAAAAUCCCUUUCC | 24 |
| si-TD066 | Sense strand | GAAAGGGAUUUUCAGGGAG | 25 |
| | Antisense strand | CUCCCUGAAAAUCCCUUUC | 26 |
| si-TD067 | Sense strand | AAAGGGAUUUUCAGGGAGA | 27 |
| | Antisense strand | UCUCCCUGAAAAUCCCUUU | 28 |
| si-TD068 | Sense strand | AAGGGAUUUUCAGGGAGAU | 29 |
| | Antisense strand | AUCUCCCUGAAAAUCCCUU | 30 |
| si-TD070 | Sense strand | GGGAUUUUCAGGGAGAUUU | 31 |
| | Antisense strand | AAAUCUCCCUGAAAAUCCC | 32 |
| si-TD072 | Sense strand | GAUUUUCAGGGAGAUUUGG | 33 |
| | Antisense strand | CCAAAUCUCCCUGAAAAUC | 34 |
| si-TD074 | Sense strand | UUUUCAGGGAGAUUUGGAA | 35 |
| | Antisense strand | UUCCAAAUCUCCCUGAAAA | 36 |
| si-TD076 | Sense strand | UUCAGGGAGAUUUGGAAAA | 37 |
| | Antisense strand | UUUUCCAAAUCUCCCUGAA | 38 |
| si-TD078 | Sense strand | CAGGGAGAUUUGGAAAAAC | 39 |
| | Antisense strand | GUUUUUCCAAAUCUCCCUG | 40 |
| si-TD080 | Sense strand | GGGAGAUUUGGAAAAACCG | 41 |
| | Antisense strand | CGGUUUUUCCAAAUCUCCC | 42 |
| si-TD082 | Sense strand | GAGAUUUGGAAAAACCGCU | 43 |
| | Antisense strand | AGCGGUUUUUCCAAAUCUC | 44 |
| si-TD084 | Sense strand | GAUUUGGAAAAACCGCUAU | 45 |
| | Antisense strand | AUAGCGGUUUUUCCAAAUC | 46 |
| si-TD087 | Sense strand | UUGGAAAAACCGCUAUGUG | 47 |
| | Antisense strand | CACAUAGCGGUUUUUCCAA | 48 |
| si-TD089 | Sense strand | GGAAAAACCGCUAUGUGGU | 49 |
| | Antisense strand | ACCACAUAGCGGUUUUUCC | 50 |
| si-TD093 | Sense strand | AAACCGCUAUGUGGUGCUG | 51 |
| | Antisense strand | CAGCACCACAUAGCGGUUU | 52 |
| si-TD094 | Sense strand | AACCGCUAUGUGGUGCUGA | 53 |
| | Antisense strand | UCAGCACCACAUAGCGGUU | 54 |
| si-TD096 | Sense strand | CCGCUAUGUGGUGCUGAAA | 55 |
| | Antisense strand | UUUCAGCACCACAUAGCGG | 56 |
| si-TD097 | Sense strand | CGCUAUGUGGUGCUGAAAG | 57 |
| | Antisense strand | CUUUCAGCACCACAUAGCG | 58 |
| si-TD098 | Sense strand | GCUAUGUGGUGCUGAAAGG | 59 |
| | Antisense strand | CCUUUCAGCACCACAUAGC | 60 |
| si-TD136 | Sense strand | GAGAAGGAGGUAAAAGAUG | 61 |
| | Antisense strand | CAUCUUUUACCUCCUUCUC | 62 |
| si-TD137 | Sense strand | AGAAGGAGGUAAAAGAUGA | 63 |
| | Antisense strand | UCAUCUUUUACCUCCUUCU | 64 |
| si-TD138 | Sense strand | GAAGGAGGUAAAAGAUGAG | 65 |
| | Antisense strand | CUCAUCUUUUACCUCCUUC | 66 |
| si-TD139 | Sense strand | AAGGAGGUAAAAGAUGAGA | 67 |
| | Antisense strand | UCUCAUCUUUUACCUCCUU | 68 |
| si-TD140 | Sense strand | AGGAGGUAAAAGAUGAGAA | 69 |
| | Antisense strand | UUCUCAUCUUUUACCUCCU | 70 |
| si-TD141 | Sense strand | GGAGGUAAAAGAUGAGAAA | 71 |
| | Antisense strand | UUUCUCAUCUUUUACCUCC | 72 |
| si-TD143 | Sense strand | AGGUAAAAGAUGAGAAAAA | 73 |
| | Antisense strand | UUUUUCUCAUCUUUUACCU | 74 |
| si-TD181 | Sense strand | CUGAGUGACUAUGAGAAGU | 75 |
| | Antisense strand | ACUUCUCAUAGUCACUCAG | 76 |
| si-TD179 | Sense strand | ACCUGAGUGACUAUGAGAA | 77 |
| | Antisense strand | UUCUCAUAGUCACUCAGGU | 78 |
| si-TD178 | Sense strand | GACCUGAGUGACUAUGAGA | 79 |
| | Antisense strand | UCUCAUAGUCACUCAGGUC | 80 |
| si-TD177 | Sense strand | UGACCUGAGUGACUAUGAG | 81 |
| | Antisense strand | CUCAUAGUCACUCAGGUCA | 82 |
| si-TD176 | Sense strand | UUGACCUGAGUGACUAUGA | 83 |
| | Antisense strand | UCAUAGUCACUCAGGUCAA | 84 |
| si-TD224 | Sense strand | GCAGGAGCAAGAAAAAUCA | 85 |
| | Antisense strand | UGAUUUUCUUGCUCCUGC | 86 |
| si-TD221 | Sense strand | AGAGCAGGAGCAAGAAAAA | 87 |
| | Antisense strand | UUUUUCUUGCUCCUGCUCU | 88 |
| si-TD217 | Sense strand | UCCAAGAGCAGGAGCAAGA | 89 |
| | Antisense strand | UCUUGCUCCUGCUCUUGGA | 90 |
| si-TD380 | Sense strand | UGAGGAGGACAGCUAUCUU | 91 |
| | Antisense strand | AAGAUAGCUGUCCUCCUCA | 92 |
| si-TD378 | Sense strand | GUUGAGGAGGACAGCUAUC | 93 |
| | Antisense strand | GAUAGCUGUCCUCCUCAAC | 94 |
| si-TD376 | Sense strand | CCGUUGAGGAGGACAGCUA | 95 |
| | Antisense strand | UAGCUGUCCUCCUCAACGG | 96 |
| si-TD372 | Sense strand | GUCACCGUUGAGGAGGACA | 97 |
| | Antisense strand | UGUCCUCCUCAACGGUGAC | 98 |
| si-TD370 | Sense strand | AGGUCACCGUUGAGGAGGA | 99 |
| | Antisense strand | UCCUCCUCAACGGUGACCU | 100 |
| si-TD364 | Sense strand | UGGAUGAGGUCACCGUUGA | 101 |
| | Antisense strand | UCAACGGUGACCUCAUCCA | 102 |
| si-TD362 | Sense strand | CUUGGAUGAGGUCACCGUU | 103 |
| | Antisense strand | AACGGUGACCUCAUCCAAG | 104 |
| si-TD358 | Sense strand | GUAUCUUGGAUGAGGUCAC | 105 |
| | Antisense strand | GUGACCUCAUCCAAGAUAC | 106 |
| si-TD451 | Sense strand | AGGAAGACCCUUCCCCUGA | 107 |
| | Antisense strand | UCAGGGGAAGGGUCUUCCU | 108 |

TABLE 1-continued dsRNA inhibiting CKIP-1 expression

| siRNA | Sequence (5'-3') | | SEQ ID NO |
|---|---|---|---|
| si-TD443 | Sense strand | GAUCCAAGAGGAAGACCCU | 109 |
| | Antisense strand | AGGGUCUUCCUCUUGGAUC | 110 |
| si-TD509 | Sense strand | GGACAAGUCUGUGGCCCAG | 111 |
| | Antisense strand | CUGGGCCACAGACUUGUCC | 112 |
| si-TD508 | Sense strand | UGGACAAGUCUGUGGCCCA | 113 |
| | Antisense strand | UGGGCCACAGACUUGUCCA | 114 |
| si-TD577 | Sense strand | GCCUCCCUGGAGGAGAUCC | 115 |
| | Antisense strand | GGAUCUCCUCCAGGGAGGC | 116 |
| si-TD611 | Sense strand | GGUAGCAAGGAAACUGGAG | 117 |
| | Antisense strand | CUCCAGUUUCCUUGCUACC | 118 |
| si-TD609 | Sense strand | CUGGUAGCAAGGAAACUGG | 119 |
| | Antisense strand | CCAGUUUCCUUGCUACCAG | 120 |
| si-TD607 | Sense strand | ACCUGGUAGCAAGGAAACU | 121 |
| | Antisense strand | AGUUUCCUUGCUACCAGGU | 122 |
| si-TD604 | Sense strand | AGGACCUGGUAGCAAGGAA | 123 |
| | Antisense strand | UUCCUUGCUACCAGGUCCU | 124 |
| si-TD600 | Sense strand | AUCCAGGACCUGGUAGCAA | 125 |
| | Antisense strand | UUGCUACCAGGUCCUGGAU | 126 |
| si-TD598 | Sense strand | GGAUCCAGGACCUGGUAGC | 127 |
| | Antisense strand | GCUACCAGGUCCUGGAUCC | 128 |
| si-TD596 | Sense strand | CCGGAUCCAGGACCUGGUA | 129 |
| | Antisense strand | UACCAGGUCCUGGAUCCGG | 130 |
| si-TD588 | Sense strand | CAGCUGUCCCGGAUCCAGG | 131 |
| | Antisense strand | CCUGGAUCCGGGACAGCUG | 132 |
| si-TD587 | Sense strand | GCAGCUGUCCCGGAUCCAG | 133 |
| | Antisense strand | CUGGAUCCGGGACAGCUGC | 134 |
| si-TD585 | Sense strand | GGGCAGCUGUCCCGGAUCC | 135 |
| | Antisense strand | GGAUCCGGGACAGCUGCCC | 136 |
| si-TD720 | Sense strand | GAGCUGAGAGACCUGUACA | 137 |
| | Antisense strand | UGUACAGGUCUCUCAGCUC | 138 |
| si-TD718 | Sense strand | GGGAGCUGAGAGACCUGUA | 139 |
| | Antisense strand | UACAGGUCUCUCAGCUCCC | 140 |
| si-TD743 | Sense strand | GACUCCACCUCAGACAGA | 141 |
| | Antisense strand | UCUGUCUGAGGUGGGAGUC | 142 |
| si-TD145 | Sense strand | GUAAAAGAUGAGAAAAAUA | 143 |
| | Antisense strand | UAUUUUUCUCAUCUUUUAC | 144 |
| si-TD480 | Sense strand | UCUUGUGCUGAGAGCUUUC | 145 |
| | Antisense strand | GAAAGCUCUCAGCACAAGA | 146 |
| si-TD483 | Sense strand | UGUGCUGAGAGCUUUCGGG | 147 |
| | Antisense strand | CCCGAAAGCUCUCAGCACA | 148 |
| si-TD736 | Sense strand | ACAGACAGAUGGACCUGCA | 149 |
| | Antisense strand | UGCAGGUCCAUCUGUCUGU | 150 |
| si-TD734 | Sense strand | GUACAGACAGAUGGACCUG | 151 |
| | Antisense strand | CAGGUCCAUCUGUCUGUAC | 152 |
| si-TD730 | Sense strand | ACCUGUACAGACAGAUGGA | 153 |
| | Antisense strand | UCCAUCUGUCUGUACAGGU | 154 |
| si-TD726 | Sense strand | AGAGACCUGUACAGACAGA | 155 |
| | Antisense strand | UCUGUCUGUACAGGUCUCU | 156 |
| si-TD723 | Sense strand | CUGAGAGACCUGUACAGAC | 157 |
| | Antisense strand | GUCUGUACAGGUCUCUCAG | 158 |
| si-TD717 | Sense strand | AGGGAGCUGAGAGACCUGU | 159 |
| | Antisense strand | ACAGGUCUCUCAGCUCCCU | 160 |
| si-7 | Sense strand | UGGGAGAUGGGAAGCGAAA | 161 |
| | Antisense strand | UUUCGCUUCCCAUCUCCCA | 162 |
| si-10 | Sense strand | CAGACAAAGGGGCCACCUA | 163 |
| | Antisense strand | UAGGUGGCCCCUUUGUCUG | 164 |
| si-1 | Sense strand | GGACCUGGUAGCAAGGAAA | 165 |
| | Antisense strand | UUUCCUUGCUACCAGGUCC | 166 |

III. Pharmaceutical Compositions

In yet another aspect, the present invention provides a pharmaceutical composition comprising at least one dsRNA of the present invention or expression vector comprising a nucleotide sequence encoding the dsRNA, and a pharmaceutically acceptable carrier. In some embodiments, the pharmaceutical compositions are used for treating inflammatory diseases, such as arthritis, particularly rheumatoid arthritis (RA).

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal, intraarticular or epidermal administration (e.g., by injection or infusion). Depending on the route of administration, the active compound, i.e., the dsRNA molecule, can be encapsulated in a material, such as a liposome, to protect the compound from acids and other natural conditions that inactivate the compound. In some embodiments, the dsRNA of the present invention may be delivered by a cationic liposome delivery system.

The pharmaceutical compositions of the present invention may also contain pharmaceutically acceptable antioxidants. Examples of pharmaceutically acceptable antioxidants include: (1) Water-soluble antioxidants such as ascorbic acid. cysteine hydrochloride, sodium bisulfate, sodium metabisulfite, sodium sulfite and the like; (2) Oil-soluble antioxidants such as ascorbyl palmitate, butylated hydroxyanisole (BHA), butylated hydroxytoluene (BHT), lecithin, propyl gallate, α-tocopherol and the like; and (3) metal chelating agents such as citric acid, ethylenediaminetetraacetic acid (EDTA), sorbitol, tartaric acid, phosphoric acid and the like.

Such compositions may also contain, for example, preservatives, wetting agents, emulsifying agents and dispersing agents.

Prevention of the presence of microorganisms can be ensured by sterilization procedures or by the inclusion of various antibacterial and antifungal agents such as parabens, chlorobutanol, phenol sorbic acid, and the like. In many cases, it is preferred to include isotonic agents, for example, sugars, polyalcohols such as mannitol, sorbitol, or sodium oxide in the composition. Prolonged absorption of the injectable pharmaceutical can be realized by adding to the composition of absorption delaying agents, for example, monostearate salts and gelatin.

Pharmaceutically acceptable carriers include sterile aqueous solutions or dispersions and powders for the extemporaneous preparation of sterile injectable solutions or dispersions. The use of such media and agents for pharmaceutically active substances is well known in the art. Conventional media or agents, other than any range incompatible with the active compound, may be present in the pharmaceutical composition of the present invention. Additional active compounds may also be incorporated into the compositions.

Generally, therapeutic compositions must be sterile and stable under the conditions of manufacture and storage. The compositions may be formulated as solutions, microemulsions, liposomes or other ordered structures suitable for high drug concentrations. The carrier can be a solvent or dispersion containing, for example, water, ethanol, polyol (for example, glycerol, propylene glycol, and liquid polyethylene glycol, and the like), and suitable mixtures thereof. Proper fluidity can be maintained, for example, by the use of a coating such as lecithin, by the maintenance of the required particle size in the case of dispersion and by the use of surfactants.

Sterile injectable solutions can be prepared by incorporating the active compound in the required amount in a suitable solvent with one or a combination of ingredients enumerated above, as required, followed by sterile microfiltration. Generally, dispersions are prepared by incorporating the active compound into a sterile carrier which contains a basic dispersion medium and the other required ingredients from those enumerated above. For sterile powders for the preparation of sterile injectable solutions, the preferred methods of preparation are drying under vacuum and freeze-drying (lyophilization) which yields a powder of the active ingredient plus any additional desired ingredient from a previously sterile-filtered solution thereof.

The amount of active ingredient that can be combined with the carrier materials to produce a single dosage form will vary depending upon the subject being treated and the particular mode of administration. The amount of active ingredient that can be combined with the carrier materials to produce a single dosage form will generally be that amount of the composition which produces a therapeutic effect. Typically, this amount ranges from about 0.01% to about 99% active ingredient, e.g., from about 0.1% to about 70%, e.g., from about 1% to about 30% active ingredient, on a 100% basis, in combination with a pharmaceutically acceptable carrier.

The dosage regimen can be adjusted to provide the optimal desired response (e.g., therapeutic response). For example, a single bolus may be administered, several divided doses may be administered over time, or the dose may be proportionally reduced or increased as required by the exigencies of the therapeutic situation. It is particularly advantageous to formulate parenteral compositions in dosage unit form for ease of administration and uniformity of dosage. Dosage unit form as used herein refers to physically discrete units suited as unitary dosages for the subject to be treated; each unit contains a predetermined amount of active compound calculated to produce the desired therapeutic effect in combination with the required pharmaceutical carrier. The specific description of the dosage unit forms of the invention are dictated by and directly dependent on (a) the unique characteristics of the active compound and the particular therapeutic effect to be achieved, and (b) the limitations inherent in the art for formulating such active compounds for the treatment of sensitivity in individuals.

For administration of the dsRNA molecules of the present invention, the dosage may range from about 0.0000001 to 100 mg/kg body weight of the recipient. An exemplary treatment regimen may be once a week, once every two weeks, once every three weeks, once every four weeks, once a month, once every two months, once every three months, once every four months, once every five months, once every six months, once every seven months, once every eight months, once every nine months, once every 10 months, once every 11 months, even once every 12 months, or with a short administration interval at the beginning (such as once per week to once every three weeks), and then an extended interval later (such as once a month to even once every 12 months).

Actual dosage levels of the active ingredients in the pharmaceutical compositions of this invention may be varied so as to obtain an amount of the active ingredient that is effective to achieve the desired therapeutic response for a particular patient, composition, and mode of administration without being toxic to the patient. The selected dosage level will depend upon a variety of pharmacokinetic factors, including the activity of the particular composition of the invention employed, way of administration, the time of administration, the rate of excretion of the particular compound employed, the duration of the treatment, other drugs, compounds and/or materials used in combination with the particular composition employed, the age, sex, weight, condition, general health, and medical history of the patient being treated, and similar factors known in the medical field.

IV. Disease Treatment

The present inventors designed more than 200 siRNA molecules directed against CKIP-1 gene, from which siRNA molecules capable of significantly inhibiting CKIP-1 expression were screened (Examples 1-3). Experiments show that the CKIP-1 targeting molecule of the present invention can significantly inhibit the expression of CKIP-1 protein in human osteoblasts (Example 5), and administration of the dsRNA can promote the expression of phenotypic genes of human osteoblasts, thereby promoting osteoblast differentiation (Examples 6 and 7). In mouse and cynomolgus monkey models, administration of dsRNA of the invention significantly alleviates arthritis progression (Examples 8 and 9).

Even more surprisingly, the present inventors have found that the dsRNA of the present invention is capable of inhibiting the expression of pro-inflammatory cytokines IL-6, TNF-α and/or IL-17A (Examples 4 and 8). In particular, the dsRNA of the present invention can significantly inhibit the expression of the pro-inflammatory cytokine IL-6. TNF-α is mainly expressed by macrophages of inflamed joints, synovial lining cells and activated T cells. In RA inflamed joints, TNF-α is one of the most prominent pro-inflammatory cytokines capable of inducing the production of other pro-inflammatory factors such as IL-1 β, IL-6 and IL-8. IL-6 receptor neutralizing antibodies completely abolish the inflammatory response during the induction of CIA, suggesting that IL-6 plays an important role in the initiation of arthritis.

While previous pharmaceutical studies on CKIP-1 have been focused primarily on inhibiting bone destruction or repairing bone damage, the present invention for the first time discovered that dsRNA targeting CKIP-1 of the present invention can inhibit the expression of pro-inflammatory cytokines, and thus can be used to treat inflammation. The dsRNA targeting CKIP-1 of the present invention capable of inhibiting inflammation is particularly advantageous in the treatment of arthritis, particularly rheumatoid arthritis, because in RA, the main early symptoms are joint inflammation, while bone destruction only occurs after several years (referred to as "late stage bone destruction"). The dsRNA targeting CKIP-1 of the present invention can inhibit inflammation and also repair bone damage, and thus can be advantageously used in various stages of RA treatment, without being limited to late stage bone destruction.

Accordingly, in another aspect, the present invention provides a method of treating arthritis, particularly rheumatoid arthritis, in a subject in need thereof, comprising administering to the subject a therapeutically effective amount of a dsRNA molecule of the present invention or an expression vector of the present invention or a pharmaceutical composition of the present invention.

In yet another aspect, the invention also provides the use of a dsRNA of the invention or an expression vector of the invention or a pharmaceutical composition of the invention in the preparation of a medicament for treating arthritis, particularly rheumatoid arthritis, in a subject in need thereof.

Arthritis that can be treated by the dsRNA molecules of the invention or expression vectors of the invention or pharmaceutical compositions of the invention include, but are not limited to, rheumatoid arthritis, osteoarthritis, idiopathic arthritis, ankylosing spondylitis, psoriatic arthritis, infectious arthritis, Juvenile arthritis, reactive arthritis, gouty arthritis, and the like.

The dsRNA of the invention or the expression vector of the invention or the pharmaceutical composition of the invention may also be used in combination with an additional therapeutic agent for the treatment of arthritis, in particular rheumatoid arthritis. Such additional therapeutic agents include, but are not limited to, non-steroidal anti-inflammatory drugs, hormones, anti-rheumatic drugs, and the like.

In yet another aspect, the invention provides a method of treating an inflammatory disease associated with a pro-inflammatory cytokine (e.g., IL-6, TNF-α and/or IL-17A) in a subject in need thereof, comprising administering to the subject a therapeutically effective amount of a dsRNA molecule of the invention or an expression vector of the invention or a pharmaceutical composition of the invention.

In yet another aspect, the invention also provides the use of a dsRNA of the invention or an expression vector of the invention or a pharmaceutical composition of the invention in the preparation of a medicament for the treatment of an inflammatory disease associated with a pro-inflammatory cytokine (e.g., IL-6, TNF-α and/or IL-17A) in a subject in need thereof.

Inflammatory diseases associated with such pro-inflammatory cytokines (e.g., IL-6, TNF-α, and/or IL-17A) include, but are not limited to, inflammatory bowel disease, inflammation caused by infection, inflammation caused by injury, inflammation of the respiratory system, inflammation associated with cancer, and the like. Inflammatory diseases associated with such pro-inflammatory cytokines (e.g., IL-6, TNF-α and/or IL-17A) also include arthritis, such as those listed above, particularly rheumatoid arthritis.

Other inflammatory diseases associated with pro-inflammatory cytokines (e.g., IL-6, TNF-α, and/or IL-17A) that can be treated by dsRNA molecules of the invention or expression vectors of the invention or pharmaceutical compositions of the invention include, but are not limited to, systemic lupus erythematosus, Crohn's disease, psoriasis, colitis, ileitis, glomerulonephritis, asthma, dermatitis (including contact dermatitis and atopic dermatitis), vasculitis, chronic bronchitis, chronic prostatitis, appendicitis, pancreatitis, pelvic inflammation, polymyositis, chronic obstructive pulmonary disease and the like.

The dsRNA of the invention or the expression vector of the invention or the pharmaceutical composition of the invention may also be used in combination with additional therapeutic agents for the treatment of inflammatory diseases, in particular inflammatory diseases associated with pro-inflammatory cytokines such as IL-6, TNF-α and/or IL-17A. Such additional therapeutic agents are, for example, inhibitors that target TNF-α, including but not limited to Infliximab, Etanercept, Adalimumab, Golimumab, and Certolizumab; IL-6 blockers, including but not limited to, Tocilizumab; IL-17A blockers, including but not limited to Secukinumab.

In yet another aspect, the invention provides a method of treating a bone metabolism-related disorder in a subject in need thereof, comprising administering to the subject a therapeutically effective amount of a dsRNA molecule of the invention or an expression vector of the invention or a pharmaceutical composition of the invention.

In yet another aspect, the invention also provides the use of a dsRNA of the invention or an expression vector of the invention or a pharmaceutical composition of the invention in the preparation of a medicament for a bone metabolism-related disorder in a subject in need thereof.

Such bone metabolism related diseases include, but are not limited to, osteomalacia, bone deficiency, osteolytic bone disease, renal bone disease, osteogenesis imperfecta. bone destruction caused by cancer bone metastases, and the like.

The dsRNA of the present invention or the expression vector of the present invention or the pharmaceutical composition of the present invention may also be used in combination with additional therapeutic agents for the treatment of bone metabolism-related disorder.

In yet another aspect, the invention provides a method of reducing the level of a pro-inflammatory cytokine (e.g., IL-6, TNF-α and/or IL-17A) in a subject in need thereof, comprising administering to the subject a therapeutically effective amount of a dsRNA molecule of the invention or an expression vector of the invention or a pharmaceutical composition of the invention.

Preferably, in the above aspects of the invention, the subject is human.

In some embodiments, the dsRNA of the invention or the expression vector of the invention or the pharmaceutical composition of the invention is administered intra-articularly. In some embodiments, the dsRNA of the invention or the expression vector of the invention or the pharmaceutical composition of the invention is administered systemically.

EXAMPLES

A further understanding of the present invention may be obtained by reference to specific examples set forth herein which are presented for purposes of illustration only and are not intended to limit the scope of the invention in any way. It will be evident that various modifications and changes may be made thereto without departing from the spirit of the invention, and accordingly, such modifications and changes are intended to be within the scope of the appended claims.

Example 1. Sequence Design and Synthesis of siRNA Targeting CKIP-1

Candidate siRNAs were designed according to homologous regions of human CKIP-1 mRNA and monkey CKIP-1 mRNA sequences to obtain a candidate siRNA sequence pool. Off-target effects were comprehensively analyzed for the candidate siRNA sequence pool, and candidate siRNA sequences with high off-target scores were removed. By combining a seed region matching score, 208 siRNA candidate sequences against CKIP-1 were finally obtained and synthesized. Eight unrelated NC sequences were also designed and synthesized as negative controls in the screening assay. The synthesized 208 gene siRNA sequences, as well as 8 NC sequences, are as shown in FIG. 1.

Example 2. Real-time Quantitative PCR Screening for SiRNAs that Inhibit CIKP-1 Expression HFOB cells (human osteoblast strain commercially available from the Chinese Academy of Sciences) were seeded in 96-well cell culture plates, and siRNA transfection was performed at a cell density of about 70%. 0.5 μl of Lipofectamine2000 was diluted in 25 μl of opti-MEM without serum and antibiotics and mixed well. 15 μmol of RNA was diluted in 25 μl of opti-MEM without serum and antibiotics and mixed slightly. The Lipofectamine2000 dilution was added to the RNA dilution and mixed well. It was left at room temperature for 20 min. A mixture of 50 μl Lipofectamine2000 and RNA was added to a 96-well cell plate seeded with cells, slightly shaken to mix well, and the solution was changed after 5 h. RNA was extracted 48 hours later (TIANGEN micro RNA extraction kit), and qPCR detection (TransGen qPCR kit) was performed after reverse transcription (Takam reverse transcription kit). The relative expression of CIKP-1 was determined using GADPH gene as internal reference. The corresponding CIKP-1 relative expression values of the obtained siRNAs were normalized to the blank treatment group. Each NC sequence was also used as a negative control. The primer sequence is as follows:

```
CIKP1-F:  gGAACCAACCTCTTGTGCTG

CIKP1-R:  gTCAACTTCTTGGGTGCCTG

GADPH-F:  cATGAGAAGTATGACAACAGCCT

GADPH-R:  aGTCCTTCCACGATACCAAAGT
```

The results showed that 82 sequences with an interference efficiency of 50% and above were selected from 208 siRNA sequences (see Table 2), and 22 sequences have an interference efficiency of 70% and above (shown in bold italics in Table 2). These sequences were used as candidates for further screening.

TABLE 2 siRNA with interference efficiency of 50% and above

| SiRNA Sequence | Normalized target gene relative expression value |
|---|---|
| si-TD037 | 0.472339 |
| si-TD040 | 0.457801 |
| si-TD042 | 0.422001 |
| si-TD044 | 0.398672 |
| si-TD050 | 0.307432 |
| si-TD057 | 0.417976 |
| si-TD058 | 0.412397 |
| *si-TD060* | *0.250549* |
| si-TD061 | 0.314191 |
| *si-TD062* | *0.198302* |
| si-TD064 | 0.46957 |

TABLE 2-continued siRNA with interference efficiency of 50% and above

| SiRNA Sequence | Normalized target gene relative expression value |
|---|---|
| si-TD065 | 0.4389 |
| *si-TD066* | *0.30317* |
| si-TD067 | 0.411764 |
| *si-TD068* | *0.252114* |
| *si-TD070* | *0.281898* |
| si-TD072 | 0.401834 |
| *si-TD074* | *0.220171* |
| si-TD076 | 0.334746 |
| si-TD078 | 0.318811 |
| *si-TD080* | *0.23612* |
| *si-TD082* | *0.297076* |
| si-TD084 | 0.356374 |
| si-TD087 | 0.32098 |
| *si-TD089* | *0.238577* |
| si-TD093 | 0.367916 |
| si-TD094 | 0.410962 |
| *si-TD096* | *0.17883* |
| si-TD097 | 0.409968 |
| si-TD098 | 0.431926 |
| si-TD136 | 0.356366 |
| *si-TD137* | *0.118522* |
| si-TD138 | 0.387089 |
| si-TD139 | 0.335127 |
| *si-TD140* | *0.235433* |
| *si-TD141* | *0.287318* |
| *si-TD143* | *0.169164* |
| si-TD145 | 0.346415 |
| *si-TD176* | *0.223003* |
| si-TD177 | 0.410735 |
| *si-TD178* | *0.172067* |
| si-TD179 | 0.469953 |
| *si-TD181* | *0.224999* |
| si-TD217 | 0.414913 |
| si-TD221 | 0.462056 |
| si-TD224 | 0.490381 |
| si-TD358 | 0.387057 |
| *si-TD362* | *0.288363* |
| *si-TD364* | *0.275357* |
| si-TD370 | 0.445778 |
| si-TD372 | 0.459658 |
| si-TD376 | 0.387624 |
| *si-TD378* | *0.295441* |
| si-TD380 | 0.400417 |
| si-TD443 | 0.396858 |
| si-TD451 | 0.311861 |
| si-TD480 | 0.460598 |
| si-TD483 | 0.377209 |
| si-TD508 | 0.476182 |
| si-TD509 | 0.468754 |
| si-TD577 | 0.424962 |
| si-TD585 | 0.448536 |
| si-TD587 | 0.410307 |
| si-TD588 | 0.441516 |
| si-TD596 | 0.497351 |
| si-TD598 | 0.422082 |
| si-TD600 | 0.487359 |
| si-TD604 | 0.401307 |
| si-TD607 | 0.375209 |
| si-TD609 | 0.476541 |
| si-TD611 | 0.457187 |
| si-TD717 | 0.467227 |
| si-TD718 | 0.450869 |
| si-TD720 | 0.335688 |
| si-TD723 | 0.411798 |
| *si-TD726* | *0.270674* |
| *si-TD730* | *0.252773* |
| si-TD734 | 0.48745 |
| si-TD736 | 0.416718 |
| si-TD743 | 0.471836 |
| si-1 | 0.506191 |
| si-7 | 0.373945 |

Example 3. Identification of Candidate siRNA by Dual Luciferase Assay

In this example, candidate siRNA sequences obtained in Example 2 were further identified by a dual luciferase assay.

1. Constructing Target Gene CKIP-1 Overexpression Vector

The sequence fragment of CKIP-1 CDS 1-652 was amplified by PCR using upstream and downstream primers with SacI and XhoI restriction enzyme cutting sites and protective bases, respectively. The amplification product was digested by SacI and XhoI and then inserted into a pGP-miRGLO overexpression vector (see FIG. 2) which was also digested by SacI and XhoI to obtain the pmirGlo-CDS1 carrier overexpressing the sequence of the first segment (1-652) of the CDS region of CKIP-1 gene.

The sequence fragment of CKIP-1 CDS 653-1230 was amplified by PCR using upstream and downstream primers with SacI and XhoI restriction enzyme cutting sites and protective bases, respectively. The amplification product was digested by SacI and XhoI and then inserted into a pGP-miRGLO overexpression vector (see FIG. 2) which was also digested by SacI and XhoI to obtain the pmirGlo-CDS2 carrier overexpressing the sequence of the second segment (653-1230) of the CDS region of CKIP-1 gene.

2. Cell Culture 293T cells were regularly cultured in DMEM medium (Gibco) containing 10% FBS (Gibco) (containing 1.5 mM L-glutamine, 100 U/ml penicillin, 100 µg/ml streptomycin) in an incubator with 5% CO2 saturated humidity under 37° C.

3. Transfection of Cells

When 293T cells were cultured until 80-90% confluence in a 10 cm dish, the medium was decanted, and the cells were washed twice with 3 ml PBS. 1 ml of Trypsin-EDTA solution was added, mixed well, carefully aspirated the pancreatin solution and placed at 37° C. for 2-3 minutes. 2 ml complete medium was added and the cells were pippeted to form a single cell suspension. The cells were counted and seeded in 24-well plates at approximately 1×10⁵ cells per well.

150 µl of Opti-MEMI (50 µl/well*3) was added to a 1.5 ml EP tube, followed by adding 30 ng of the corresponding plasmid (10 ng per well) and the corresponding amount of siRNA (each siRNA final concentration setting gradient: 6.25, 12.5, 25, 50, 100, 300 nM, the final concentration of the negative control NC-7 is 25 nM), and mixing well; another 1.5 ml EP tube was filled with 150 µl of Opti-MEMI (50 µl/well*3) and 6 µl of transfection reagent Lipo2000, mixed well, left standstill for 5 min and then mixed well in a volume of 300 ul for 20 min at room temperature. The culture medium was removed from the 24-well plate prepared on the previous day, and 400 µl/well culture medium was added; after being left standstill for 20 min, the transfection mixture was added to the above 24-well plate by 100 µl/well, with each 3 replicates, Blank wells and Mock wells were set, the plates were shaken well and incubated in an incubator for 6 hours. The transfection liquid was removed, rinsed with PBS, culture medium was added in for continuous culture, and photos of the wells transfected with NC-FAM were taken to observe the transfection efficiency. Cells were collected 24 h after transfection for dual luciferase assay.

4. Dual Luciferase Assay

Experimental materials and reagents: Dual-Luciferase Reporter Assay System (Promega, E1960); PBS; 96-well white plate (corning cat #3912); Multilabel Microplate Detector (PerkinElmer EnSpire).

Experimental steps: the medium was removed from the cell plates to be examined, the cultured cells were washed with PBS, and the PBS was aspirated and discarded. 1×PLB was added by 100 µl/well, and the plates were slightly shaken at room temperature and lysed for 15 min. The cell lysate was moved into a small centrifuge tube for centrifugation at 3000 rpm for 3 min, cell debris were removed, 30 µl of supernatant was taken, added to a 96-well white plate, and a substrate was added for detection according to the recommended operation steps of the specification.

Results:

Four siRNAs have good inhibition effects on CKIP-1 expression in a dual luciferase assay: si-TD137, si-TD141, si-TD176, and si-7. The results are shown in Tables 3-6 and FIGS. 3-6, respectively.

TABLE 3

Dual luciferase assay results for si-TD137

|  | Total mean value of normalized dual luciferase relative activity | Standard deviation | P-value compared with NC7 group |
|---|---|---|---|
| empty vector | 261.5710548 | 96.3502 |  |
| empty vector + NC-7 | 252.5532524 | 80.68784 |  |
| empty vector + 137-6.25 | 222.8452964 | 63.83427 |  |
| empty vector + 137-12.5 | 228.8008311 | 67.97434 |  |
| empty vector + 137-25 | 224.1443386 | 70.3993 |  |
| empty vector + 137-50 | 233.7895134 | 96.01054 |  |
| empty vector + 137-100 | 240.7744442 | 70.31852 |  |
| empty vector + 137-300 | 224.4435964 | 65.32518 |  |
| CDS1 | 100 | 0 |  |
| CDS1 + NC-7 | 97.47065705 | 27.59265 |  |
| CDS1 + 137-6.25 | 12.30603204 | 2.139099 | 0.005965 |
| CDS1 + 137-12.5 | 10.86442887 | 2.108049 | 0.005615 |
| CDS1 + 137-25 | 10.28528737 | 1.054173 | 0.005438 |
| CDS1 + 137-50 | 9.281597349 | 2.315117 | 0.005271 |
| CDS1 + 137-100 | 10.82386854 | 1.645889 | 0.005582 |
| CDS1 + 137-300 | 7.593906894 | 3.041176 | 0.004967 |

TABLE 4

Dual luciferase assay results for si-TD141

|  | Total mean value of normalized dual luciferase relative activity | Standard deviation | P-value compared with NC7 group |
|---|---|---|---|
| empty vector | 232.9723364 | 61.66293 |  |
| empty vector + NC-7 | 205.4147266 | 20.38412 |  |
| empty vector + 141-6.25 | 215.5570016 | 37.7184 |  |
| empty vector + 141-12.5 | 210.1388575 | 23.7144 |  |
| empty vector + 141-25 | 217.6250075 | 31.30451 |  |
| empty vector + 141-50 | 195.7261375 | 45.5828 |  |
| empty vector + 141-100 | 225.8556173 | 53.21314 |  |
| empty vector + 141-300 | 194.396959 | 47.47294 |  |
| CDS1 | 100 | 0 |  |
| CDS1 + NC-7 | 95.13464683 | 19.17207 |  |
| CDS1 + 141-6.25 | 16.98508418 | 2.229641 | 0.002177 |
| CDS1 + 141-12.5 | 14.2576769 | 3.90799 | 0.002015 |
| CDS1 + 141-25 | 12.61787894 | 3.959899 | 0.001872 |
| CDS1 + 141-50 | 12.64749866 | 2.563133 | 0.001791 |
| CDS1 + 141-100 | 12.05755431 | 0.886328 | 0.001693 |
| CDS1 + 141-300 | 8.134042105 | 2.163326 | 0.00145 |

TABLE 5

Dual luciferase assay results for si-TD176

| | Total mean value of normalized dual luciferase relative activity | Standard deviation | P-value compared with NC7 group |
|---|---|---|---|
| empty vector | 259.3844179 | 14.91878 | |
| empty vector + NC-7 | 253.6837275 | 24.80359 | |
| empty vector + 176-6.25 | 232.3986339 | 17.01937 | |
| empty vector + 176-12.5 | 199.7533446 | 2.950685 | |
| empty vector + 176-25 | 218.9236568 | 32.63606 | |
| empty vector + 176-50 | 203.8520998 | 31.30066 | |
| empty vector + 176-100 | 219.0134189 | 30.88615 | |
| empty vector + 176-300 | 186.6665828 | 16.72755 | |
| CDS1 | 100 | 0 | |
| CDS1 + NC-7 | 94.53375651 | 4.874274 | |
| CDS1 + 176-6.25 | 21.31523373 | 1.321383 | 1.49E-05 |
| CDS1 + 176-12.5 | 21.95335577 | 2.282599 | 1.99E-05 |
| CDS1 + 176-25 | 20.89875168 | 1.167482 | 1.42E-05 |
| CDS1 + 176-50 | 19.27982377 | 0.247705 | 1.17E-05 |
| CDS1 + 176-100 | 21.66118398 | 3.755765 | 3.34E-05 |
| CDS1 + 176-300 | 18.16630661 | 1.603929 | 1.35E-05 |

TABLE 6

Dual luciferase assay results for si-7

| | Total mean value of normalized dual luciferase relative activity | Standard deviation | P-value compared with NC7 group |
|---|---|---|---|
| empty vector | 161.0586219 | 66.14465 | |
| empty vector + NC-7 | 164.50757 | 62.34558 | |
| empty vector + si7-6.25 | 169.6545487 | 57.58843 | |
| empty vector + si7-12.5 | 170.6842599 | 53.23935 | |
| empty vector + si7-25 | 162.2483155 | 54.75665 | |
| empty vector + si7-50 | 171.4671143 | 51.29689 | |
| empty vector + si7-100 | 172.0681778 | 62.19204 | |
| empty vector + si7-300 | 163.0764404 | 51.25441 | |
| CDS2 | 100 | 0 | |
| CDS2 + NC-7 | 99.61211154 | 15.69399 | |
| CDS2 + si7-6.25 | 17.29806814 | 2.382198 | 0.00085 |
| CDS2 + si7-12.5 | 18.13340456 | 1.80696 | 0.000868 |
| CDS2 + si7-25 | 17.09295528 | 1.84478 | 0.000828 |
| CDS2 + si7-50 | 18.07601932 | 0.777867 | 0.000848 |
| CDS2 + si7-100 | 17.5441839 | 3.941363 | 0.000926 |
| CDS2 + si7-300 | 15.54928456 | 3.365782 | 0.000819 |

Example 4. siRNA Targeting CKIP-1 Inhibits Expression of Pro-Inflammatory Cytokine RAW264.7 mouse peritoneal macrophage cell line (purchased from Cell Bank of Chinese Academy of Sciences, Shanghai) was cultured in complete DMEM medium containing 10% fetal bovine serum, 100 U penicillin and streptomycin, and cultured overnight in an incubator under 37° C. constant temperature carbon dioxide (5%) until cell confluence reached 70-80%.

In vitro, mouse macrophages transfected with the small interfering RNAs against CKIP-1 prepared as described above or their modified forms having methoxy group modification on sense strand were used as a drug treatment group (RNAi group), and the cells treated with the transfection reagent X-TremeGENE siRNA transfection reagent alone (commercially available from Roche, article number 4476093001) were used as a transfection reagent group (MOCK group), 3 in each group in parallel, at least three times for each experiment. For transfection of mouse macrophages, the final concentration of small interfering RNA was 30 nM. 24 hours after transfection, LPS (commercially available from Sigma, Cat. No. L2630-10MG) was added to stimulate for 6 hours, supernatants of cells of each group were collected, secretion of proinflammatory cytokines was detected, and mRNA expression levels of proinflammatory cytokines were detected by collecting cells of each group.

1. Determination of TNF-α and IL-6 Protein Secretion Inhibition Efficiency by siRNA Inhibition efficiency of the secretion levels of TNF-α and IL-6 in the cell supernatant was determined by an ELISA method, specifically: Mouse TNF alpha ELISA Ready-SET-Go!® (eBioscience, Cat. No. 88-7324-88) and Mouse IL-6 ELISA Ready-SET-Go! (eBioscience, Cat. No. 88-7064-88) kits were used according to the instructions, and the concentrations of TNF-α and IL-6 were calculated by plotting standard curves.

Cytokine inhibition efficiency was calculated as follows:

Cytokine inhibition efficiency=[(*LPS* group-treated group)/(*LPS* group-blank control group)]×100%.

The results of the determination are shown in Tables 7 and 8 below:

TABLE 7

| | | Inhibition (%) of TNFα secretion | Inhibition of IL-6 secretion (%) |
|---|---|---|---|
| MOCK group | Transfection reagent | 3.71 | 29.81 |
| RNAi group | si-7 | 32.23 | 77.13* |
| | si-137 | 25.95 | 55.58* |
| | si-141 | 21.49 | 65.30* |
| | si-176 | 17.75 | 56.69* |

Note:
*P < 0.05, compared with MOCK group, there was statistically significant difference.

TABLE 8

| | | Inhibition (%) of TNF α secretion | Inhibition of IL-6 secretion (%) |
|---|---|---|---|
| MOCK group | Transfection reagent | 1.28 | 21.62 |
| RNAi group | si-7-Ome | 35.51 | 89.75* |
| | si-137-Ome | 26.30 | 84.51* |
| | si-141-Ome | 27.95 | 87.85* |
| | si-176-Ome | 21.10 | 80.12* |

Notes:
*P < 0.05, compared with MOCK group, there was statistically significant difference.

As can be seen from the above table, each candidate siRNA and its methylation modified form inhibited LPS-induced IL-6 and TNF-α secretion from RAW264.7 mouse macrophages, and the inhibition of IL-6 secretion reached a significant level.

2. Determination of TNF-α and IL-6 mRNA Expression Inhibition Efficiency by siRNA TNF-α and IL-6 mRNA levels in the collected RAW264.7 cells were detected by a real-time fluorescence quantitative PCR (real-time PCR) method, specifically: total cellular RNA was extracted using TRIzol reagent (Invitrogen, article number 15596018), cDNA was synthesized by reverse transcription using TransScriptAll-in-One First-Strand cDNA Synthesis SuperMixforq PCR (One-Step DNA Removal) (TransGen, article number AT341-02) kit, and the inhibitory efficiency of siRNA on LPS-induced IL-6 and TNF-α expression in murine peritoneal macrophages was detected by fluorescence quantitative PCR.

The GAPDH gene was used as an internal reference gene in the Real-time PCR method, and the primer sequences were shown in Table 9

TABLE 9

|  | Forward (5'-3') | Reverse (5'-3') |
|---|---|---|
| Mice TNF-α | TCAGCGAGGACAGCAAGG | AGTGAGTGAAAGGGACAGAACC |
| Mice IL-6 | CCTTCTTGGGACTGATGCTG | TTGGGAGTGGTATCCTCTGTGA |
| Mice GAPDH | CCTTCATTGACCTCAACTACATGG | CTCGCTCCTGGAAGATGGTG |

In the fluorescence quantitative PCR method, the nucleic acid inhibition efficiency is calculated according to the following equation:

siRNA inhibition efficiency=[(LPS group cytokine gene copy number/LPS group GAPDH gene copy number-treatment group cytokine gene copy number/treatment group GAPDH gene copy number)/(LPS group cytokine gene copy number/LPS group GAPDH gene copy number-blank control group cytokine gene copy number/blank control group GAPDH gene copy number)]×100%

The results are shown in Table 10:

TABLE 10

|  |  | Inhibition (%) of TNFα secretion | Inhibition of IL-6 secretion (%) |
|---|---|---|---|
| MOCK group | Transfection reagent | 11.13 | 11.96 |
| RNAi group | si-7 | −4.6 | 70.75* |
|  | si-137 | 6.64 | 40.78* |
|  | si-141 | −1.58 | 54.53* |
|  | si-176 | 6.80 | 45.76* |

Notes:
*P < 0.05, compared with MOCK group, there was statistically significant difference.

As can be seen from Table 10, each candidate siRNA significantly inhibited LPS-induced IL-6 mRNA expression in mouse macrophages; there was no significant inhibitory effect on TNF-α mRNA expression.

It can be seen that the CKIP-1 targeting siRNAs of the present invention can inhibit the levels of the pro-inflammatory cytokines IL-6 and TNF-α, particularly IL-6, thereby inhibiting inflammation, particularly inflammation associated with IL-6 and/or TNF-α, such as inflammation in RA.

Example 5. Inhibitory Effect of siRNA Targeting CKIP-1 on CKIP-1 Protein Expression Human osteoblast cell line hFOB1.19 purchased from the Chinese Academy of Sciences cell bank was cultured in DMEM-F12 medium containing 10% fetal bovine serum (purchased from Gibco). Human osteoblast hFOB1.19 was transferred to 24-well plates for overnight culture for adhesion. Human osteoblast hFOB1.19 transfected with siRNA targeting CKIP-1 was used as treatment group, and the cells transfected with non-specific nucleic acid were used as negative control group (NC group). Each group with 2 duplicates was repeated at least 3 times. Human osteoblast cells were transfected with a final nucleic acid concentration of 20 μM. After 72 hours of transfection, cells were collected and assayed for CKIP-1 protein expression.

The content of CKIP-1 protein in osteoblast cells was detected by immunoblotting according to the method in the literature (Molecular Cloning A Laboratory Manual, Science Press, 2005). The CKIP-1 antibody used for immunoblotting was purchased from Santa Cruz Biotechnology (Cat. No. sc-376355) and the internal reference antibody was GADPH (purchased from Santa Cruz Biotechnology, Cat. No. sc-166574).

In immunoblotting, nucleic acid inhibitory activity was calculated as follows: nucleic acid inhibitory activity=[1−(light intensity value of CKIP-1 Western blot band of treatment group/light intensity value of GAPDH Western blot band of treatment group)/(light intensity value of CKIP-1 Western blot band of control group/light intensity value of GAPDH Western blot band of control group)]×100%.

Result: the expression of CKIP-1 in hFOB1.19 cells was significantly inhibited by si-7. Compared with control NC, there was significant difference (P<0.05). The determined results are shown in Table 11.

TABLE 11

|  | Inhibition rate (%) of CKIP-1 protein expression |
|---|---|
| NC | 0.0 |
| si-7 | 74.5* |

Example 6. Effect of siRNA Targeting CKIP-1 on Osteoblast Differentiation

Similar to Example 5, CKIP-1 siRNA was tested for mRNA expression levels of human osteoblast hFOB1.19 phenotypic gene alkaline phosphatase (ALP), type I collagen (COL1), osteopontin (OPN), bone sialoprotein (BSP) and osteocalcin (OC) over time using primers as shown in Table 12. The determined results are shown in Table 13.

TABLE 12

| Gene | Primer sequence (5'-3') Forward | Reverse | Product Size | Tm | Genbank No. |
|---|---|---|---|---|---|
| HumanALP | GTCAGCTCCACC ACAACCCT | GCCCTCATTGGC CTTCACCC | 155 | 60 | NM_000478.3 |

TABLE 12-continued

| Gene | Primer sequence (5'-3') Forward | Reverse | Product Size | Tm | Genbank No. |
|---|---|---|---|---|---|
| HumanCOL1 | CACTGGTGATGC TGGTCCTG | CGAGGTCACGG TCACGAAC | 179 | 60 | NM_000088.3 |
| HumanOPN | GTACCCTGATGC TACAGACG | TTCATAACTGTC CTTCCCAC | 139 | 60 | NM_001040060.1 |
| HumanBSP | GGCACCTCGAA GACAACAAC | GCCCGTGTATTC GTACTCCC | 135 | 60 | NM_004967.3 |
| HumanOC | AGGGCAGCGAG GTAGTGAAG | TGTGGTCAGCC AACTCGTCA | 138 | 60 | NM_199173.3 |
| HumanGAPDH | GGCATGGACTGT GGTCATGAG | TGCACCACCAA CTGCTTAGC | 87 | 60 | NM_002046.3 |

TABLE 13

| | Increasing rate of ALP mRNA (%) | Increasing rate of COL1 mRNA (%) | Increasing rate of OPN mRNA (%) | Increasing rate of BSP mRNA (%) | Increasing rate of OC mRNA (%) |
|---|---|---|---|---|---|
| NC | 0 | 0 | 0 | 0 | 0 |
| si-7 | 86.5* | 70.2* | 93.0* | 171.6* | 85.11* |

*P < 0.05: compared with NC group, there was statistical difference.

Result: ALP, COL1A1 and OPN begin to express at the early stage of osteoblast differentiation, while BSP and OC begin to express at the mature stage of osteoblast. After 72 hours of action, the expression of ALP, COL1, OPN, BSP and OC in si-7 group were significantly higher than that in NC group.

The experimental results show that the siRNA targeting CKIP-1 can increase the expression of the phenotypic genes of the human osteoblast cell line hFOB1.19, thereby promoting osteoblast differentiation.

Example 7. Effect of siRNA Targeting CKIP-1 on Bone Matrix Mineralization Deposition Rate Calcium deposition is a key functional mineralization marker for mature osteoblasts during osteoblast formation in vitro. As described above, the human osteoblast cell line hFOB1.19 transfected with siRNA targeting CKIP-1 was used as a treatment group, and the cells transfected with non-specific nucleic acid were used as a negative control group (NC group). The final nucleic acid concentration for transfection was 20 μM. The frequency of interval transfection was once a week, with 4 duplicates per group in parallel. Calcium deposition in human osteoblast cell line hFOB1.19 was determined by calcium staining 7, 14 and 21 days after the first transfection.

The results are shown in Table 14. 21 days after the first transfection of the human osteoblast cells, the calcium deposition of the treatment group is obviously higher than that of the NC group, which at the functional level verifies that the siRNA can promote the differentiation of human preosteoblasts into mature osteoblasts.

TABLE 14

| | | Calcium deposition in human osteoblasts (ng/μg protein) |
|---|---|---|
| NC Group | Non-specific nucleic acid | 0.00 |
| Treatment group | si-7 | 64.81* |

*P < 0.05: compared with NC group, there was statistical difference.

Example 8. Assessment of siRNA Activity In Vivo Using a Mice CIA Model

Collagen-induced arthritis (CIA) model was established in 8-10 week old male DBA mice by subcutaneous injection of type II collagen at the root of the tail. The specific method is as follows: a proper amount of bovine type II collagen with a concentration of 2 mg/mL was mixed with an equivalent amount of incomplete Freund's adjuvant, fully emulsified, and the emulsified mixture was injected subcutaneously at the root of the tail with 100 μg of type II collagen/mouse. After 21 days, 50 μg of type II collagen was injected subcutaneously once at the root of the tail for boost.

5-grade semi-quantitative evaluation standard was taken as the evaluation standard of arthritis clinical severity: 0: no red swelling; 1: erythema accompanied with moderate swelling and confined to the midfoot or ankle; 2: moderate swelling extended from the ankle to the midfoot; 3: moderate swelling extended from the ankle joint to the metatarsal joint; 4: severe swelling of ankle, foot and toes.

The animals were randomly grouped if the severity of the double hindlimbs of each group of animals was scored about 1 through visual evaluation: carrier group, ankle joint cavity was injected with blank liposome; NC (negative control) group, liposomes loaded with negative control sequences were injected into the ankle joint cavity; the treatment group, liposomes loaded with Si-7, Si-137, Si-141 or Si-176 were injected into ankle joint cavity; the positive control group was administered with the positive drug Etanercept (purchased from Shanghai CP Guojian Pharmaceutical Co., Ltd., each containing 12.5 mg of active ingredient).

The animals in each group were administered by injecting into the bilateral ankle joint cavities of the hind limbs at a dose of 4 μg siRNA/5 μl liposome/ankle joint, six times on day 0, day 7, day 14, day 21, day 28 and day 35. The positive drug was administered by subcutaneous injection at a dose of 7.5 mg/kg body weight.

1. Effect of siRNA Treatment on Clinical Score and Body Weight of CIA Mice

Figure 7:
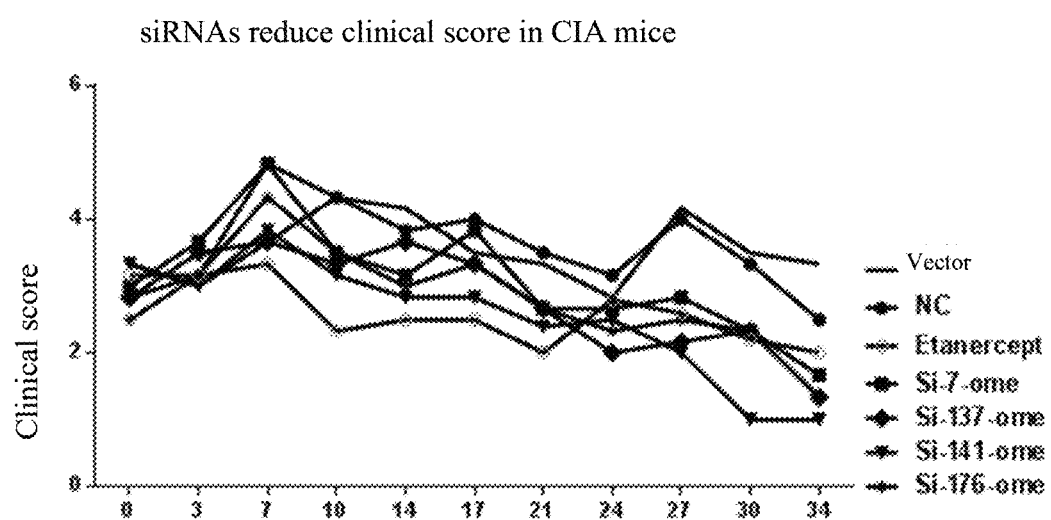
FIG. 7 shows that siRNAs decrease CIA mouse clinical score.
Figure 8:
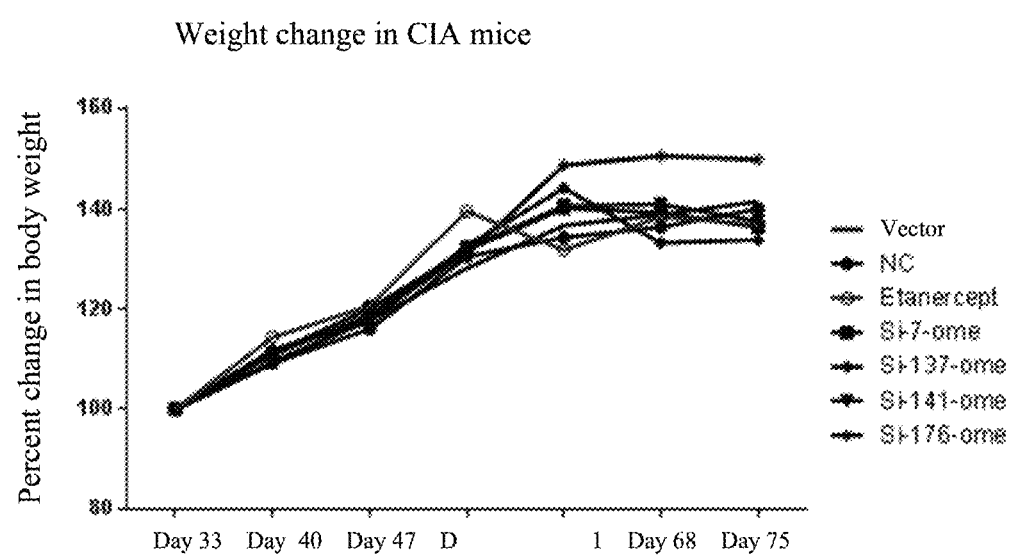
FIG. 8 shows body weight changes in CIA mice after siRNA treatment.

The scores for swelling in the ankle joint of both hind limbs of mice were observed and recorded from the day of start twice a week, and the scores for the ankle joint of both hind limbs were added for statistical analysis. Clinical scoring results are shown in FIG. 7 and Table 15 below. Meanwhile, the body weight of the mice was recorded once a week, and the results are shown in FIG. 8 and Table 16.

The results showed that the body weight of each group of mice increased without weight loss. Si-7-Ome, Si-137-Ome, Si-141-Ome, and Si-176-Ome all significantly reduced the clinical score of mice CIA model arthritis, the inhibition rates were 50%, 60%, 70% and 60%, respectively, and the effects were better than the positive drug Etanercept (inhibition 40%).

TABLE 15

Inhibition of mice CIA clinical scores

| Grouping | | Mice CIA clinical score | Inhibition rate of mice CIA clinical score (%) |
|---|---|---|---|
| Carrier groups | Carrier | 3.33 | |
| NC group | Nonspecific nucleic acid | 2.50 | 24.99 |
| PC group | Etanercept | 2.00 | 39.99 |
| Treatment group | Si-7-Ome | 1.67* | 49.98 |
| | Si-137-Ome | 1.33** | 60.01 |
| | Si-141-Ome | 1.00*** | 70.00 |
| | Si-176-Ome | 1.33** | 60.01 |

Notes:
*indicates P < 0.05 as compared with the carrier groups,
**indicates P <0.01 as compared with the carrier groups,
**indicates P < 0.001 as compared with the carrier groups.

TABLE 16

Effect on body weight change in mice

| | | Day 0 | Day 42 | Weight change rate (%) of CIA mice |
|---|---|---|---|---|
| Carrier groups | Carrier | 16.8 | 23.7 | 141.1 |
| NC group | Nonspecific nucleic acid | 17.4 | 24.3 | 139.7 |
| PC group | Etanercept | 16.6 | 23.0 | 138.6 |
| Treatment group | Si-7-OMe | 16.4 | 22.4 | 136.6 |
| | Si-137-OMe | 16.0 | 21.6 | 135.0 |

TABLE 16-continued

Effect on body weight change in mice

| | Day 0 | Day 42 | Weight change rate (%) of CIA mice |
|---|---|---|---|
| Si-141-OMe | 15.6 | 21.7 | 139.1 |
| Si-176-OMe | 15.9 | 24.0 | 150.9 |

2. Effect of siRNA on Expression of Proinflammatory Factors in Joint Tissue of CIA Mice After sacrifice, the fur of CIA model mice was cut off from the legs with scissors, so that the ankle joint was exposed, the portion below knee joint was cut off with forceps, cooled with liquid nitrogen, grinded and transferred to an enzyme-free tube, and total cellular RNA was extracted using TRIzol reagent (Invitrogen, article number 15596018). cDNA was synthesized by reverse transcription using TransScript All-in-One First-Strand cDNA Synthesis SuperMix for qPCR (One-Step gDNA Removal) (TransGen, article number AT341-02) kit. The inhibitory effects of si-7, si-137, si-141 and si-176 on CKIP-1, IL-6, TNF-α and IL-17A mRNA expression in joint tissue of CIA mouse model were detected by fluorescence quantitative PCR.

Primers for IL-6, TNF-α, and the reference gene GAPDH as described above were used. The CKIP-1, IL-17A primer sequences are shown in Table 17:

TABLE 17

| | Forward (5'-3') | Reverse (5'-3') |
|---|---|---|
| Mice IL-17A | CTCCACCGCAATGAAGACC | CCCTCTTCAGGACCAGGATC |
| Mice CKIP-1 | TTTCTCGGCCTTGGGAAAAAC | GAGGCACATCGGCTCTTCT |

In the fluorescent quantitative PCR method, the expression inhibition efficiency is calculated as follows:

Inhibition efficiency=[(cytokine gene copy number of the carrier groups/GAPDH gene copy number-treatment group cytokine gene copy number of the carrier groups/GAPDH gene copy number of the treatment groups)/(cytokine gene copy number of the carrier groups/GAPDH gene copy number-cytokine gene copy number of the normal control groups/GAPDH gene copy number of the normal control groups)]× 100%

Figure 9:
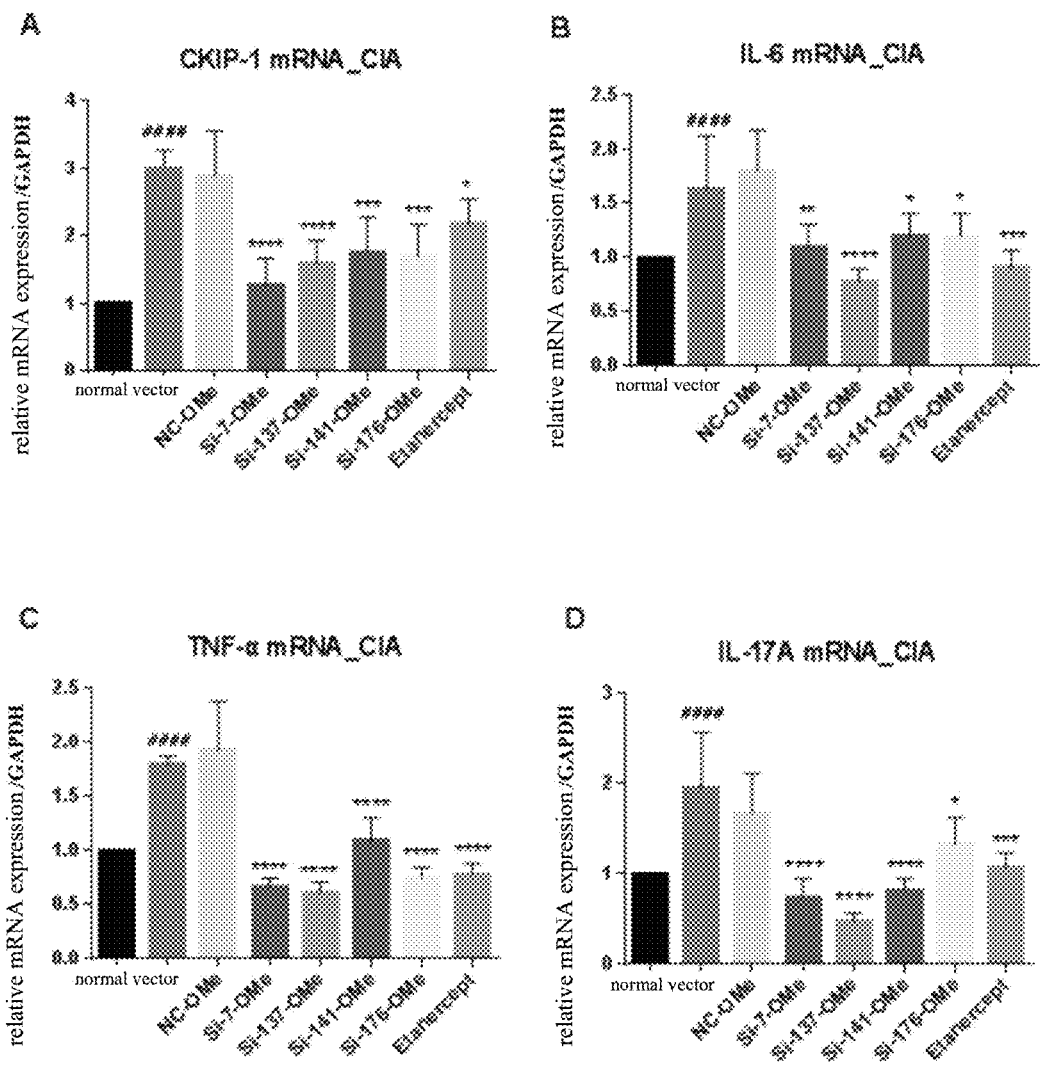
FIG. 9 shows that siRNAs affect proinflammatory cytokine expression in joint tissue of CIA mice.

The results of the determination are shown in Table 18 and FIG. 9:

TABLE 18

| | | Inhibition rate of CKIP-1 mRNA (%) | Inhibition rate of IL-6 mRNA (%) | Inhibition rate of TNF-α mRNA (%) | Inhibition rate of IL-17A mRNA (%) |
|---|---|---|---|---|---|
| Carrier groups | Empty liposome | 0 | 0 | 0 | 0 |
| NC group | Non-specific nucleic acid | 7.10 | −28.46 | −16.43 | 29.42 |
| Positive control group | Etanercept | 41.37* | 113.83*** | 127.36**** | 92.10*** |
| Treatment group | Si-7-OMe | 86.60**** | 83.17** | 142.72**** | 126.59**** |
| | Si-137-OMe | 70.83**** | 135.84**** | 147.90**** | 154.57**** |

TABLE 18-continued

|  | Inhibition rate of CKIP-1 mRNA (%) | Inhibition rate of IL-6 mRNA (%) | Inhibition rate of TNF-α mRNA (%) | Inhibition rate of IL-17A mRNA (%) |
|---|---|---|---|---|
| Si-141-OMe | 62.04*** | 68.85* | 88.25**** | 118.81**** |
| Si-176-OMe | 65.02*** | 68.85* | 131.98**** | 65.53* |

Notes:
*P < 0.05, compared with carrier group, there was statistically significant difference;
**P < 0.01, compared with carrier group, there was statistically significant difference;
***P < 0.001, compared with carrier group, there was statistically significant difference;
****P < 0.0001, compared with carrier group, there was statistically significant difference;
### P < 0.0001 compared with the normal control group, there was statistically significant difference.

It can be seen that si-7-OMe, si-137-OMe, si-141-OMe, si-176-OMe all significantly inhibited the expression of CKIP-1, IL-6, TNF-α, IL-17AmRNA in the joint tissues of CIA mice, with inhibition rates more than 50%, and the inhibition of CKIP-1 mRNA was stronger than that of the positive drug Etanercept (41.37%). Compared with other small interfering RNAs, si-137 showed a stronger inhibitory effect on pro-inflammatory factors IL-6, TNF-α, IL-17AmRNA, and the inhibitory effect was stronger than that of the positive drug Etanercept. The siRNAs of the present invention are shown to be effective in inhibiting inflammation in RA.

3. Micro CT Detection

Scancoviva CT 40 was used for the micro-CT detection. A mouse hind paw was put into a Micro CT sample tube for three-dimensional CT scanning and reconstruction. After the scanning, a matched software was used for analyzing the three-dimensional microstructure of the trabeculae and collecting the spatial structure parameters of the trabeculae.

4. Pathological Examination

The hind limbs of mice were fixed in 4% formaldehyde solution and embedded with paraffin after EDTA decalcification. The pathological changes of joints and bone erosion were examined through serial section and HE staining.

5. Bone Morphometric Analysis

Mice were intraperitoneally injected with xylenol orange (90 mg/kg) 12 days before sacrifice and intraperitoneally injected with calcein (10 mg/kg) 2 days before sacrifice. After sacrifice, hind paws were removed and 10 μm discrete sections were made using a non-decalcifying microtome. Sections were stained with 1% methylene blue followed by light microscopy and unstained sections were used for fluorescence microscopy. The metatarsal bones in the paws were used for bone morphometric analysis.

Compared with the control group, each siRNA administration group played an positive role in improving inflammation and bone injury of a rheumatoid arthritis model and delaying disease progress, exhibiting good therapeutic effect.

Example 9. Validation of Effect of the siRNAs with Monkey Rheumatoid Arthritis Model 1. Animal Modeling and Administration 3-6-year-old female cynomolgus monkeys were immunized with bovine type II collagen on day 0 and day 21, respectively, according to modeling methods of collagen-induced arthritis described in related literatures. The drug is locally administered into the joint after the onset of the disease. Liposome delivery systems were used for the small nucleic acids.

Grouping is as follows: as for the carrier groups, empty liposomes were injected into the joint cavity; as for NC (negative control) groups, liposomes loaded with negative control sequences were injected into ankle joint cavity; as for the treatment group, liposomes loaded with Si-7, Si-137, Si-141 or Si-176 were injected into the articular cavity; as for the positive control group, the positive drug etanercept (purchased from Shanghai CP Guojian Pharmaceutical Co., Ltd.) was administered. Three animals in each group were administered by articular injection once a week for 6 weeks.

2. Detection of Parameters

MicroCT, pathology, bone morphometry and other tests were similar to experiments in mice.

Compared with the control group, the siRNA administration group showed good treatment effects on improving disease condition, especially reducing bone damage, maintaining bone function and the like in a rheumatoid arthritis model.

What we claim is:

1. A pharmaceutical composition suitable for inhibiting casein kinase interacting protein 1 (CKIP-1) expression in a human subject in need thereof, which comprises:
   (i) an amount of a double-stranded RNA (dsRNA) molecule comprising a sense strand shown in SEQ ID NO: 63 and an antisense strand shown in SEQ ID NO: 64 effective to inhibit the expression of CKIP-1 in a human subject in need thereof; and
   (ii) a pharmaceutically acceptable carrier;
   wherein said composition when administered to a human subject in need thereof is capable of inhibiting CKIP-1 expression.

2. The pharmaceutical composition of claim 1, wherein the sense and/or antisense strand additionally has an overhang of at least one nucleotide at the 3' end.

3. The pharmaceutical composition of claim 2, wherein the sense and/or antisense strand additionally has an overhang of 2 nucleotides at the 3' end, preferably the overhang is TT.

4. The pharmaceutical composition molecule of claim 1, wherein the sense strand and the antisense strand comprise 1 or 2 nucleotide substitutions located within 6, 5, 4, 3 or 2 nucleotides from the 5' and/or 3' end.

5. The pharmaceutical composition of claim 4, wherein the sense and antisense strands comprise 1 nucleotide substitution, which is located at the last nucleotide of the 3' end of the sense strand and correspondingly at the first nucleotide of the 5' end of the antisense strand.

6. The pharmaceutical composition of claim 1, wherein the dsRNA molecule comprises at least one modified nucleotide.

7. The pharmaceutical composition of claim 6, wherein the modified nucleotide is selected from the group consisting of: 2'-O-methyl modified nucleotides, 2'-F modified nucleotides, nucleotides containing 5'-phosphorothioate groups and end nucleotides linked to cholesteryl derivatives or dodecanoic acid bisdecylamide groups, 2'-deoxy-2'-fluoro modified nucleotides, 2'-deoxy-modified nucleotides, locked nucleotides, abasic nucleotides, 2'-amino-modified nucleotides, 2'-alkyl-modified nucleotides, morpholino nucleotides, phosphoramidates and nucleotides containing non-natural bases.

8. The pharmaceutical composition of claim 6, wherein the 2' hydroxyl groups of all nucleotides with uracil or cytosine bases in the sense and/or antisense strands are modified with methoxy groups.

9. The pharmaceutical composition of claim 1, wherein the dsRNA molecule is an siRNA or shRNA.

10. The pharmaceutical composition of claim 1, wherein the dsRNA molecule inhibits CKIP-1 expression by at least 50%, preferably by at least 70%.

11. The pharmaceutical composition of claim 1, which inhibits the expression of TNF-α.

12. The pharmaceutical composition of claim 1, which inhibits the expression of IL-6.

13. The pharmaceutical composition of claim 1, which inhibits the expression of IL-17A.

14. The pharmaceutical composition of claim 1, which is suitable for treating a subject with arthritis.

15. The pharmaceutical composition of claim 14, which is formulated for topical injection into a joint of the subject.

16. The pharmaceutical composition of claim 15, which when topically administered reduces TNF-α, IL-6, and/or IL-17A in the joint.

17. The pharmaceutical composition of claim 15, which when topically administered reduces swelling of the joint.

18. The pharmaceutical composition of claim 1, wherein the only nucleic acid contained therein which inhibits CKIP-1 expression consists of a double-stranded RNA (dsRNA) molecule which is comprised of the sense strand shown in SEQ ID NO: 63 and the antisense strand shown in SEQ ID NO: 64.

19. The pharmaceutical composition of claim 1, wherein the dsRNA molecules are comprised in liposomes.

20. The pharmaceutical composition of claim 1, which also contains at least one pharmaceutically acceptable antioxidant selected from (1) ascorbic acid, cysteine hydrochloride, sodium bisulfate, sodium metabisulfite, or sodium sulfite; (2) an oil-soluble antioxidant selected from ascorbyl palmitate, butylated hydroxyanisole (BHA), butylated hydroxytoluene (BHT), lecithin, propyl gallate, and alpha-tocopherol; and (3) a metal chelating agent selected from citric acid, ethylenediaminetetraacetic acid (EDTA), sorbitol, tartaric acid, and phosphoric acid.

\* \* \* \* \*